United States Patent [19]

Jakubowski et al.

[11] Patent Number: 5,849,766

[45] Date of Patent: Dec. 15, 1998

[54] CARBAMOYL SUBSTITUTED HETEROCYCLES

[75] Inventors: Joseph Anothony Jakubowski, Indianapolis, Ind.; Dale Eugene Mais, Valley Center, Calif.; Kumiko Takeuchi, Indianapolis, Ind.

[73] Assignee: Eli Lilly and Company, Indianapolis, Ind.

[21] Appl. No.: 862,505

[22] Filed: May 23, 1997

Related U.S. Application Data

[60] Provisional application No. 60/018,595 May 31, 1996.

[51] Int. Cl.$^6$ .......................... C07D 413/10; A61K 31/44
[52] U.S. Cl. ..................... 514/340; 514/236.8; 514/318; 544/131; 546/271.4; 546/194
[58] Field of Search .......................... 546/271.4; 514/340

[56] References Cited

U.S. PATENT DOCUMENTS

| | | | |
|---|---|---|---|
| 4,980,478 | 12/1990 | Hatanaka et al. | 546/346 |
| 5,100,889 | 3/1992 | Misra et al. | 514/365 |
| 5,153,327 | 10/1992 | Misra et al. | 548/237 |
| 5,158,967 | 10/1992 | Hall | 514/374 |
| 5,162,352 | 11/1992 | Hall et al. | 514/374 |

FOREIGN PATENT DOCUMENTS

| | | |
|---|---|---|
| 0 135 316 | 3/1985 | European Pat. Off. . |
| 0 337 640 | 4/1989 | European Pat. Off. . |
| 0 374 952 | 6/1990 | European Pat. Off. . |
| 0 391 652 | 10/1990 | European Pat. Off. . |
| 0 476 994 | 3/1992 | European Pat. Off. . |
| 0 497 085 | 8/1992 | European Pat. Off. . |
| 0 497 629 | 8/1992 | European Pat. Off. . |
| 0 536 713 | 4/1993 | European Pat. Off. . |
| 58-219162 | 12/1983 | Japan . |

OTHER PUBLICATIONS

Misra, R.N., et al., *Bioorg. & Med. Chem. Letters*, 1, 461–464, (1991).
Misra, R.N., et al., *Bioorg. & Med. Chem. Letters*, 1, 465–470, (1991).
Misra, R.N., et al., *Bioorg. & Med. Chem. Letters*, 2, 73–76, (1992).
Vermylen, J., et al., *Cardiovascular Drugs and Therapy*, 6, 29–33, (1992).
Soyka, R., et al., *J. Med. Chem.*, 37, 26–39 (1994).
Takeuchi, K., et al., *Bioorg. & Med. Chem. Letters*, 2, 743–755, (1994).
Ishikura, M., et al., *Heterocycles*, 22(11), 2475–2478 (1984).
Negishi, E., et al., *Heterocycles*, 18, 117–122 (1982).
Sakamoto, T., et al., *Heterocycles*, 31(2), 219–221, (1990).
Parrain, et al., *Tetrahedron Letters*, 31(13), 1857–1860, (1990).

*Primary Examiner*—Jane Fan
*Attorney, Agent, or Firm*—Thomas E. Jackson; David E. Boone

[57] ABSTRACT

This invention relates to carbamoyl substituted heterocycles which are ω-phenyl-ω-(3-pyridyl)-ω-alkenoic acid derivatives bearing a carbamoyl substituted oxazolyl or oxazolinyl group on the phenyl ring and which demonstrate utility for thromboxane receptor antagonism and/or thromboxane synthase inhibition, as well as pharmaceutical formulations containing them, methods for their use, and processes and intermediates for their preparation.

31 Claims, No Drawings

CARBAMOYL SUBSTITUTED HETEROCYCLES

This application claims the benefit of U.S. Provisional application Ser. No. 60/018,595, filed May 31, 1996.

This invention relates to carbamoyl substituted heterocycles which demonstrate utility for thromboxane receptor antagonism and/or thromboxane synthase inhibition. The compounds are ω-phenyl-ω-(3-pyridyl)-ω-alkenoic acid derivatives bearing a carbamoyl substituted oxazolyl or oxazolinyl group on the phenyl ring.

Thromboxane $A_2$ ($TXA_2$) is an unstable endogenous arachidonic acid metabolite which plays a pivotal role in platelet aggregation and vasoconstriction and has been implicated as a contributor to cardiovascular, renal, and pulmonary diseases. Cyclo-oxygenase inhibitors, thromboxane receptor antagonists (TRAs) and thromboxane synthase inhibitors (TSIs) have been developed to treat such disorders. Because of the limited clinical efficacy observed with TRAs and TSIs, it is believed that superior antithrombotic efficacy will be obtained by using a combined TRA/TSI agent over either class of agent alone or aspirin. The limited efficacy of TSIs has b ee n ascribed to prostaglandin $H_2$ ($PGH_2$) which accumulates due to the inhibition of thromboxane synthase. Because of agonist activity at the thromboxane receptor, $PGH_2$ activates the receptor in the absence of $TXA_2$ and thereby nullifies the benefits of reduced $TXA_2$ levels. Concomitant antagonism at the $TXA_2$ receptor will blunt this effect Of $PGH_2$. Nevertheless, clinical utility may be obtained by a compound which acts principally as a TSI or, particularly, principally as a TRA.

The control of thromboxane $A_2$ is useful for treating a variety of diseases and conditions, including, but not limited to, renal disease (e.g., hydronephrosis, transplant rejection, and renal nephritis), pulmonary disease, (e.g., asthma and pulmonary hypertension), prevention and treatment of hepatic and intestinal damage, cardiovascular disease (e.g., arteriosclerosis, thrombosis, vasospastic disease, hypertension, and shock), or complications resulting from surgical procedures such as angioplasty and coronary bypass surgery, for example restenosis.

Thromboxane $A_2$ control may be achieved by several routes, for example by cyclo-oxygenase inhibition, thromboxane receptor antagonism or by thromboxane synthase inhibition. Most often therapeutic agents have one or the other activity. It is highly desirable, however, to utilize therapeutic agents having the dual activities of thromboxane receptor antagonism and thromboxane synthase inhibition. Thus, it is a significant contribution to the art to provide novel, dual-acting TRA/TSI compounds.

7-Oxabicyclo[2.2.1]heptane derivatives which are said to possess TRA activity or dual TRA/TSI activity are disclosed in EP 374952 A, but no pharmacological data is provided therein. Substituted ω-phenyl-ω-(3-pyridyl) alkenoic acids which are dual-acting TRA/TSI agents are described in K. Takeuchi et al., *Bioorganic & Medicinal Chemistry*, (1994), 2, 743–755, as well as in R. Soyka, et al., *J. Med. Chem.*, (1994), 37, 26–39.

The present invention provides a novel series of phenyl oxazoles and phenyl oxazolines as potent and effective compounds which antagonize thromboxane at receptor sites in the body and/or inhibit thromboxane synthase and which, therefore, are useful in treating conditions associated with excessive or unregulated thromboxane activity.

Thus, according to the invention, there is provided a compound of Formula I

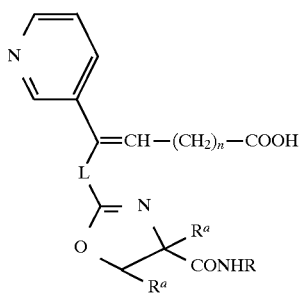

in either the E-form, the Z-form or a mixture thereof, wherein n is 2, 3, 4 or 5;

L is ortho-, meta- or para-phenylene;

each $R^a$ is hydrogen or the two together form a double bond; and

R is (3–12C)alkyl, (3–12C)alkenyl, (3–12C)alkynyl, 2-phenylcyclopropyl or $R^b$-(1–6C)alkyl in which $R^b$ is (3–8C)cycloalkyl, phenyl, tetrahydropyranyl, morpholino, piperidino or pyrrolidino wherein a phenyl group of the radical R may bear a 4-substituent selected from halo, (1–2C)alkyl and (1–2C)alkoxy; a cyclohexyl group of the radical R may bear a 4-substituent selected from (1–2C)alkyl and (1–2C)alkoxy; and in which one or two methylene groups of a (3–12C)alkyl, (3–12C)alkenyl, (3–12C)alkynyl, or the alkyl portion of $R^b$-(1–6C) alkyl may be replaced by an oxy group; and further provided that at least two carbon atoms separate any oxygens or nitrogens in the residue —NHR;

or a pharmaceutically acceptable salt thereof.

This invention also relates to a pharmaceutical formulation comprising the compound of Formula I (or a prodrug thereof) or a pharmaceutically acceptable salt thereof, together with a suitable diluent or carrier.

In another embodiment this invention provides a method for the treatment or prevention of a condition associated with excessive or unregulated thromboxane $A_2$ activity which comprises administering to a mammal in need thereof an effective amount of a compound of Formula I or a pharmaceutically acceptable salt thereof.

This invention further provides a method of inhibiting thromboxane production in a mammal by administering a therapeutically effective dose of a compound of the invention to the mammal.

This invention additionally provides an improved method of conducting surgical operations such as angioplasty and bypass surgery in a mammal by administrating to the mammal a therapeutically effective dose of a compound of the invention.

For any of the above methods, one particular mammal is a human, and another particular mammal is a companion animal such as, for example, a cat or a dog.

The term "effective amount" as used herein, means an amount of the compound of the invention which is capable of inactivating $TXA_2$ synthase and/or antagonizing thromboxane receptors in human blood platelets and other cells to an extent which achieves a beneficial therapeutic and/or prophylactic result.

In this specification, the following definitions are used, unless otherwise described: Halo is fluoro, chloro, bromo or iodo. Alkyl, alkoxy etc. denote both straight and branched groups; but reference to an individual radical such as "propyl" embraces only the straight chain ("normal") radical, a branched chain isomer such as "isopropyl" being referred to specifically. If a compound of Formula I contains a chiral element, it may exist in, and be isolated in, optically active and racemic forms. If a compound of Formula I contains an additional chiral element, such compound of Formula I may exist in, and be isolated in, the form of a diastereomeric mixture or as a single diastereomer. It is to be understood that the present invention encompasses a compound of Formula I as a mixture of diastereomers, as well as the form of an individual diastereomer, and that the present invention encompasses a compound of Formula I as a mixture of enantiomers, as well as in the form of an individual enantiomer.

A compound of Formula I, or a pharmaceutically acceptable salt thereof, may form a solvate. The compound, pharmaceutically acceptable salt or solvate may exhibit poly-morphism. It is to be understood, therefore, that the present invention encompasses any mixture of E- and Z-isomers, any racemic or optically active form, any pharmaceutically active salt, any solvate or any mixture thereof, which form possesses TRA and/or TSI properties, it being known in the art how to prepare optically active forms (for example, by resolution of the racemic form or by synthesis from optically active starting materials) and how to determine the TRA/TSI properties by standard tests including those described below.

It is preferred that the radical R not contain or introduce an element of chirality into the compound of Formula I.

The invention provides compounds of the Formula I which generally have a dual function of antagonizing thromboxane at the receptor sites in the body and inhibiting thromboxane synthase. A preferred compound of this invention is one of Formula I wherein the double bond is of the E-form. It will be appreciated that the compound of Formula I which is in the E-form may contain a minor amount of the corresponding Z-form, such as for example twenty percent, ten percent, five percent, two percent, one percent or less, as a less active constituent. Alternatively, the compound of Formula I may be described in terms of the ratio of the isomeric forms, the E/Z ratio, such as for example an E/Z ratio of 4:1, 9:1, 19:1, 49:1 or higher. In general, the E-form of a compound of Formula I has an E/Z ratio of at least 19:1; i.e. no more than five percent of the Z-form is included.

It is also preferred that a compound of Formula I as described above be one in which L is meta-phenylene or para-phenylene.

One preferred compound of Formula I is one in which the double bond is in the E-form and L is para-phenylene.

For any compound of Formula I as described above, a preferred value for n is 3 or 4.

One particularly preferred compound of Formula I is one in which the double bond is in the E-form, n is 4, L is para-phenylene, the two $R^a$ groups together form a double bond, and R is defined as above, which compound is represented by Formula Ia.

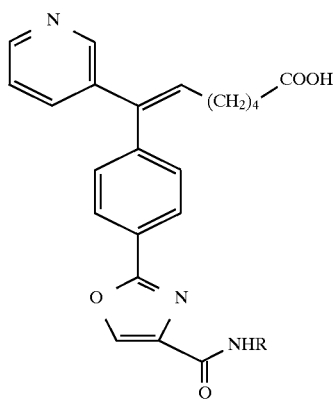

For any of the above definitions of a compound of Formula I (or Ia), a particular value of R is pentyl, 3-ethoxypropyl, 3-(2-methoxyethoxy)propyl, trans-2-phenylcyclopropyl, cyclopropylmethyl, 4-cyclohexylbutyl, 3-(4-methoxycyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy)propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)ethyl or 3-morpholinopropyl. A preferred value of R is 4-cyclohexylbutyl.

Specific compounds of Formula I are described in the accompanying Examples. Of these the compounds described as Example 2 and as Example 30 are preferred.

By virtue of its acidic moiety, a compound of Formula I forms salts with pharmaceutically acceptable bases. Such a pharmaceutically acceptable salt may be made with a base which affords a pharmaceutically acceptable cation, which includes alkalai metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

Compounds of Formula I which are basic also form pharmaceutically acceptable acid addition salts with pharmaceutically acceptable acids. Preferred pharmaceutically acceptable acid addition salts are those formed with mineral acids such as hydrochloric acid and hydrobromic acid, and those formed with organic acids such as maleic acid, citric acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole.

A compound of Formula I may be made by a process which is analogous to one known in the chemical art for the production of structurally analogous heterocyclic compounds or by a novel process described herein. Such processes and intermediates useful for the manufacture of a compound of Formula I as defined above are provided as further features of the invention and are illustrated by the following procedures in which, unless otherwise specified, the meanings of the generic radicals are as defined above.

(A) Decomposing an ester of Formula II,

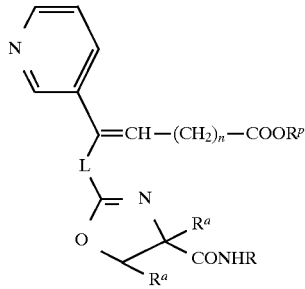

II in which $R^p$ forms a carboxy-protecting ester group. A carboxy-protecting ester group is one of the ester derivatives of the carboxylic acid group commonly employed to block or protect the carboxylic acid group while reactions are carried out on other functional groups of the compound. Particular values of $R^p$ include, for example, methyl, ethyl, tert-butyl, benzyl, methoxymethyl, trimethylsilyl, and the like. Further examples of such groups may be found in T. W. Greene and P. G. M. Wuts, "Protecting Groups in Organic Synthesis" (1991). The ester is decomposed by using a conventional procedure which does not affect another portion of the molecule. For example, basic hydrolysis of a compound of Formula II in which $R^p$ is methyl or ethyl using 1N sodium hydroxide and an organic cosolvent, such as tetrahydrafuran, methanol and/or ethanol, at room temperature for 3–4 hours, followed by acidification, provides the acid of Formula I, for example as described in Examples 1-L, 2-B and 18-G. For preparation of a compound of Formula Ia, a corresponding compound of Formula II may be represented as a compound of Formula IIa,

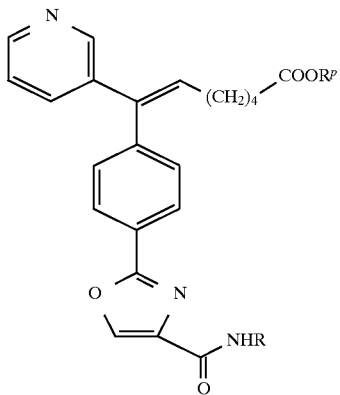

IIa in which $R^p$ is defined as above.

When the alcohol of formula $R^pOH$ is a pharmaceutically acceptable alcohol and the ester of Formula II or Formula IIa is metabolically hydrolyzable, the compound of Formula II or Formula IIa provides a prodrug for the corresponding compound of Formula I or Formula Ia; and this provides an additional aspect of the invention.

(B) Condensing a ketone of Formula III

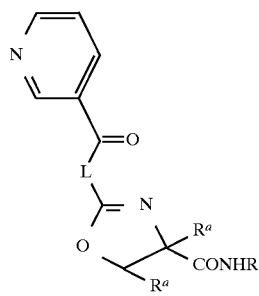

III with a phosphorane of Formula IV

$(C_6H_5)_3P=CH-(CH_2)_{hd\ n}-COO^{\ominus}\ M^{\oplus}$   IV in which M is an alkali or alkaline earth metal, preferably potassium, followed by acidification. In this procedure the E-form of the compound of Formula I typically is the predominant isomer; and the isomers are further separated as required. For example, in condensations with the compound of Formula IIIa (below) in which R is 4-cyclohexylbutyl, E/Z ratios of 6.2:1, 3:1, 8.7:1 and 10.6:1 were obtained for n=2, 3, 4 and 5, respectively. Conveniently, the phosphorane of Formula IV is formed in situ from the corresponding salt of Formula V,

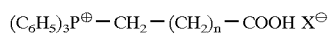

$(C_6H_5)_3P^{\oplus}-CH_2-(CH_2)_n-COOH\ X^{\ominus}$   V in which X is typically bromide, in tetrahydrofuran at 0° C. by treatment with potassium tert-butoxide. Upon completion of the condensation, the reaction mixture is acidified, conveniently with aqueous ammonium chloride, and the acid(s) of Formula I isolated, for example as described in Example 18-G, etc. For preparation of a compound of Formula Ia, a corresponding ketone of Formula III may be represented as a ketone of Formula IIIa.

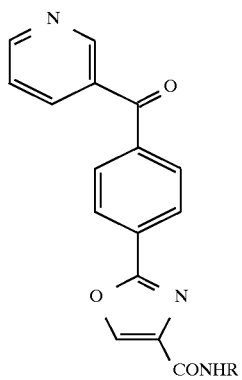

IIIa (C) For a compound of Formula I in which the two $R^a$ groups together form a double bond (an oxazole), dehydrogenating a corresponding compound of Formula I in which each $R^a$ is hydrogen (an oxazoline). The dehydrogenation is carried out using a conventional method, for example in a manner analogous to the nickel peroxide oxidation of the ester described in Example 2-A.

Whereafter, for any of the above procedures, when a pharmaceutically acceptable salt of a compound of Formula I is required, it is obtained by reacting the acid of Formula I with a physiologically acceptable base or by reacting a basic compound of Formula I with a physiologically acceptable acid or by any other conventional procedure.

If not commercially available, the necessary starting materials for the above procedures may be made by procedures which are selected from standard techniques of organic and heterocyclic chemistry, techniques which analogous to the syntheses of known, structurally similar compounds, and the procedures described in the Examples, including novel procedures.

One general route to an intermediate of Formula II is outlined below in Scheme 1 and described in detail in the Examples for a compound in which L is para-phenylene, n is 4, $R^p$ is methyl and R is 4-cyclohexylbutyl.

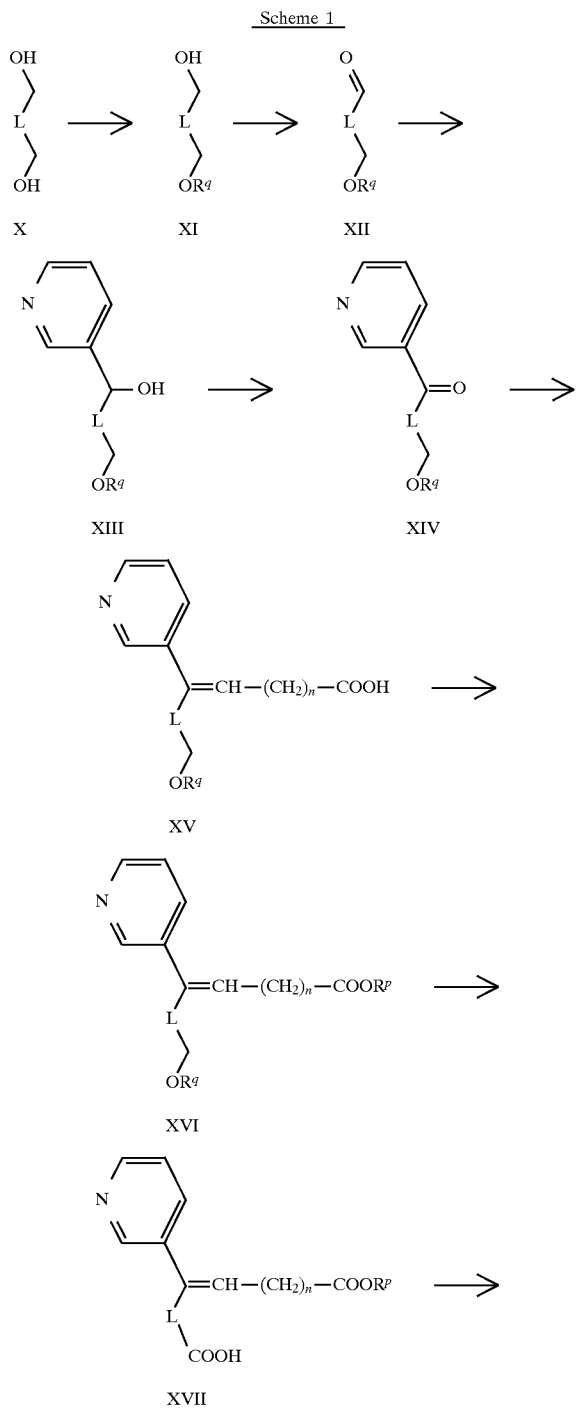

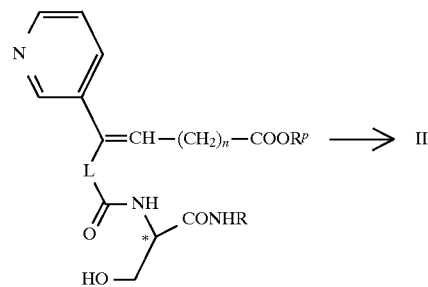

Thus, one hydroxy group of a benzenedimethanol X is protected with a hydroxy-protecting group $R^q$ to provide a benzyl alcohol of Formula XI. The term "hydroxy-protecting group" as used herein refers to a substituent of the hydroxy group commonly employed to block or protect the hydroxy functionality while reacting other functional groups on the compound. Examples of such a hydroxy-protecting group include trimethylsilyl, tert-butyldimethylsilyl, methoxymethyl, benzyloxymethyl, methoxyethoxymethyl, 2-(trimethylsilyl)ethoxymethyl, methylthiomethyl and tetrahydropyranyl. The tert-butyldimethylsilyl (TBS) group is conveniently used in this route. Further examples of such groups may be found in T. W. Greene and P. G. M. Wuts, "Protective Groups in Organic Synthesis" (1991) at Chapter 3. The TBS group may be introduced using the standard method described in Example 1-A; or it may be preferred to first form a mono-alkoxide, using sodium hydride in an acceptable solvent, before treatment with tert-butyldimethylsilyl chloride.

Oxidation of the alcohol of Formula XI, conveniently with manganese dioxide, affords the aldehyde of Formula XII. Condensation with 3-pyridyl lithium provides the carbinol of Formula XIII, which affords the intermediate ketone of Formula XIV upon oxidation, again conveniently using manganese dioxide.

Condensation of a ketone of Formula XIV with a phosphorane of Formula IV (followed by acid work-up) provides an acid of Formula XV as a separable mixture of E- and Z-forms in which the Z-form predominates. An E/Z ratio of about 1:4 was obtained when L was ortho- or para-phenylene, and an E/Z ratio of about 1:3 was obtained when L was meta-phenylene. The Z-isomers were found to be the less polar form in chromatography. The isomeric acids may be separated; or they may be converted into the corresponding separable carboxy-protected derivatives of Formula XVI before separation. Alternatively, separation of the E- and Z-forms can be accomplished at a later stage.

When $R^q$ is TBS, the silyl ether of Formula XVI may be oxidized directly to the acid of Formula XVII using Jones reagent. Following a convergent strategy, the acid of Formula XVII is coupled with a preformed serinamide (in which the hydroxy group may be free or protected by a hydroxy-protecting group as described above for $R^q$, for example TBS) to afford an amide of Formula XVIII. The coupling is carried out by using a conventional procedure; for example by using carbonyl diimidazole (CDI), dicyclohexylcarbodiimide (DCC) with 1-hydroxybenzotriazole (HOBT) or, preferably, 1-(1-dimethylaminopropyl)-3-ethylcarbodiimide hydrochloride or hydroiodide, known as water soluble carbodiimide (WSC). The alcohol of Formula XVIII is cyclized to afford the corresponding oxazoline of Formula II, in which each $R^a$ is hydrogen, by a conventional method; conveniently with triphenylphosphine and carbon tetrachloride and an organic base such as diisopropylethylamine in acetonitrile. If the initial serinamide is not racemic at the α-position and conditions are employed which avoid racemization, the enantiomeric excess will be maintained in the amide of Formula XVIII at the corresponding α-carbon (indicated by "*" in Formula XVIII) and at the C-4 carbon of the oxazoline of Formula II.

A compound of Formula II in which each $R^a$ is hydrogen (an oxazoline) may be dehydrogenated to a corresponding compound of Formula II in which the two $R^a$ groups together form a double bond (an oxazole) by using a conventional procedure, for example by employing nickel peroxide oxidation.

Another route to the E-form of an intermediate of Formula II is outlined below in Scheme 2 (in which Tf denotes trifluoromethylsulfonyl) and described in detail in the Examples for a compound in which n is 3, L is para-phenylene, the two Ra radicals together form a double bond, $R^p$ is tert-butyl and R is 4-cyclohexylbutyl.

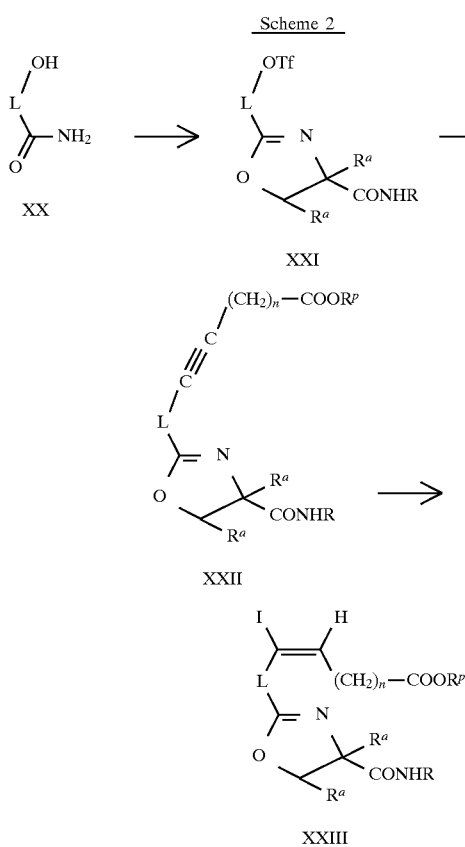

Thus, a monosubstituted acetylene is cross-coupled with the triflate of Formula XXI to afford the disubstituted acetylene of Formula XXII. Stereoselective cis-addition of the elements of H-I to the alkyne then affords the E-olefin XXIII, which is cross coupled with a 3-pyridyl tin derivative to afford the E-ester of Formula II.

For preparation of a compound of Formula IIa, a corresponding iodide of Formula XXIII may be represented as a compound of Formula XXIIIa.

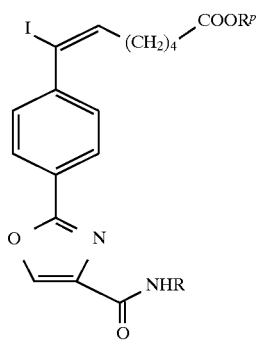

It will be clear that the order of steps in the above routes can be changed so that a compound of Formula II is prepared from a corresponding acid of Formula VI,

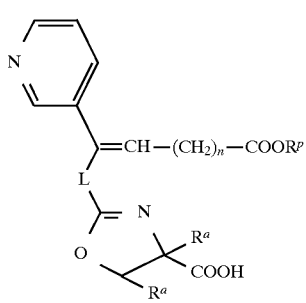

or an activated derivative thereof, and an amine of Formula R-NH$_2$. The acid of Formula VI can be obtained by removal of a carboxy-protecting group $R^r$ of a compound of Formula VII

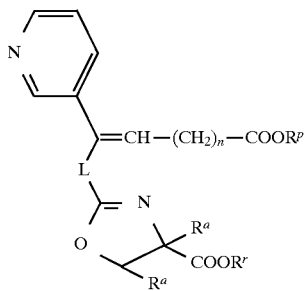

in which $R^r$ is a carboxy-protecting group which can be removed selectively in the presence of the carboxy-protecting group $R^p$. A diester of Formula VII may be prepared using a similar route to that outlined in Scheme 2; other routes to a compound of Formula VII are outlined below.

Also, it may be useful to convert an acid of Formula I into a protected derivative of Formula II for separation and purification before converting the compound of Formula II back into the acid.

Preparative routes to a ketone of Formula III are outlined below in Scheme 3 and described in detail in the Examples for a compound in which L is para-phenylene and R is phenethyl.

Scheme 3

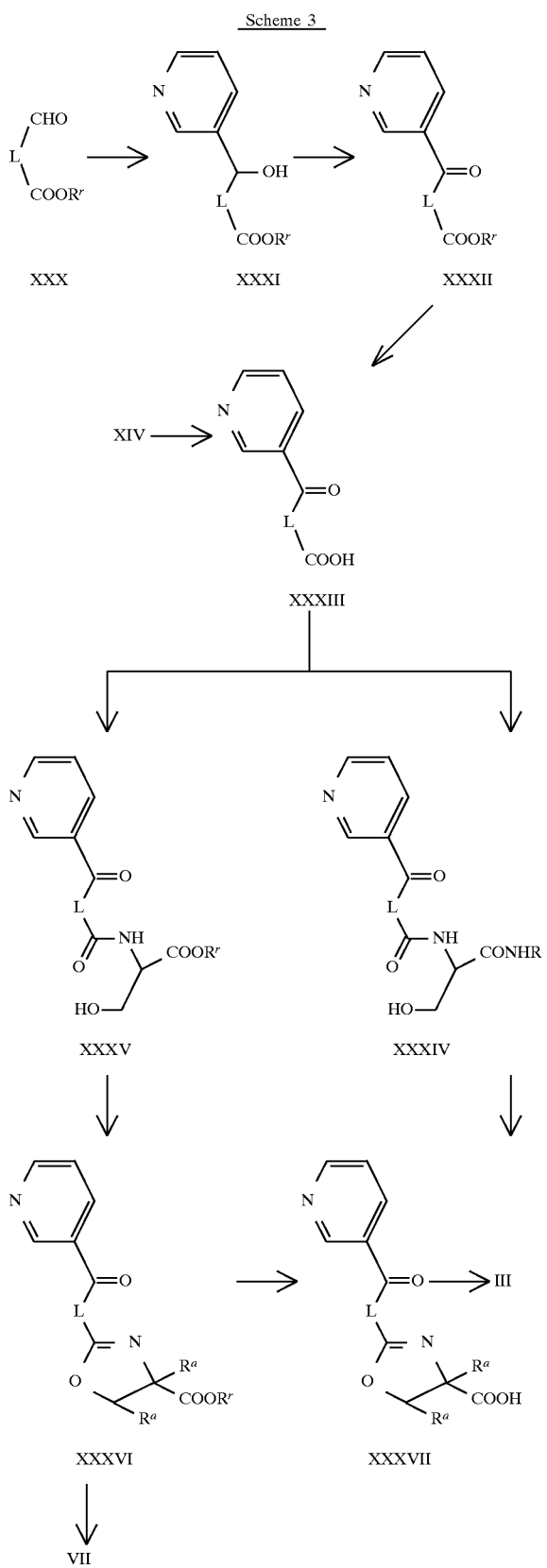

A formylbenzoate (conveniently the methyl ester) of Formula XXX is condensed with 3-pyridyl lithium to provide a carbinol of Formula XXXI. Oxidation of the carbinol, conveniently using manganese dioxide, affords a keto ester of Formula XXII. Hydrolysis of the ester affords the keto acid of Formula XXXIII. This key acid also may be obtained by oxidation of an alcohol of Formula XIV, using Jones reagent, for example.

Using similar methodology to that described above, the acid of Formula XXXIII is coupled with a preformed serinamide to form a diamide of Formula XXXIV, and cyclization is affected to afford an oxazoline of Formula III in which each $R^a$ is hydrogen. The oxazoline is converted into the corresponding oxazole of Formula III in which the two $R^a$ groups together form a double bond by using a conventional procedure as described herein.

An alternative route to a compound of Formula III involves coupling the benzoic acid of Formula XXXIII with a serine ester to provide an amide of Formula XXXV in which $R^r$ designates a carboxy-protecting group, conveniently the methyl group. The amide is then cyclized to an oxazoline of Formula XXXVI in which each $R^a$ is hydrogen by using the methodology described above or, preferably, using trifluoromethanesulfonic anhydride (triflic anhydride) and diphenyl sulfoxide in the presence of potassium phosphate as described in Example 25-B. An oxazoline of Formula XXXVI may be converted into an oxazole of Formula XXXVI in which the two $R^a$ groups together form a double bond by using conventional methodology, for example as described above or with manganese dioxide and ultrasonication in a suitable solvent. Deprotection of the carboxy group of a compound of Formula XXXVI affords a corresponding acid of Formula XXXVII which is coupled with an amine of Formula R-NH$_2$ to provide a keto amide of Formula III.

A ketone of Formula XXXVI also may be converted into an ester of Formula VII by using a procedure analogous to (B) above, followed by protection of the carboxy group with a group $R^p$.

It may be desired to use a protecting group during all or portions of the above-described processes; the protecting group then may be removed when the final compound or a required starting material is to be formed. As will be clear to one skilled in the art, the order of steps in the sequences leading to the starting materials and products of the invention may be altered if appropriate consideration relating to coupling methods, racemization, deprotection methods, etc., are followed.

The utility of a compound of the invention or a pharmaceutically acceptable salt thereof (hereinafter, collectively referred to as a "Compound") may be demonstrated by standard tests and clinical studies, including those described below.

Measurement of Thromboxane Receptor Antagonism:

1. Receptor Binding Assay. Membranes from outdated human platelets were prepared as previously described (Mais, D. E., et al., Eur. J. Pharmacol. (1992), 227, 267–274). Incubations (220 μL) containing 10 μg of platelet membranes were performed in siliconized glass tubes (12× 75 mm) at 30° C. for 30 min. The incubation media consisted of 10 mM Hepes, 2 mM CHAPS, 10 μM Indomethacin (pH=7.4), ~0.05 nM (~25000 cpm) of [$^{125}$I] IBOP per tube, and varying concentrations of competing ligands ranging from $10^{-10}$ to $10^{-5}$M. The reaction was terminated by addition of 4 mL of ice cold buffer (25 mM Tris) at pH 7.4, followed by rapid filtration through Whatman GF/C glass filters pre-soaked in 0.3% polyethyleneamine (Whatman, Inc., Clifton, N.J.) using a Brandel M-24 cell harvester (Gaithersburg, Md.). Non-specific binding was defined as that amount of radioactivity bound in the presence of a large molar excess (10 μM) of SQ29548, a potent TXA$_2$/PGH$_2$ receptor antagonist. The binding in this assay is defined in terms of the dissociation constant Kd. In general, the exemplified compounds of the invention were found to have a Kd of 10,000 nM, or much less; however, a Kd of greater than 10,000 nM was determined for the compound of Example 27, which has a basic moiety in R. For the compounds of Examples 1, 2, 19, 26 and 30, respectively, Kd values of 15.5, 9.9, 62.6, 58.2 and 52.2 nM were measured.

2. Platelet Aggregation Studies. The ability of a test compound to antagonize TXA$_2$/PGH$_2$ receptor-induced human platelet aggregation was studied in the following manner. Blood was collected from volunteers who denied taking any medication known to influence platelet aggregation within the previous 10 days. The blood was collected onto ⅒th volume of 3.8% trisodium citrate and mixed by gentle inversion. Platelet-rich plasma was prepared by centrifugation at 100×g for 12 min, and platelet-poor plasma was prepared by centrifugation at 12,000×g for 2 min. Receptor activation and subsequent platelet aggregation was induced by the addition of the stable analog of TXA$_2$/PGH$_2$, U46619 (1 micromolar). Aggregation was monitored in a Biodata PAP4 platelet aggregation profiler for 3 min after the addition of U46619. Test compound or vehicle was preincubated with platelet-rich plasma for 1 min at 37° C. prior to the induction of aggregation with U46619. Data are expressed as the IC$_{50}$, i.e., concentration of test compound required to inhibit U46619-induced platelet aggregation by 50%. IC$_{50}$ values of 0.4, 5, 5 and 0.5 μM were measured for the compounds of Example 2, 19, 26 and 30, respectively.

3. Absence of Agonist Activity. The absence of TXA$_2$ agonist activity was demonstrated by the absence of a pressor response following the i.v. administration of the compound of Example 2 to pithed rats at doses up to 10 mg/kg. In contrast, the TRA compound known as S-145 induced a transient, but significant, increase in the mean arterial pressure at one minute after dosing at 0.1 mg/kg i.v. Measurement of Thromboxane Synthase Inhibition and Prostacyclin Formation:

1. In vitro Experiments. The ability of a test compound to inhibit thromboxane synthase, as well as to change the amount of prostacyclin formed, were measured using published methods. Thus, compound or vehicle was incubated with whole human blood for 30 min at 37° C. prior to the preparation of serum as previously described (Jakubowski, J. A., et al., *Brit. J. Haematol*, (1985), 60, 635–642). Serum TXB$_2$ and 6-keto-PGF$_{1\alpha}$, the stable metabolites of TXA$_2$ and prostacyclin (PGI$_2$), respectively, were measured by radioimmunoassay as described (Jakubowski, J. A., et al., *Arteriosclerosis*, (1987), 7, 599–604). The ability of a test compound to inhibit thromboxane synthase is expressed in the form of its IC$_{50}$. In general, the exemplified compounds of the invention were found to have an IC$_{50}$ of 10,000 nM, or much less. However, some of the compounds in which the double bond is in the Z-form, for example the compounds of Examples 3 and 4, were found to have IC$_{50}$ values in excess of 10,000 nM. For the compounds of Examples 1, 2, 19, 26 and 30, respective IC$_{50}$ values of 82.1, 55.0, 8.5, 11.5 and 48.9 nM were obtained.

2. Ex Vivo Experiments: The ability of a test compound to inhibit TXA$_2$ formation following oral administration was demonstrated as follows. Sprague Dawley rats (300 g males) were dosed by oral gavage with either vehicle (5% acacia) or 1–10 mg/kg test compound. Blood samples were collected 1 h after dosing. Animals were anesthetized (sodium pentobarbitol, 87 mg/kg i.p.) 15 min before sample collection. Blood samples were obtained by cardiac puncture via a butterfly catheter and the first mL of blood was discarded. Blood samples were divided into duplicates and incubated at 37° C. for 1 h in 13×100 mm glass tubes. Serum was separated by centrifugation at 2000×g for 15 min at 25° C., transferred to polypropylene tubes, and stored at −20° C. for subsequent assay using the methods referenced above. In this procedure, greater than 95% inhibition of TXA$_2$ formation was observed one hour after a 3 mg/kg dose of the compound of Example 2.

As noted above, this invention also provides a pharmaceutical formulation comprising a compound of Formula I (or a prodrug thereof), or a pharmaceutically acceptable salt thereof, together with a suitable diluent or carrier. The active ingredient of such a formulation is a compound of Formula I, or a pharmaceutically acceptable salt or solvate thereof, or a prodrug thereof.

For the pharmaceutical formulation any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The formulation according to the invention may be made for oral, parenteral or rectal administration or in a form suitable for administration by inhalation or insufflation, either through the mouth or nose.

The following pharmaceutical formulations 1 thru 8 are illustrative only and are not intended to limit the scope of the invention in any way. "Active ingredient," refers to a compound according to Formula I or a pharmaceutically acceptable salt, solvate, or prodrug thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
| --- | --- |
| Isotonic saline | 1,000 ml |

The solution of the above ingredients generally is administered intravenously to a subject at a rate of 1 ml per minute.

As noted above, one embodiment of this invention is a method for the treatment or prevention of a condition associated with excessive or unregulated thromboxane $A_2$ activity which comprises administering to a mammal in need thereof an effective amount of a compound of Formula I or a pharmaceutically acceptable salt thereof.

One aspect of the above method is the treatment or prevention of renal disease, particularly glomerular nephritis, diabetic nephropathy, or transplant rejection.

Another aspect of the above method is the treatment of pulmonary disease, for example inhibiting bronchoconstriction associated with asthma.

A further aspect of the above method is the prevention or treatment of vascular disease including prevention or amelioration of stroke or myocardial infarction.

An additional aspect of the above invention is the prevention or reduction of complications, such as restenosis, arising from surgical procedures such as angioplasty and coronary bypass surgery.

A specific dose of a compound of the invention administered to obtain therapeutic and/or prophylactic effects will, of course, be determined by the particular circumstances surrounding the case, including, for example, the route of administration and the condition being treated. A typical daily dose will contain a non-toxic dosage level of the compound of from about 0.01 mg/kg to about 50 mg/kg of body weight. Preferred daily doses generally will be from about 0.05 mg/kg to about 20 mg/kg.

The invention will now be illustrated by the following non-limiting examples in which the following conditions were generally followed. All solvents and reagents were purchased from commercial sources and used as received, unless otherwise indicated. Tetrahydrofuran (THF) was distilled from sodium benzophenone ketyl prior to use. All reactions were performed under a positive pressure of dry nitrogen. The "preparative HPLC" was performed on a Waters PrepLC System 500A with the solvent indicated. Analytical HPLC was carried out on a Waters Model 510 using Nova $C_{18}$ column with $CH_3CN$-MeOH-$H_2O$ solvent system which contained 0.5% $NH_4OAc$ or Chiralcel OD-R column with $CH_3CN$-$H_2O$ solvent system which contained 0.1% $NaClO_4$. Flash chromatography was carried out on E. Merck Kieselgel 60 (230–400 mesh). $^1$H NMR spectra were recorded on a GE QE-300 (routine) and on Bruker AM-500 (NOE) spectrometer. The chemical shifts are given in δ values relative to residual proton resonances of the deuterated solvents used ($CDCl_3$ 7.26, DMSO-$d_6$ 2.49). Field desorption (FDMS) and fast atom bombardment mass spectra (FABMS) were obtained on a VG ZAB-3F or VG 70-SE instrument. Optical Rotation was obtained on a Perkin-Elmer 241 Polarimeter. Melting points are uncorrected. The routine elemental analyses which agree with calculated values within ±0.4% are not shown but indicate as Anal. ($C_nH_xN_yO_z$) C, H, N; analysis results outside the defined range are reported as, e.g., for an example in which N is outside the defined range, Anal. ($C_nH_xN_yO_z$) C, H, N: calcd 6.99; found 7.55

In addition to the abbreviations noted above, the following abbreviations are used herein:
Boc: t-butyloxycarbonyl
Bu: butyl
DMF: dimethylformamide
$Et_2O$: diethyl ether
EtOH: ethanol
EtOAc: ethyl acetate
$Et_3N$: triethylamine
LAH: lithium aluminum hydride
Ms: methanesulfonyl
Ph: phenyl
i-PrOH: 2-propanol
DCC: dicyclohexylcarbodiimide
HOBT: 1-hydroxybenzotriazole hydrate
NMM: 4-methylmorpholine
WSC: water soluble carbodiimide: 1-(3-dimethyl aminopropyl)-3-ethylcarbodiimide hydrochloride
MNNG: 1-methyl-3-nitro-1-nitrosoguanidine
TBS: t-butyldimethylsilyl
r.t.: room temperature
TLC: thin layer chromatography
ca.: about
concd: concentrated

EXAMPLES

Starting Materials: Certain starting materials for the Examples described below were prepared as follows:

Amine Formation: Amines which were not commercially available were prepared from corresponding alcohols in three steps. 3-(Cylohexyloxy)propanol was prepared from 3-phenoxy-propionic acid in two steps (71%): (1) hydrogenation ($H_2$, 5% Rh/C, HOAc, 50° C., 4 h); (2) reduction of the acid (1.0M LAH, $Et_2O$, 0° C.): $^1$H NMR ($CDCl_3$) δ53.78 (t, J=5.3 Hz, 2H), 3.66 (t, J=5.6 Hz, 2H), 3.26 (m, 1H), 2.87 (br s, 1H), 1.90–1.22 (m, 12H); FDMS 159 (M+1). (±)-2-(Tetrahydopyran-2-methoxy)ethanol was prepared from (±)-tetrahydropyran-2-methanol in two steps (57%): (1) alkylation (NaH, THF, 75° C.; methyl bromoacetate, 0° C.); (2) reduction of the ester (LAH, THF, 0° C.): $^1$H NMR ($CDCl_3$) δ4.00 (br d, J=11.2 Hz, 1H), 3.70 (br d, J=4.1 Hz, 2H), 3.58 (m, 2H), 3.46 (m, 4H), 2.85 (s, 1H), 1.84 (m, 1H), 1.50 (m, 4H), 1.32 (m, 1H); FDMS 161 (M+1). Anal. ($C_8H_{16}O_3$) C, H. Likewise, 2-(cyclohexylmethoxy)ethanol was prepared from cyclohexylmethanol in two steps (12%): $^1$H NMR ($CDCl_3$) δ3.70 (t, J=4.7 Hz, 2H), 3.50 (t, J=4.6 Hz, 2H), 3.26 (d, J=6.5 Hz, 2H), 2.34 (br s, 1H), 1.71 (m, 6H), 1.18 (m, 3H), 0.88 (m, 2H); FDMS 158 (M+).

The general procedure for amine formation was as follows. Each alcohol was converted to the corresponding azide via a mesylate in one-pot two reaction steps (70–99%): MsCl, $Et_3N$, DMF, 0° C., 1 h; then aqueous $NaN_3$, 60–70° C., 1–5.5 h (for a pyran derivative, toluene was used as solvent and n-$Bu_4N^+Br^-$ was added as a phase transfer catalyst; according to Synthesis (1990), 366–368). The azide was then reduced to a primary amine by Vaultier's method (*Tetrahedron Lett.* (1983), 24, 763–764): $Ph_3P$, $H_2O$, THF, r.t., overnight (89–98%).

2-(Benzyloxy)ethylamine: $^1$H NMR ($CDCl_3$) δ7.33 (m, 5H), 4.53 (s, 2H), 3.51 (t, J=5.2 Hz, 2H), 2.89 (br t, J=4.6 Hz, 2H), 1.50 (br s, 2H); FABMS calcd. for $C_9H_{14}NO$ 152.1075, found 152.1082, M+1.

3-(4-Methoxyphenyl)propylamine: $^1$H NMR ($CDCl_3$) δ7.09 (d, J=8.5 Hz, 2H), 6.81 (d, J=8.5 Hz, 2H), 3.77 (s, 3H), 2.70 (t, J=7.0 Hz, 2H), 2.58 (t, J=7.7 Hz, 2H), 1.72 (m, 2H), 1.24 (s, 2H); FDMS 165 (M+).

2-(Cyclohexyloxy)ethylamine: $^1$H NMR ($CDCl_3$) δ3.48 (t, J=5.1 Hz, 2H), 3.23 (m, 1H), 2.84 (t, J=5.3 Hz, 2H), 1.90 (m, 2H), 1.72 (m, 2H), 1.56 (m, 2H), 1.24 (m, 6H); FABMS calcd. for $C_8H_{18}NO$ 144.1388, found 144,1386, M+1.

3-(Cyclohexyloxy)propylamine: $^1$H NMR ($CDCl_3$) δ3.48 (t, J=6.2 Hz, 2H), 3.17 (m, 1H), 2.76 (t, J=6.7 Hz, 2H), 1.85 (m, 2H), 1.67 (m, 4H), 1.47 (br s, 2H), 1.19 (m, 6H); FABMS calcd. for $C_9H_{20}NO$ 158.1545, found 158.1554, M+1.

(±)-2-(Tetrahydropyran-2-ylmethoxy)ethylamine: $^1$H NMR ($CDCl_3$) δ4.00 (dt, J=11.3, 2.0 Hz, 1H), 3.54–3.35 (m, 8H), 2.86 (br s, 2H), 1.85–1.80 (m, 1H), 1.60–1.45 (m, 4H), 1.31 (m, 1H); FABMS calcd. for $C_8H_{18}NO_2$ 160.1338, found 160.1347, M+1.

2-(Cyclohexylmethoxy)ethylamine: $^1$H NMR ($CDCl_3$) δ3.44 (t, J=5.2 Hz, 2H), 3.24 (d, J=6.5 Hz, 2H), 2.86 (t, J=5.1 Hz, 2H), 1.78–1.55 (m, 8H), 1.20 (m, 3H), 0.94 (m, 1H); FABMS calcd. for $C_9H_{20}NO$ 158.1545, found 158.1558, M+1.

[(cis) and (trans)]-3-(4-Methoxycyclohexyl)-propylamine: A solution of 1.18 g (7.1 mmol) 3-(4-methoxyphenyl) propylamine in 50 mL of dioxane was hydrogenated at 138 bar and at 160° C. for 16 h in the presence of 0.5 g of 5% $Ru/Al_2O_3$. The catalyst was removed by filtration and the filtrate was concentrated to dryness. Preparative HPLC of the crude product by elution with 10% (10% concd $NH_4OH$ in MeOH)—$CH_2Cl_2$ furnished 723.5 mg (59%) of the cis/trans mixture of cyclohexylpropylamine (c/t=~3:1 by $^1$H NMR): $^1$H NMR ($CDCl_3$, cis-isomer only) δ3.37 (br s, 1H), 3.27 (s, 3H), 2.64 (t, J=7.0 Hz, 2H), 2.10–0.87 (M, 15H); FDMS 172 (M+1).

4-(Cyclohexyloxy)butylamine: A solution of 2.0 g of 4-phenoxybutylamine in 95 mL of EtOH was hydrogenated at 4.1 bar in the presence of 2.0 g of 5% Rh/C at 60° C. for 24 h. The catalyst was removed by filtration and the filtrate was concentrated. Preparative HPLC eluting with 10% (10% concd NH$_4$OH in MeOH)—CH$_2$Cl$_2$ furnished 279.7 mg (13%) of the reduction product along with 461.2 mg (23%) of the starting material: $^1$H NMR (CDCl$_3$) δ3.46 (t, J=6.1 Hz, 2H), 3.21 (m, 1H), 2.75 (br t, 2H), 2.00–1.15 (m, 16H); FDMS 172 (M$^+$).

3-[1-Cyclohexylethoxy]propylamine: To a solution of 38.4 g (0.3 mol) of cyclohexyl(methyl)carbinol in 100 mL of benzene was added 2.5 g of sodium methoxide in one portion at 20° C., followed by dropwise addition of 16.9 g (0.32 mol) of acrylonitrile. The mixture was stirred at room temperature for 2 h, heated at reflux for 1 h, and then left standing overnight at room temperature. The reaction mixture was acidified with HOAc and filtered. The filtrate was concentrated on the steam bath and the residue was distilled under vacuum to yield 30.3 g of colorless oil (bp 119°–121° C./800 Pa). The propionitrile obtained, 20 g (0.11 mol), in 100 mL of EtOH and 25 mL of liquid ammonia was hydrogenated at 90 bar in the presence of a half teaspoonful Raney Nickel at 80°–85° C. for 2 h. The catalyst was filtered off and the filtrate was concentrated. Vacuum distillation of the residue gave 16.2 g of the amine (44% for 2 steps): bp 108°–109° C./933 Pa; $^1$H NMR (CDCl$_3$) δ3.59 (dt, J=9.3, 5.9 Hz, 1H), 3.39 (dt, J=9.3, 6.1 Hz, 1H), 3.10 (dq, J=6.2, 6.2 Hz, 1H), 2.85 (t, J=6.7 Hz, 2H), 2.42 (br s, 2H), 1.84°–1.62 (m, 7H), 1.36 (m, 1H), 1.29–0.87 (m, 8H). Anal. (C$_{11}$H$_{23}$NO) C, H, N.

Serinamide formation: Serinamides were prepared in two steps from N-Boc-L-serine and various amines as were N-(4-cyclohexylbutyl)-L-serinamide and N-pentyl-L-serinamide (EP 374952 A2, Jun. 27, 1990): (1) amide coupling (WSC, HOBT, NMM, DMF, overnight; (2) removal of the Boc group (CF$_3$CO$_2$H, CH$_2$Cl$_2$, 0° C. to r.t.).

N-Benzyl-L-serinamide: To a mixture of 4.10 g (20 mmol) of N-Boc-L-serine, 2.97 g (22 mmol) of HOBT, 2.42 mL (22 mmol) of NMM, and 2.40 mL (22 mmol) of benzylamine in 50 mL of anhydrous DMF at 0° C. was added 4.21 g of WSC. The mixture was stirred at 0° C. for 1 h and at room temperature for 3 h. This was then taken up in 300 mL of EtOAc and washed with 100 mL of H$_2$O (2×) and brine (1×). The combined organic layers were dried over MgSO$_4$ and concentrated. After drying under vacuum overnight, the residue was dissolved in 20 mL of CH$_2$Cl$_2$ and treated with 20 mL of CF$_3$CO$_2$H at 0°–10° C. for ca. 7 h. The solvent and CF$_3$CO$_2$H were removed under vacuum. The trace CF$_3$CO$_2$H was removed azeotropically with CHCl$_3$ at the end. The residue was purified by preparative HPLC, eluting with 8% (10% conc. NH$_4$OH in MeOH)—CH$_2$Cl$_2$ to afford 3.57 g (92%) of the serinamide: mp 97–98° C.; $^1$H NMR (CDCl$_3$) δ7.82 (br s, 1H), 7.26 (m, 5H), 4.42 (ddd, J=16.7, 15.0, 6.0 Hz, 2H), 3.85 (dd, J=10.8, 5.2 Hz, 1H), 3.70 (dd, J=10.8, 5.3 Hz, 1H), 3.44 (m, 1H), 2.22 (br s, 3H); FDMS 195 (M+1). Anal. (C$_{10}$H$_{14}$N$_2$O$_2$) C, H, N.

N-Cyclopropylmethyl-L-serinamide (quantitative yield): $^1$H NMR (CDCl$_3$) δ7.47 (br s, 1H), 3.85 (dd, J=10.7, 5.1 Hz, 1H), 3.70 (dd, J=10.7, 6.0 Hz, 1H), 3.44 (t, J=5.5 Hz, 1H), 3.12 (ddd, J=18.4, 12.3, 5.4 Hz, 2H), 1.81 (br s, 3H), 0.95 (m, 1H), 0.51 (dt, J=7.5, 5.4 Hz, 2H), 0.21 (dt, J=5.2, 4.9 Hz, 2H); FDMS 159 (M+1).

N-Phenethyl-L-serinamide (10%): mp 108°–110° C.; $^1$H NMR (CDCl$_3$) δ7.43 (br s, 1H), 7.25 (m, 5H), 3.83 (dd, 1H), 3.64 (dd, 1H), 3.52 (dtd, 2H), 3.37 (dd, 1H), 2.82 (t, 2H), 1.62 (br s, 3H); FDMS 208 (M+). Anal. (C$_{11}$H$_{16}$N$_2$O$_2$), C, H, N.

N-((trans)-2-Phenylcyclopropyl)-L-serinamides (78%): mp 120° C.; $^1$H NMR (DMSO) δ8.11 (s, 1H), 7.22 (dd, 2H), 7.10 (m, 3H), 3.43 (m, 2H), 3.17 (br s, 1H), 2.80 (br s, 1H), 1.91 (m, 1H), 1.10 (m, 2H); FDMS 221 (M+1). 99.3% pure by HPLC.

N-[2-(Cyclohexyloxy)ethyl]-L-serinamide (66%): $^1$H NMR (CDCl$_3$) δ7.70 (br s, 1H), 3.83 (dd, J=10.8, 5.4 Hz, 1H), 3.72 (dd, J=10.8, 5.5 Hz, 1H), 3.54 (dd, J=5.3, 4.9 Hz, 2H), 3.45 (m, 3H), 3.26 (m, 1H), 2.37 (br s, 3H), 1.88 (m, 2H), 1.71 (m, 2H), 1.52 (m, 1H), 1.23 (m, 5H), 1.52 (br t, J=4.8, 1H), 1.24 (m, 4H); FDMS 231 (M+1). Anal. (C$_{11}$H$_{22}$N$_2$O$_3$·0.14CH$_2$Cl$_2$) C, H, N.

N-[3-(Cyclohexyloxy)propyl]-L-serinamide (77%) mp 66°–68° C.; $^1$H NMR (CDCl$_3$) δ7.79 (br s, 1H), 3.79 (dd, J=10.7, 5.5 Hz, 1H), 3.70 (dd, J=10.7, 5.5 Hz, 1H), 3.53 (t, J=5.8 Hz, 2H), 3.38 (m, 3H), 3.22 (m, 1H), 2.39 (br s, 3H), 1.89 (m, 2H), 1.74 (m, 3H); FDMS 245 (M+1). Anal. (C$_{12}$H$_{24}$N$_2$O$_3$) C, H, N.

N-[4-(Cyclohexyloxy)butyl]-L-serinamide (66%): $^1$H NMR (CDCl$_3$) δ7.54 (br t, 1H), 3.79 (dd, J=10.8, 5.5 Hz, 1H), 3.70 (dd, J=10.8, 5.2 Hz, 1H), 3.44 (br s, 3H), 3.26 (m, 2H), 3.19 (m, 1H), 2.52 (br s, 3H), 1.88 (m, 2H), 1.60 (m, 2H), 1.58 (m, 5H), 1.20 (m, 5H); FDMS 259 (M+1). Anal. (C$_{13}$H$_{26}$N$_2$O$_3$·0.45H$_2$O) C, H, N.

N-[3-([(cis) and (trans) ]-4-Methoxycyclohexyl)propyl]-L-serinamides (79%): $^1$H NMR (CDCl$_3$, cis-isomer only) δ7.49 (br t, 1H), 3.79 (dd, J=10.8, 5.6 Hz, 1H), 3.70 (dd, J=10.8, 5.3 Hz, 1H), 3.43 (dd, J=5.5, 5.4 Hz, 1H), 3.38 (br S, 1H), 3.28 (S, 3H), 3.20 (m, 2H), 2.48 (br s, 3H), 2.06–0.87 (m, 13H); FDMS 259 (M+1). Anal. (C$_{13}$H$_{26}$N$_2$O$_3$) C, H, N.

Example 1

A. 4-(tert-Butyldimethylsiloxy)benzyl alcohol

To a mixture of 28.0 g (0.20 mol) of 1,4-benzenedimethanol and 41.0 g (0.41 mol) of imidazole in ca. 850 mL of anhydrous CH$_2$Cl$_2$ at 0° C. was cannulated 30.5 g (0.20 mol) of TBSCl in 150 mL of anhydrous CH$_2$Cl$_2$ over 10–15 min period. The pale yellow solution was then stirred for 3 days. The reaction was quenched with 250 mL of cold 1N HCl. The organic layer was separated and washed with 250 mL of 1N HCl and saturated aqueous NaHCO$_3$ each. The aqueous layers were back-extracted with 2×500 mL of Et$_2$O. The combined organic layers were dried over MgSO$_4$ and concentrated. The residue was purified by preparative HPLC using 20% Et$_2$O-hexanes as eluent to afford 18.60 g (36.4%) of the colorless oil: $^1$H NMR (CDCl$_3$) δ7.32 (s, 4H), 4.74 (s, 2H), 4.67 (s, 2H), 1.69 (s, 1H), 0.95 (s, 9H), 0.095 (s, 6H); MS(EI) 195 (M- t-Bu). Anal. (C$_{14}$H$_{24}$O$_2$) C, H.

B. 4-(tert-Butyldimethylsiloxy)benzaldehyde

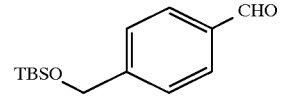

A mixture of 18.60 g (0.074 mol) of the benzylic alcohol and 74.4 g of MnO$_2$ in 500 mL of anhydrous THF was heated at 65°–70° C. (bath temperature) for 4 h. The reaction mixture was filtered through a pad of diatomaceous earth and the filtrate was concentrated to yield 15.33 g (83.1%) of the clean crude aldehyde: $^1$H NMR (CDCl$_3$) δ9.98 (s, 1H), 7.84 (d, J=8.0 Hz, 2H), 7.48 (d, J=8.0 Hz, 2H), 4.80 (s, 2H), 0.94 (s, 9H), 0.10 (s, 6H); FDMS 250 (M+). Anal. (C$_{14}$H$_{22}$O$_2$) C, H.

C. [4-[(tert-Butyldimethylsiloxy)methyl]phenyl]-(3-pyridyl)carbinol

To a solution of 10.64 g (67.3 mmol) of 3-bromopyridine in ca. 500 mL of anhydrous Et$_2$O at −78° C. was added 42 mL (67.3 mmol) of 1.6M BuLi in hexanes over 35 min period. After stirring 30 min, 15.33 g (61.2 mmol) of the benzaldehyde in 100 mL of anhydrous Et$_2$O was cannulated to the turbid lithiopyridine solution at −78° C. After the addition, the yellow mixture was stirred for 2 h at this temperature, and then the cold bath was removed and the mixture was stirred for another 30 min. The reaction was quenched with ca. 250 mL of brine and the organic layer was separated. The aqueous layer was extracted with 2×400 mL of CH$_2$Cl$_2$. The combined organic layer was dried over MgSO$_4$ and concentrated. Purification by preparative HPLC using 2% MeOH—CH$_2$Cl$_2$ afforded 17.99 g (89.2%) of the alcohol: $^1$H NMR (CDCl$_3$) δ8.61 (s, 1H), 8.46 (d, J=3.9 Hz, 1H), 7.74 (br d, J=7.8 Hz, 1H), 7.31 (s, 4H), 7.28 (m, 1H), 5.87 (s, 1H), 4.72 (s, 2H), 3.06 (br s, 1H), 0.93 (s, 9H), 0.087 (s, 6H); FDMS 329 (M$^+$).

D. 4-[(tert-Butyldimethylsiloxy)methyl]phenyl 3-pyridyl ketone

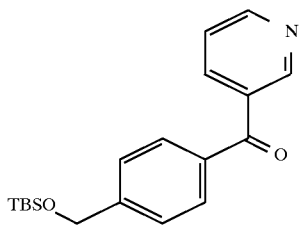

A mixture of 17.99 g (54.6 mmol) of the carbinol and 72 g of MnO$_2$ in 400 mL of THF was heated at 65° C. (bath temperature) overnight (15 h). The oxidant was removed by filtration through a pad of diatomaceous earth and washed with THF and EtOAc. The combined filtrate was concentrated to give 17.29 g (96.7%) of the clean crude ketone: $^1$H NMR (CDCl$_3$) δ8.97 (s, 1H), 8.79 (m, 1H), 8.09 (br d, J=7.9 Hz, 1H), 7.79 (d, J=8.2 Hz, 2H), 7.46 (d, J=8.4 Hz, 2H), 7.45 (buried 1H), 4.82 (s, 2H), 0.94 (s, 9H), 0.11 (s, 6H); FDMS 328 (M+1). Anal. (C$_{19}$H$_{25}$NO$_2$Si) H; C: calcd, 69.68; found, 69.02; N: cacld, 4.28; found, 4.79.

E. (E)- and (Z)-7-[4-[(tert-Butyldimethylsiloxy)-methyl]phenyl]-7-(3-pyridyl)hept-6-enoic Acid To a mixture of 6.55 g (20 mmol) of the ketone and 13.72 g (30 mmol) of (5-carboxypentyl)triphenylphosphonium bromide in 40 mL of THF at 0° C. was added dropwise 60.0 mL (60 mmol) of 1.0M t-BuOK in THF over 50 min period. The dark brown solution was stirred at 0°–5° C. for 2 h, and then the reaction was quenched with 50 mL of saturated aqueous NH$_4$Cl and 100 mL of brine. The mixture was extracted with 300–500 mL of EtOAc (4×). The dried extract (over MgSO$_4$) was concentrated and purified by preparative HPLC using EtOAc-AcOH-CH$_2$Cl$_2$ (25:1:74) as eluent to yield 8.01 g (94.1%) of a separable mixture of more polar E- and less polar Z-isomers (E/Z=1:4): $^1$H NMR (CDCl$_3$) δ (E-isomer): 8.60 (br s, 1H), 8.42 (br s, 1H), 7.46 (br d, J=8.0 Hz, 1H), 7.34 (d, J=10.0 Hz, 2H), 7.23 (m, 1H), 7.10 (d, J=8.0 Hz, 2H), 6.13 (t, J=7.4 Hz, 1H), 4.77 (s, 2H), 2.32 (dd, J=7.3, 7.1 Hz, 2H), 2.19 (ddd, J=7.3, 7.2, 7.2 Hz, 2H), 1.64 (m, 2H), 1.52 (m, 2H), 0.95 (s, 9H), 0.12 (s, 6H). (Z-isomer): 8.57 (d, J=4.6 Hz, 1H), 8.48 (s, 1H), 7.58 (d, J=7.9 Hz, 1H), 7.40 (dd, J=7.4, 7.4 Hz, 1H), 7.25 (d, J=8.5 Hz, 2H), 7.12 (d, J=8.2 Hz, 2H), 6.18 (t, J=7.6 Hz, 1H), 4.71 (s, 2H), 2.30 (dd, J=7.3, 7.1 Hz, 2H), 2.11 (ddd, 7.5, 7.3, 7.3 Hz, 2H), 1.66 (m, 2H), 1.53 (m, 2H), 0.92 (s, 9H), 0.082 (s, 6H); FDMS 426 (M+1). Anal. (C$_{25}$H$_{35}$NO$_3$) C, H, N.

F. Methyl (E)-and (Z)-7-[4-[(tert-butyldimethyl-siloxy)methyl]phenyl]-7-(3-pyridyl)hept-6-enoate

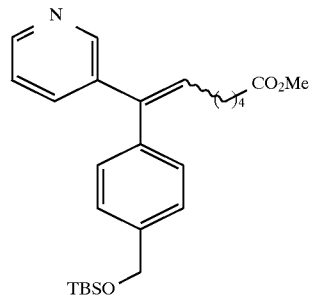

To a suspension of 2.08 g (6.4 mmol) of the ketone and 4.36 g (9.5 mmol) of (5-carboxypentyl)triphenylphosphonium bromide in 25 mL of THF at 10° C. was added 19.1 mL (19.1 mmol) of 1.0M t-BuOK in THF over 25 min period. The brown colored solution was further stirred at 10°–50° C. for 2 h and then kept in a refrigerator overnight. The reaction mixture was then treated with ca. 2.2 mL of 2.5N HCl to pH 6–7. The solvent was removed by evaporation and the residue was purified by preparative HPLC using EtOAc-AcOH-CH$_2$Cl$_2$ (25:0.5:74.5) as eluent. The Wittig product obtained was then dissolved in ca. 50 mL of THF and esterified (twice) with CH$_2$N$_2$ which was generated from a reaction of 1-methyl-3-nitro-1-nitrosoguanidine (3 g) and 5N NaOH (10 mL) in 50 mL of Et$_2$O. The crude reaction mixture was dried over MgSO$_4$, concentrated, and purified by preparative HPLC using 5% EtOAc-CH$_2$Cl$_2$ to afford 2.00 g (71.6%) of a separable mixture of more polar E- and less polar Z-isomers (E/Z=1:4).

G. Methyl (E)-7-[4-[(tert-Butyldimethylsiloxy)-methyl]phenyl]-7-(3-pyridyl)hept-6-enoate

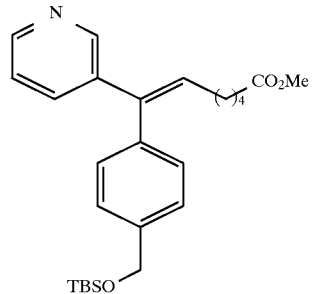

The (E)-heptenoic acid 4.329 g (10.2 mmol) was dissolved in ca. 200 mL of THF and cooled to 0° C. To this was added ethereal solution of CH$_2$N$_2$ which was generated from 2×(2.5 g of 1-methyl-3-nitro-1-nitrosoguanidine and 30 mL of 5N NaOH in 100 mL of Et$_2$O). The reaction was monitored by TLC. The ethereal solution was dried over MgSO$_4$, concentrated and purified by preparative HPLC using 5% EtOAc—CH$_2$Cl$_2$ to afford 2.98 g (66.6%) of the ester: $^1$H NMR (CDCl$_3$) δ8.51 (br s, 1H), 8.44 (br d, J=3.9 Hz, 1H), 7.46 (dt, J=8.0, 1.5 Hz, 1H), 7.33 (d, J=8.0 Hz, 2H), 7.18 (m, 1H), 7.10 (d, J=8.0 Hz, 2H), 6.08 (t, J=7.4 Hz, 1H), 4.77 (s, 2H), 3.65 (s, 3H), 2.27 (dd J=7.5, 7.2 Hz, 2H), 2.17 (dt, J=7.4, 7.3 Hz, 2H), 1.63 (m, 2H), 1.47 (m, 2H), 0.95 (s, 9H), 0.12 (s, 6H).

H. Methyl (E)-7-(4-Carboxyphenyl)-7-(3-pyridyl)-hept-6-enoate

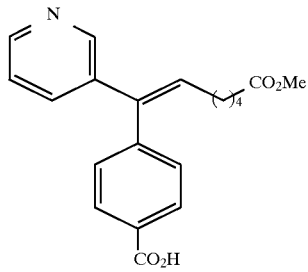

A solution of 462.4 mg (1.05 mmol) of the TBS ether in 10 mL of acetone at 0° C. was treated with 0.80 mL (2.1 mmol) of 2.67M Jones reagent for 6 h. After being kept in a refrigerator overnight, the reaction was quenched with 20 drops of i-PrOH at 0° C. while stirring for 30 min. The mixture was neutralized with 2.0 mL of 1N NaOH and 20 mL of saturated aqueous $NaHCO_3$ to pH 7, diluted with acetone to ca. 100 mL, and filtered. The solid portion was resuspended in a small amount of $H_2O$ and saturated aqueous $NaHCO_3$, diluted with ca. 50 mL of acetone and stirred. This was filtered and the filtrates were combined and concentrated. Flash chromatography with MeOH—AcOH—$CH_2Cl_2$ (3:1:96) afforded 305.0 mg (85.4%) of the desired acid: $^1$H NMR ($CDCl_3$) δ8.53 (br s, 2H), 8.13 (d, J=7.8 Hz, 2H), 7.49 (br d, J=7.7 Hz, 1H), 7.24 (d, J=7.4 Hz, 2H), 6.18 (t, J=7.4 Hz, 1H), 3.65 (s, 3H), 2.27 (dd, J=7.3, 7.1 Hz, 2H), 2.16 (distorted ddd J=7.2, 7.1, 6.9 Hz, 2H), 1.65–1.44 (m, 4H); FDMS 340 (M+1).

I. N-(4-Cyclohexylbutyl)-O-(tert-butyldimethyl-silyl)-L-serinamide

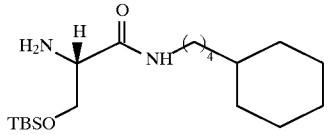

To a mixture of 4.18 g (17.2 mmol) of N-(4-cyclohexylbutyl)-L-serinamide and 3.84g (37.9 mmol) of imidazole in 70 mL of anhydrous $CH_2Cl_2$ was added 2.86 g (19.0 nmmol) of TBSCl at room temperature and the reaction mixture was stirred for 100 min. The mixture was then taken up in ca. 200 mL of $CH_2Cl_2$ and washed with 100 mL of saturated aqueous $NH_4Cl$ which was back-extracted with 2×200 mL of $CH_2Cl_2$. The combined organic layer was dried over $MgSO_4$, concentrated and purified by preparative HPLC using 50% EtOAc—$CH_2Cl_2$ as eluent to give 4.29 g (69.8%) of the desired TBS ether: $^1$H NMR ($CDCl_3$) δ7.32 (br s, 1H), 3.77 (m, 2H), 3.41 (t, J=5.3 Hz, 1H), 3.21 (dtd, J=7.0, 6.2, 2.6 Hz, 2H), 1.68–1.08 (m, 17H), 0.87 (s, 9H), 0.051 (s, 3H), 0.045 (S, 3H); FDMS 357 (M+1).

J. Methyl (1S)-(E)-7-[4-[[[2-[(4-Cyclohexylbutyl)-amino]-1-hydroxymethyl-2-oxoethyl]amino] carbonyl]-phenyl]-7-(3-pyridyl)hept-6-enoate

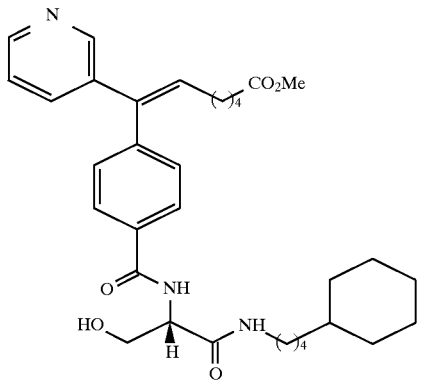

To a mixture of 507.6 mg (1.5 mmol) of the acid, 539 mg (1.5 mmol) of the serinamide, and 202.1 mg of HOBT in 5.0 mL of THF was added 308.6 mg (1.5 mmol) of DCC in one portion at 0° C. The mixture was stirred at 0° C. for 70 min and at room temperature for 22.5 h. This was then diluted with EtOAc to 50–60 mL and filtered. The filtrate was concentrated and purified by preparative HPLC using 2.5% MeOH—$CH_2Cl_2$ to afford 685.5 mg of the bisamide TBS ether. The ether was dissolved in 3.0 mL of THF and treated with 1.5 mL of 1.0M $Bu_4N^+F^-$ at room temperature for 3 h. The reaction was quenched with ca. 25 mL of saturated aqueous $NH_4Cl$ and extracted with 3×50 mL of EtOAc. The combined extract was dried over $MgSO_4$, concentrated, and purified by flash chromatography using 3–5% MeOH—$CH_2Cl_2$ to give 411.4 mg of the free alcohol (48.8%): $^1$H NMR ($CDCl_3$) δ8.45 (m, 2H), 7.83 (d, J=8.1 Hz, 2H), 7.48 (d, J=7.0 Hz, 1H), 7.39 (dd, J=8.0, 1.6 Hz, 1H), 7.22 (d, J=8.1 Hz, 2H), 7.15 (m, 2H), 6.14 (t, J=7.5 Hz, 1H), 4.65 (distorted q, J=~4.5 Hz, 1H), 4.19 (dd J=11.3, 3.5 Hz, 1H), 3.73 (dd, J=11.3, 5.4 Hz, 1H), 3.63 (s, 3H), 3.25 (ddd, J=6.8, 6.7, 6.3 Hz, 2H), 2.25 (dd, J=7.4, 7.1 Hz, 2H), 2.14 (dt, J=7.4, 7.3 Hz, 2H), 1.64–0.78 (m, 21H); FDMS 564 (M+1).

K. Methyl (4S)-(E)-7-[4-[4-[[(4-Cyclohexylbutyl)-amino]carbonyl]-4,5-dihydro-2-oxazolyl]phenyl]-7-(3-pyridyl) hept-6-enoate

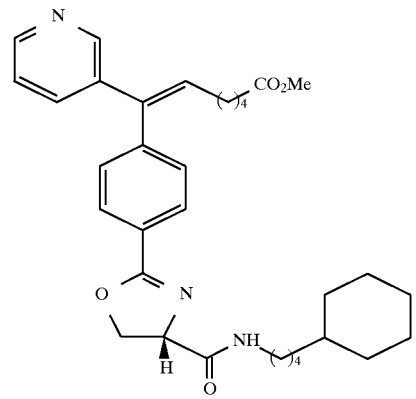

A mixture of 97.0 mg (0.17 mmol) of the hydroxybisamide, 135.4 mg (0.52 mmol) of $PPh_3$, 90 mL (0.52 mmol) of diisopropylethylamine, and 50 mL (0.52 mmol) of $CCl_4$ in 1.7 inmL of $CH_3CN$ was stirred at room temperature for 7 h. The solvent was removed and the residue was purified by flash chromatography eluting with EtOAc—AcOH—$CH_2Cl_2$ (68:2:30) to afford 76.1 mg (81.0%) of the oxazoline: $^1$H NMR ($CDCl_3$) δ8.47 (br s, 2H), 7.98 (d, J=7.7 Hz, 2H), 7.41 (br d, J=7.5 Hz, 1H), 7.22

(d, J=7.8 Hz, 2H), 7.19 (m, 1H), 6.68 (br s, 1H), 6.13 (t, J=7.2 Hz, 1H), 4.84 (br dd, J=9.7, 9.7 Hz, 1H), 4.73–4.58 (m, 2H), 3.64 (s, 1H), 3.36–3.17 (m, 2H), 2.26 (dd, J=7.1, 6.7 Hz, 2H), 2.11 (distorted ddd J=7.1, 7.0, 6.4 Hz, 2H), 1.65–0.80 (m, 21H); FDMS 545 (M$^+$).

L. (4S)-(E)-7-[4-[4-[[(4-Cyclohexylbutyl)-amino]carbonyl]-4,5-dihydro-2-oxazolyl]phenyl]-7-(3-pyridyl)hept-6-enoic Acid

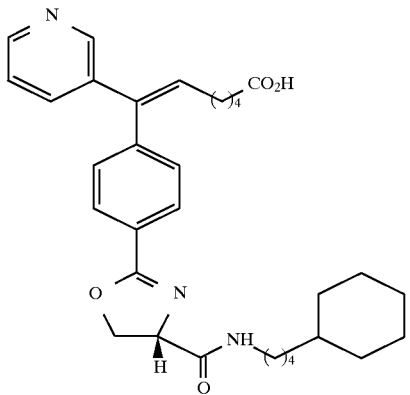

A solution of 22.0 mg (0.040 mmol) of the ester in 320 mL of THF-MeOH (1:1) was treated with 160 mL (0.16 mmol) of 1N NaOH at room temperature for 3.5 h. The reaction mixture was then neutralized with 160 mL of 1N HCl, concentrated, and purified by flash chromatography with MeOH—AcOH—$CH_2Cl_2$ (3:0.5:96.5) to give 15.3 mg (71.4%) of the free acid. $[\alpha]_D$ +1.60 (c 1.0, MeOH): mp 65°–70° C.; $^1$H NMR (CDCl$_3$) δ8.55 (s, 1H), 8.45 (d, J=3.3 Hz, 1H), 7.98 (d, J=8.1 Hz, 2H), 7.42 (d, J=8.0 Hz, 1H), 7.22 (d, J=8.2 Hz, 2H), 7.20 (buried, 1H), 6.80 (t, J=5.8 Hz, 1H), 6.18 (t, J=7.4 Hz, 1H), 4.86 (dd, J=9.6, 9.5 Hz, 1H), 4.66 (m, 2H), 3.35–3.17 (m, 2H), 2.31 (dd, J=7.2, 6.8 Hz, 2H), 2.17 (ddd, J=7.3, 7.2, 7.0 Hz, 2H), 1.65–0.79 (m, 21H); FDMS 532 (M+1). Anal. ($C_{32}H_{41}N_3O_4$) C, H, N.

Example 2
A. Methyl (E)-7-[4-[4-[[(4-Cyclohexylbutyl)-amino]carbonyl]-2-oxazolyl]phenyl]-7-(3-pyridyl)hept-6-enoate

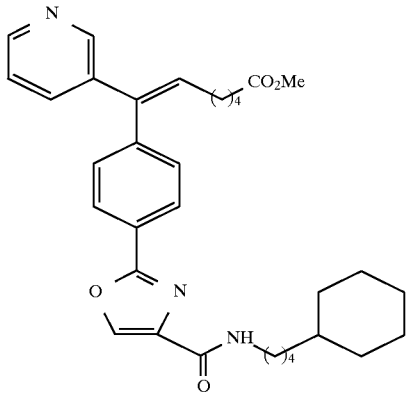

A mixture of 53.3 mg (0.098 mmol) of the oxazoline of Example 1-K, 217.6 mg of $NiO_2$, and several pellets of 4Å molecular sieves in 1.5 mL of benzene-1,4-dioxane (4:1) was heated at reflux for 8 h and stirred at room temperature overnight. Another 106 mg of $NiO_2$ (making the total 6×wt of the oxazoline) and several pellets of 4 Å molecular sieves were added and the mixture was heated at reflux for 2 h. The mixture was diluted with benzene-THF to ~10 mL and filtered through a pad of diatomaceous earth with thorough rinsing with benzene and THF. The combined filtrate was concentrated and purified by flash chromatography, eluting with EtOAc-AcOH—$CH_2Cl_2$ (50:3:47) to yield 14.3 mg (26.3%) of the oxazole: $^1$H NMR (CDCl$_3$) δ8.48 (br s, 2H), 8.23 (s, 1H), 8.05 (d, J=8.0 Hz, 2H), 7.45 (d, J=7.9 Hz, 1H), 7.27 (d, J=7.9 Hz, 2H), 7.19 (m, 1H), 7.05 (t, J=5.7 Hz, 1H), 6.14 (t, J=7.4 Hz, 1H), 3.64 (s, 3H), 3.43 (dt, J=6.7, 6.7 Hz, 2H), 2.26 (dd, J=7.4, 7.1 Hz, 2H), 2.17 (ddd, J=7.4, 7.3, 7.3 Hz, 2H), 1.69–0.83 (m, 21H); FDMS 543 (M$^+$).

B. (E)-7-[4-[4-[[(4-Cyclohexylbutyl)amino]carbonyl]-2-oxazolyl]phenyl]-7-(3-pyridyl)hept-6-enoic Acid

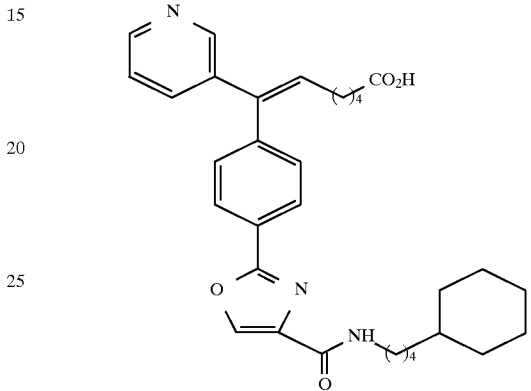

A solution of 14.3 mg (0.026 mmol) of the ester in 200 mL of MeOH—THF (1:1) was treated with 100 mL of 1N NaOH at room temperature for 4 h. The mixture was then neutralized with 100 mL of 1N HCl and concentrated. The residue was flash chromatographed with EtOAc—AcOH—$CH_2Cl_2$ (57:3:40) to afford 11.1 mg (79.7%) of the title acid: (the product of an alternative preparation is more fully characterized below following Example 24) mp 52°–56° C.; FDMS 530 (M+1).

Example 3
(4S)-(Z)-7-[4-[4-[[(4-Cyclohexylbutyl)amino]carbonyl]-4,5-dihydro-2-oxazolyl]phenyl]-7-(3-pyridyl)hept-6-enoic Acid Using the separated (Z)-heptenoic acid described in Example 1-E and procedures similar to those described in Examples 1-I through 1-L, the title compound was prepared: FDMS 532 (M+1).

Example 4
(Z)-7-[4-[4-[[(4-Cyclohexylbutyl)amino]carbonyl]-2-oxazolyl]phenyl]-7-(3-pyridyl)hept-6-enoic Acid Using the separated (Z)-heptenoic acid described in Example 1-E and procedures similar to those described in Examples 1-I through 1-K and Example 2, the title compound was prepared: mp 61°–64° C.; $^1$H NMR (CDCl$_3$) δ8.59 (br s, 1H), 8.47 (br d, J=1.0 Hz, 1H), 8.22 (s, 1H), 7.91 (d, J=8.3 Hz, 2H), 7.52 (d, J=7.6 Hz, 1H), 7.37 (m, 1H), 7.26 (d, J=8.2 Hz, 2H), 7.07 (br t, J=5.7 Hz, 1H), 6.29 (t, J=7.5 Hz, 1H), 3.42 (ddd, J=6.8 6.7, 6.6 Hz, 2H), 2.30 (br s, 2H), 2.14 (dt, J=7.0, 7.0 Hz, 2H), 1.69–0.82 (m, 21H); FDMS 530 (M+1). Anal. ($C_{32}H_{39}N_3O_4$) C, H, N.

Examples 5–11

Using similar procedures to those described in Examples 1–4, but starting from 1,2-benzenedimethanol (for Examples 5–8) or 1,3-benzenedimethanol (for Examples 9–11), the following compounds of Formula I were prepared.

Example 5
(4S)-(E)-7-[2-[4-[[(4-Cyclohexylbutyl)-amino]carbonyl]-4,5-dihydro-2-oxazolyl]phenyl]-7-(3-pyridyl)hept-6-enoic Acid: $^1$H NMR (CDCl$_3$) δ8.41 (br s, 2H), 7.61 (d, J=7.2 Hz, 1H), 7.43 (d, J=7.3 Hz, 2H), 7.34–7.21 (m, 3H), 6.68 (t, J=5.7 Hz, 1H), 5.84 (t, J=7.4 Hz, 1H), 4.51 (dd, J=11.3, 8.0 Hz, 1H), 4.34 (m, 2H), 3.22 (m, 1H), 3.09 (m, 1H), 2.27 (m, 4H), 1.63–0.77 (m, 21H); FDMS 532 (M+1). Anal. (C$_{32}$H$_{41}$N$_3$O$_4$) C, H, N.

Example 6
(4S)-(Z)-7-[2-[4-[[(4-Cyclohexylbutyl)-amino]carbonyl]-4,5-dihydro-2-oxazolyl]phenyl]-7-(3-pyridyl)hept-6-enoic Acid: $^1$H NMR (CDCl$_3$) δ8.51 (br s, 1H), 8.39 (d, J=4.2 Hz, 1H), 7.88 (m, 1H), 7.52 (dd, J=7.3, 7.3 Hz, 1H), 7.42 (br d, J=7.3 Hz, 1H), 7.40 (br d, J=7.2 Hz, 1H), 7.18 (m, 2H), 6.46 (br s, 1H), 6.15 (br s, 1H), 4.61 (distorted dd J=~11.1, 9.2 Hz, 1H), 4.37 (m, 2H), 3.21–2.98 (m, 2H), 2.23 (dd, J=7.2, 7.0 Hz, 2H), 1.96 (br s, 2H), 1.65–0.75 (m, 21H); FDMS 532 (M+1). Anal. (C$_{32}$H$_{41}$N$_3$O$_4$), C, H, N.

Example 7
(E)-7-[2-[4-[[(4-Cyclohexylbutyl)-amino]carbonyl]-2-oxazolyl]phenyl]-7-(3-pyridyl)hept-6-enoic Acid: $^1$H NMR (CDCl$_3$) δ10.4 (br s, 1H), 8.43 (s, 1H), 8.40 (br d, J=3.3 Hz, 1H), 8.13 (s, 1H), 7.78 (d, J=7.7 Hz, 1H), 7.44 (m, 3H), 7.33 (d, J=7.4 Hz, 1H), 7.19 (dd, J=7.4, 5.0 Hz, 1H), 6.94 (t, J=5.8 Hz, 1H), 5.78 (t, J=7.4 Hz, 1H), 3.38 (dt, J=6.8, 6.7 Hz, 2H), 2.27 (m, 4H), 1.68–0.82 (m, 21H); FDMS 530 (M+1). Anal. (C$_{32}$H$_{39}$N$_3$O$_4$· 0.6C$_2$H$_4$O$_2$) C, H, N.

Example 8
(Z)-7-[2-[4-[[(4-Cyclohexylbutyl)-amino]carbonyl]-2-oxazolyl]phenyl]-7-(3-pyridyl)hept-6-enoic Acid: $^1$H NMR (CDCl$_3$) δ8.56 (brδJ=1.5 Hz, 1H), 8.40 (br d, J=1.7 Hz, 1H), 8.09 (s, 1H), 8.05 (d, J=7.5 Hz, 2H), 7.57–7.43 (m, 3H), 7.27 (d, J=7.6 Hz, 1H), 7.16 (br s, 1H), 6.80 (t, J=5.2 Hz, 1H), 6.21 (t, J=7.3 Hz, 1H), 3.35 (dt, J=6.6, 6.5 Hz, 2H), 2.21 (dd, J=7.1, 6.9 Hz, 2H), 1.94 (m, 2H), 1.69–0.82 (m, 21H); FDMS 530 (M+1). Anal. (C$_{32}$H$_{39}$N$_3$O$_4$) C, H, N.

Example 9
(4S)-(Z)-7-[3-[4-[[(4-Cyclohexylbutyl)-amino]carbonyl]-4,5-dihydro-2-oxazolyl]phenyl]-7-(3-pyridyl)hept-6-enoic Acid: $^1$H NMR (CDCl$_3$) δ8.58 (br s, 1H), 8.48 (s, 1H), 7.87 (s, 1H), 7.83 (d, J=7.6 Hz, 1H), 7.50 (d, J=7.7 Hz, 1H), 7.32 (m, 2H), 7.23 (d, J=7.9 Hz, 1H), 6.84 (t, J=5.7 Hz, 1H), 6.23 (t, J=7.5 Hz, 1H), 4.83 (dd, J=9.6, 9.3 Hz, 1H), 4.65 (distorted d, J=9.5 Hz, 2H), 3.25 (m, 2H), 2.31 (dd, J=7.0, 6.4 Hz, 2H), 2.16 (ddd, J=7.4, 7.2, 7.1 Hz, 2H), 1.66–0.79 (m, 21H); FDMS 532 (M+1). Anal. (C$_{32}$H$_{41}$N$_3$O$_4$) C, H, N.

Example 10
(E)-7-[3-[4-[[(4-Cyclohexylbutyl)-amino]carbonyl]-2-oxazolyl]phenyl]-7- (3-pyridyl)hept-6-enoic Acid: $^1$H NMR (CDCl$_3$) δ8.95 (br s, 1H), 8.56 (br s, 1H), 8.43 (br s, 1H), 8.25 (s. 1H), 7.99 (d, J=7.9 Hz, 1H), 7.83 (s, 1H), 7.49 (m, 2H), 7.25 (m, 2H), 7.14 (t, J=6.0 Hz, 1H), 6.20 (t, J=7.4 Hz, 1H), 3.41 (ddd, J=6.9, 6.9, 6.6 Hz, 2H), 2.31 (dd, J=7.1, 6.8 Hz, 2H), 2.19 (ddd, J=7.4, 7.2, 7.0 Hz, 2H), 1.68–0.81 (m, 21H); FDMS 530 (M+1). 95.3% purity by HPLC analysis.

Example 11
(Z)-7-[3-[4-[[(4-Cyclohexylbutyl)-amino]carbonyl]-2-oxazolyl]phenyl]-7-(3-pyridyl)hept-6-enoic Acid: $^1$H NMR (CDCl$_3$) δ8.60 (br s, 1H), 8.59 (s, 1H), 8.23 (s, 1H), 7.89 (m, 2H), 7.53 (d, J=7.8 Hz, 1H), 7.38 (d, J=7.6 Hz, 1H), 7.36 (d, J=7.6 Hz, 1H:), 7.23 (d, J=8.0 Hz, 1H), 7.07 (t, J=5.9 Hz, 1H), 6.26 (t, J=7.5 Hz, 1H), 3.42 (ddd J=7.0, 6.7, 6.6 Hz, 2H), 2.32 (dd, J=7.1, 6.9 Hz, 2H), 2.17 (ddd, J=7.3, 7.1, 7.1 Hz, 2H), 1.69–0.83 (m, 21H); FDMS 530 (M+1). Anal. (C$_{32}$H$_{39}$N$_3$O$_4$· 0.2C$_2$H$_4$O$_2$), C, H, N.

Examples 12–17
The following compounds of Formula I were prepared from the (E)-acid of Example 1-H using similar procedures to those of Example 1 and Example 2, except using the corresponding serinamide.

Example 12
(4S)-(E)-7-[4-[4,5-Dihydro-4-(pentyl-amino) carbonyl-2-oxazolyl]phenyl]-7-(3-pyridyl)hept-6-enoic Acid: $^1$H NMR (CDCl$_3$) δ8.61 (br s, 1H), 8.46 (br s, 1H), 8.00 (d, J=8.1 Hz, 2H), 7.54 (d, J=7.8 Hz, 1H), 7.32 (m, 1H), 7.23 (d, J=~8.1 Hz, 2H), 6.80 (t, J=5.5 Hz, 1H), 6.23 (t, J=7.4 Hz, 1H), 4.87 (dd, J=9.7, 9.6 Hz, 1H), 4.68 (m, 2H), 3.33 (m, 1H), 3.21 (m, 1H), 2.32 (dd, J=7.1, 6.8 Hz, 2H), 2.18 (ddd, J=7.2, 7.1, 6.8 Hz, 2H), 1.69–1.41 (m, 6H), 1.30 (m, 4H), 0.87 (t, J=6.9 Hz, 3H); FDMS 463 (M+)

Example 13
(E)-7-[4-[4-(Pentylamino)carbonyl-2-oxazolyl]phenyl]-7-(3-pyridyl)hept-6-enoic Acid: mp 55°–58° C.; $^1$H NMR (CDCl$_3$)δ6 8.61 (s, 1H), 8.51 (d, J=4.3 Hz, 1H), 8.26 (S, 1H), 8.07 (d, J=8.2 Hz, 2H), 7.65 (d, J=8.0 Hz, 1H), 7.39 (m, 1H), 7.27 (d, J=8.2 Hz, 2H), 7.07 (t, J=5.9 Hz, 1H), 6.26 (t, J=7.4 Hz, 1H), 3.45 (dt, J=6.8, 6.7 Hz, 2H), 2.32 (dd, J=7.0, 6.9 Hz, 2H), 2.21 (ddd, J=7.3, 7.2, 7.0 Hz, 2H), 1.67–1.52 (m, 6H), 1.40–1.35 (m, 4H), 0.91 (t, J=6.9 Hz, 3H); FDMS 462 (M+1). Anal. (C$_{27}$H$_{31}$N$_3$O$_4$), C, H, N.

Example 14
(4S)-(E)-7-[4-[4-[[(Cyclopropylmethyl)-aminolcarbonyl]-4,5-dihydro-2-oxazolyl]phenyl]-7-(3-pyridyl)hept-6-enoic Acid: $^1$H NMR (CDCl$_3$) δ8.53 (br s, 1H), 8.46 (br s, 1H), 7.99 (d, J=8.2 Hz, 2H), 7.46 (dd, J=8.1, 1.2 Hz, 1H), 7.22 (d, J=8.2 Hz, 2H), 7.22 (buried, 1H), 6.95 (t, J=5.6 Hz, 1H), 6.18 (t, J=7.5 Hz, 1H), 4.88 (dd, J=9.6, 9.5 Hz, 1H), 4.68 (m, 2H), 3.19 (m, 1H), 3.07 (m, 1H), 2.30 (dd, J=7.2, 6.9 Hz, 2H), 2.17 (ddd, J=7.3, 7.2, 7.0 Hz, 2H), 1.66–1.49 (m, 4H), 0.96 (m, 1H), 0.49 (dd, J=8.0, 1.0 Hz, 2H), 0.20 (br d, J=4.6 Hz, 2H); FDMS 448 (M+1). Anal. (C$_{26}$H$_{29}$N$_3$O$_4$) C, H, N.

Example 15
(E)-7-[4-[4-[1(Cyclopropylmethyl)amino]-carbonyl]-2-oxazolyl]phenyl]-7- (3-pyridyl)hept-6-enoic Acid: mp 69°–70° C.; $^1$H NMR (CDCl$_3$) δ8.55 (s, 1H), 8.47 (d, J=3.8 Hz, 1H), 8.27 (s, 1H), 8.05 (d, J=8.1 Hz, 2H), 7.47 (d, J=8.0 Hz, 1H), 7.26 (d, J=8.0 Hz, 2H), 7.22 (m, 2H), 6.18 (t, J=7.4 Hz, 1H), 3.30 (dd, J=6.4, 6.3 Hz, 2H), 2.31 (dd, J=7.2, 6.8 Hz, 2H), 2.19 (ddd, J=7.3, 7.1, 7.0 Hz, 2H), 1.67–1.50 (m, 4H), 1.06 (m, 1H), 0.55 (ddd, J=7.4, 5.5, 5.3 Hz, 2H), 0.28 (ddd, J=5.0, 4.9, 4.8 Hz, 2H); FDMS 446 (M+1). Anal. (C$_{26}$H$_{27}$N$_3$O$_4$· 0.4C$_2$H$_4$O$_2$) C, H, N.

Example 16
(4S)-(E)-7-[4-[4-(Benzylamino)carbonyl-4,5-dihydro-2-oxazolyl]phenyl]-7-(3-pyridyl)hept-6-enoic Acid: mp 61°–66° C.; $^1$H NMR (CDCl$_3$) δ8.57 (s, 1H), 8.46 (br d, J=2.0 Hz, 1H), 7.96 (d, J=8.1 Hz, 2H), 7.48 (d, J=8.1 Hz, 1H), 7.35–7.15 (m, 7H), 7.20 (d, J=8.2 Hz, 2H), 6.20 (t, J=7.5 Hz, 1H), 4.93 (dd, J=9.8, 9.7 Hz, 1H), 4.71 (m, 2H), 4.57 (dd, J=14.9, 6.3 Hz, 1H), 4.40 (dd, J=14.8, 5.6 Hz, 1H), 2.29 (dd, J=7.1, 6.8 Hz, 2H), 2.16 (ddd, J=7.3, 7.2, 7.1 Hz, 2H), 1.64–1.48 (m, 4H); FDMS 484 (M+1). Anal. (C$_{29}$H$_{29}$N$_3$O$_4$) C, H, N.

Example 17
(E)-7-[4-[4-(Benzylamino)carbonyl]-2-oxazolyl]phenyl]-7-(3-pyridyl)hept-6-enoic Acid:

mp 57°–62° C.; $^1$H NMR (CDCl$_3$) δ 8.57 (s, 1H), 8.46 (d, J=4.2 Hz, 1H), 8.30 (s, 1H), 8.02 (d, J=8.1 Hz, 2H), 7.47–7.21 (m, 10H), 6.19 (t, J=7.4 Hz, 1H), 4.65 (d, J=5.9 Hz, 2H), 2.31 (dd, J=7.1, 6.8 Hz, 2H), 2.18 (ddd, J=7.3, 7.1, 7.0 Hz, 2H), 1.66–1.50 (m, 4H); FDMS 482 (M+1). Anal. (C$_{29}$H$_{27}$N$_3$O$_4$) C, H, N.

Examples 18–24 and Alternative Preparation of Example 2

A. Methyl 4-[Hydroxy(3-pyridyl)methyl]benzoate

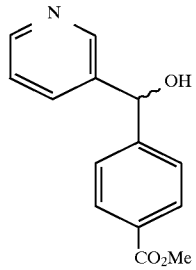

To a cooled solution (−78° C.) of 10.6 mL (0.11 mol) of 3-bromopyridine in 1.2 L of anhydrous Et$_2$O was added dropwise 93.8 mL (0.15 mol) of 1.6M n-BuLi in hexanes over 1 h period. The turbid yellow solution was stirred at −78° C. for 25 min, and then 24.62 g (0.15 mol) of methyl 4-formylbenzoate in 300 mL of Et$_2$O was cannulated to the lithiopyridine solution. The mixture was continually stirred at −78° C. for 2 h and at room temperature for 2 more h. The reaction was quenched with 400 mL of brine and 200 mL of H$_2$O. The organic layer was separated and the aqueous layer was extracted with 3×1.0 L of CH$_2$Cl$_2$. To the combined organic layer was added 200 mL of MeOH to dissolve the product which precipitated out. This was then dried over MgSO$_4$ and concentrated. The crude product was crystallized from MeOH to afford 17.24 g (64%) of a white solid: mp 151° C.; $^1$H NMR (CDCl$_3$) δ 8.62 (br s, 1H), 8.51 (br s, 1H), 8.02 (d, J=8.3 Hz, 2H), 7.70 (d, J=7.9 Hz, 1H), 7.45 (d, J=8.3 Hz, 2H), 7.30 (br s, 1H), 5.93 (s, 1H), 3.90 (s, 3H), 2.92 (br s, 1H); FDMS 244 (M+1). Anal. (C$_{14}$H$_{13}$NO$_3$ · 0.16C$_2$H$_4$O) C, H, N.

B. Methyl 4-(3-Pyridylcarbonyl)benzoate

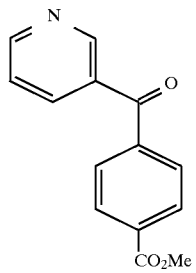

A suspension of 9.34 g (4× by weight) of MnO$_2$ and 2.34 g (9.6 mmol) of the carbinol in 100 mL of THF was heated at 70° C. (bath temperature) overnight (17 h). The mixture was filtered through a pad of diatomaceous earth with THF wash. The filtrate was concentrated to yield 1.86 g (81%) of a yellow fluffy solid which was clean by $^1$H NMR: mp 144°–146° C.; $^1$H NMR (CDCl$_3$) δ 9.00 (br s, 1H), 8.84 (br s, 1H), 8.17 (d, J=8.4 Hz, 2H), 8.14 (dd, J=~8.6, 1.3 Hz, 1H), 7.85 (d, J=8.3 Hz, 2H), 7.49 (dd, J=7.6, 5.0 Hz, 1H), 3.97 (s, 3H); FDMS 241 (M+). Anal. (C$_{14}$H$_{11}$NO$_3$ · 0.1C$_4$H$_8$O$_2$) C, H, N.

C. 4-(3-Pyridylcarbonyl)benzoic Acid

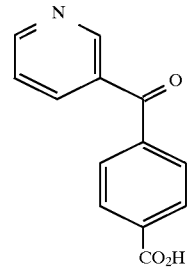

XXXIIIa

To a solution of 9.03 g (37.4 mmol) of the benzoate ester in 150 mL of THF-MeOH (1:1) was added 56.2 mL (56.2 mmol) of 1N NaOH at 0° C. After 5 min, the ice bath was removed and the turbid solution was stirred at room temperature for 2 h. The mixture was then neutralized with 56.2 mL (56.2 mmol) of 1N HCl and concentrated to dryness. After drying over P$_2$O$_5$ under vacuum overnight, the crude product (containing 27.8% NaCl by weight) was used in the next reaction without further purification (Note: The acid does not dissolve well in conventional solvents such as MeOH and CH$_2$Cl$_2$, which made the purification difficult. Initially the acid was purified by flash chromatography using MeOH-AcOH-CH$_2$Cl$_2$ (5:1:94) which resulted in low yield. It was found that NaCl did not interfere the amide coupling in the next step; thus, no further purification was necessary for the hydrolysis product): mp 266°–267° C.; $^1$H NMR (DMSO) δ 13.31 (d, J=1.3 Hz, 1H), 8.86; (s, 1H), 8.81 (dd, J=4.9, 1.0 Hz, 1H), 8.11 (m, 1H), 8.07 (d, J=8.3 Hz, 2H), 7.84 (d, J=8.2 Hz, 2H), 7.58 (dd, J=7.9, 4.9 Hz, 1H); FDMS 227 (M+). Anal. (C$_{13}$H$_9$NO$_3$) C, H, N.

D. Compounds of Formula (L)-XXXIVa in which R has the indicated value were prepared from the compound of Formula XXXIIIa and the corresponding serinamides as described below.

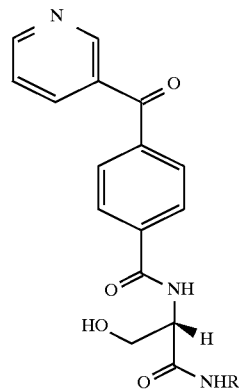

(L)-XXXIVa

Example 18-D
[4-(3-Pyridylcarbonyl)benzoyl]-N-phenethyl-L-serinamide:

To a cooled (1° C.) mixture of 423.8 mg (1.86 mmol) of 4-(3-pyridylcarbonyl)benzoic acid, 388.4 mg (1.86 mmol) of N-phenethyl-L-serinamide, and 252.0 mg (1.86 mmol) of HOBT was added 0.21 mL (1.86 mmol) of NMM and 357.5 mg (1.86 mmol) of WSC. After 1 h stirring at 0° C., the ice bath was removed and the reaction mixture was stirred at room temperature for 2 h. The reaction was quenched with 30 mL of H$_2$O and the mixture was extracted with 3×100 mL of EtOAc. The combined aqueous layer was back extracted with 100 mL of EtOAc and the combined organic layer was in turn washed with 100 mL of brine. The organic layer was dried over MgSO$_4$, concentrated and purified by flash chromatography using MeOH-AcOH-CH₂Cl₂ (4:1:95) to yield 645.6 mg (83%) of the bisamide: mp 85°–90° C.; ¹H NMR (CDCl₃) δ 8.85 (s, 1H), 8.71 (br s, J=3.8 Hz, 1H), 8.18 (d, J=7.3 Hz, 1H), 8.03 (d, J=7.9 Hz, 1H), 7.88 (d, J=8.1 Hz, 2H), 7.69 (d, J=7.9 Hz, 3H), 7.40 (dd, J=7.7, 5.0 Hz, 1H), 7.08 (m, 5H), 4.83 (m, 1H), 3.98 (m, 1H), 3.83 (m, 1H), 3.42 (m, 2H), 2.72 (t, J=7.0 Hz, 2H), 1.94 (s, 1H); FDMS 417 (M+). Anal. ($C_{24}H_{23}N_3O_4 \cdot 0.33C_2H_4O_2$), C, H, N.

Example 19-D and 20-D
[4-(3-Pyridylcarbonyl)benzoyl]-N-(trans-2-phenylcyclopropyl)-L-serinamides:

Prepared as above from 3.00 g (13.6 mmol) of N-(trans-2-phenylcyclopropyl)-L-serinamides (99%): ¹H NMR (CDCl₃, mixture) δ 8.93 (s, 1H), 8.80 (br d, J=4.0, 1H), 8.08 (m, 2H), 7.95 (d, J=8.2 Hz, 2H), 7.86 (d, J=7.6 Hz, 1H), 7.76 (d, J=8.0 Hz, 2H), 7.47 (dd, J=7.8, 5.0 Hz, 1H), 7.22–7.08 (m, 3H), 7.03 (br d, J=7.1 Hz, 2H0, 4.84 ( br dt, J=6.9, 5.3 Hz, 1H), 4.08 (dd, J=11.3, 4.7 Hz, 1H), 3.85 (dd, J=11.3, 5.6 Hz, 1H), 2.89 (m, 1H), 2.06 (m, 1H), 1.17 (dd, J=7.6, 6.4 Hz, 2H); FDMS 429 (M+). Anal. ($C_{25}H_{23}N_3O_4 \cdot 0.32C_2H_4O_2$) C, H, N.

Example 21-D
[4-(3-Pyridylcarbonyl)benzoyl]-N-[2-(cyclohexyloxy) ethyl]-L-serinamide:

As above from 1.052 g (4.9 mmol) of N-(2-(cyclohexyloxy)ethyl)-L-serinamide (78%): 53°–58° C.; ¹H NMR (CDCl₃) δ 9.00 (s, 1H), 8.86 (br d, J=3.1 Hz, 1H), 8.16 (dt, J=7.9, 1.6 Hz, 1H), 7.99 (d, J=8.3 Hz, 2H), 7.88 (d, J=8.3 Hz, 2H), 7.53 (m, 2H), 7.12 (distorted br d, J=5.2 Hz, 1H), 4.69 (m, 1H), 4.23 (dd, J=11.4, 3.4 Hz, 1H), 3.78 (dd, J=11.4, 5.3 Hz, 1H), 3.67 (m, 1H), 3.55 (m, 1H), 3.49 (dt, J=5.5, 5.5 Hz, 2H), 3.43 (m, 1H), 1.19–1.12 (m, 10H); FDMS 440 (M+1). Anal. ($C_{24}H_{29}N_3O_5$) C, H, N.

Example 22-D
[4-(3-Pyridylcarbonyl)benzoyl]-N-[3-(cyclohexyloxy) propyl]-L-serinamide:

As above from 1.156 g (4.7 mmol) of N-(3-(cyclohexyloxy)propyl)-L-serinamide (79%): mp 57°–62° C.; ¹H NMR (CDCl₃) δ 8.97 (d, J=1.8 Hz, 1H), 8.83 (m, 1H), 8.13 (dt, J=8.0, 1.8 Hz, 1H), 7.97 (d, J=8.2 Hz, 2H), 7.84 ( d, J=8.3 Hz, 2H), 7.65 (d, J=7.0 Hz, 1H), 7.49 (dd, J=8.1, 5.2 Hz, 1H), 7.29 (dd, J=6.2, 5.3 Hz, 1H), 4.66 (m, 1H), 4.15 (dd, J=11.3, 3.8 Hz, 1H), 3.99 (br s, 1H), 3.80 (dd, J=9.3, 5.4 Hz, 1H), 3.53 (t, J=5.8 Hz, 2H), 3.41 (m, 2H), 3.19 (m, 1H), 1.89–1.10 (m, 12H); FDMS 454 (M+1).

Example 23-D
[4-(3-Pyridylcarbonyl)benzoyl]-N-[4-(cyclohexyloxy) butyl]-L-serinamide:

As above from 220.1 mg (0.85 mmol) of N-(4-(cyclohexyloxy)butyl)-L-serinamide (46%): mp 55°–61° C.; ¹H NMR (CDCl₃) δ 9.01 (d, J=1.7 Hz, 1H), 8.87 (dd, J=4.9, 1.3 Hz, 1H), 8.20 (dt, J=7.9, 1.8 Hz, 1H), 7.98 (d, J=8.3 Hz, 2H), 7.88 (d, J=8.3 Hz, 2H), 7.56 (m, 2H), 7.05 (t, J=5.5 Hz, 1H), 4.64 (m, 1H), 4.22 (dd, J=11.4, 3.4 Hz, 1H), 3.79 (dd, J=11.4, 5.1 Hz, 1H), 3.46 (m, 2H), 3.34 (m, 2H), 3.20 (m, 1H), 1.92–1.14 (m, 14H); FDMS 468 (M+1). Anal. ($C_{26}H_{33}N_3O_4$) C, H, N.

Example 24-D
[4-(3-Pyridylcarbonyl)benzoyl]-N-[3-([(cis) and (trans)]-4-methoxycyclohexyl)propyl]-L-serinamides:

As above from 807.1 mg (3.12 mmol) of N-(3-([(cis) and (trans)]-4-methoxy-cyclohexyl)propyl)-L-serinamides (62%): ¹H NMR (CDCl₃, cis-isomer only) δ 8.97 (d, J=1.6 Hz, 1H), 8.84 (dd, J=4.9, 1.4 Hz, 1H), 8.13 (dt, J=7.9, 1.8 Hz, 1H), 7.96 (d, J=8.2 Hz, 2H), 7.85 (d, J=8.2 Hz, 2H), 7.67 (d, J=7.0 Hz, 1H), 7.49 (dd, J=8.0, 5.1 Hz, 1H), 7.14 (distorted t, J=~5.6 Hz, 1H), 4.68 (m, 1H), 4.19 (dd, J=11.3, 3.8 Hz, 1H), 3.78 (dd, J=11.2, 5.7 Hz, 1H), 3.37 (br s, 1H), 3.26 (s, 3H), 3.24 (m, 2H), 2.04–0.85 (14H:); FDMS 468 (M+1). Anal. ($C_{26}H_{33}N_3O_5$) C, H, N.

(Alternative preparation for Example 2)-D
[4-(3-Pyridylcarbonyl)benzoyl]-N-(4-cyclohexylbutyl)-L-serinamide:

As above from 3.53 g (15.5 mmol) of N-(4-cyclohexylbutyl)-L-serinamide (65%): ¹H NMR (CDCl₃) δ 8.96 (s, 1H), 8.81 (dd, J=4.9, 1.4 Hz, 1H), 8.11 (dt, J=7.9, 1.8 Hz, 1H), 7.94 (d, J=8.3 Hz, 2H), 7.83 (d, J=8.2 Hz, 2H), 7.64 (d, J=6.9 Hz, 1H), 7.46 (m, 1H), 7.09 (t, J=5.5 Hz, 1H), 4.67 (m, 1H), 4.19 (dd, J=11.3, 3.5 Hz, 2H), 3.76 (dd, J=11.1, 5.5 Hz, 1H), 3.25 (dt, J=6.8, 6.2 Hz, 2H), 1.63–0.77 (m, 17H); FDMS 452 (M+1).

E. Oxazolines of the following formula were prepared from the corresponding compound of Formula (L)-XXXIVa as described below:

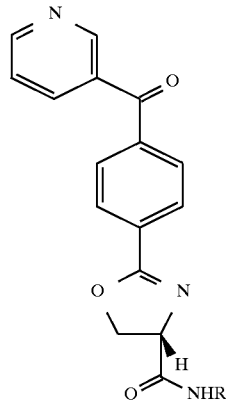

Example 18-E
(S)-4,5-Dihydro-2-[4-(3-pyridyl-carbonyl)phenyl] oxazole-4- (N-phenethyl)carboxamide:

To a mixture of 640.8 mg (1.53 mmol) of the bisamide and 805.2 mg (3.07 mmol) of Ph₃P in 14 mL of CH₃CN were added 0.30 mL (3.07 mmol) of CCl₄ and 0.54 mL (3.07 mmol) of diisopropylethylamine at room temperature. The mixture was stirred at room temperature for 24 h. The solvent and the excess liquid reagents were removed under reduced pressure and the residue was purified by flash chromatography using EtOAc—CH₂Cl₂ (3:1) which contained 1% AcOH to afford 504.6 mg (82%) of the oxazoline: ¹H NMR (CDCl₃) δ 9.00 (s, 1H) , 8.85 (br s, 1H), 8.16 (d, J=7.8 Hz, 1H), 8.06 (d, J=8.2 Hz, 2H), 7.86 (d, J=8.2 Hz, 2H), 7.51 (dd, J=7.3, 4.9 Hz, 1H), 7.20 (m, 5H), 6.72 (br s, 1H), 4.86 (dd, J=9.6, 9.5 Hz, 1H), 4.68 (m, 2H), 3.55 (m, 2H), 2.83 (t, J=6.9 Hz, 2H); FDMS 399 (M+).

Examples 19-E and 20-E
(+)- and (−)-(4S)-4,5-Dihydro-2-[4-(3-pyridylcarbonyl) phenyl]oxazole-4-[N-((trans) -2-phenylcyclopropyl)] carboxamides:

Prepared from 5.231g (12.2 mmol) of the bisamide diastereomers as above (except the reaction time: 5.5 h). Obtained 982.3 mg (20%) of (+)-isomer and 559.9 mg (14%) of (−)-isomer. (+)-isomer: mp 138°–141° C.; [α]$_D$ +47.60 (c 1.0, MeOH); ¹H NMR (CDCl₃) δ 9.00 (s, 1H), 8.85 (br d, 1H), 8.16 (buried, 1H), 8.13 (d, 2H), 7.88 (d, 2H), 7.49 (dd, 1H), 7.27 (m, 2H), 7.18 (m, 3H), 6.89 (br d, 1H), 4.91 (dd, 1H), 4.74 (m, 2H), 2.97 (m, 1H), 2.11 (m, 1H), 1.25 (m, 2H); FDMS 411 (M+). Anal. ($C_{25}H_{21}N_3O_3 \cdot 0.6C_2H_4O_2$) C, H, N. (−)-isomer: mp 71°–76° C.; $[\alpha]_D$ −62.2° (c 1.0, MeOH); $^1$H NMR (CDCl$_3$) δ 8.99 (br s, 1H), 8.84 (br d, 1H), 8.15 (buried, 1H), 8.12 (d, 2H), 7.88 (d, 2H), 7.48 (br dd, 1H), 7.26 (m, 2H), 7.13 (m, 3H), 6.87 (br d, 1H), 4.90 (dd, 1H), 4.75 (distorted d, 2H), 2.96 (m, 1H), 2.10 (m, 1H), 1.28 (m, 2H); FDMS 411 (M+). Anal. ($C_{25}H_{21}N_3O_3$) C, H, N.

Example 21-E
(S)-4,5-Dihydro-2-[4-(3-pyridylcarbonyl)phenyl]oxazole-4-[N-[2-(cyclohexyloxy)ethyl]]carboxamide:

As above from 1.61 g (3.66 mmol) of the bisamide (68%): $^1$H NMR (CDCl$_3$) δ 9.00 (s, 1H), 8.86 (br d, J=3.9 Hz, 1H), 8.18 (dd, J=1.9, 1.9 Hz, 1H), 8.14 (d, J=8.3 Hz, 2H), 7.87 (d, J=8.2 Hz, 2H), 7.52 (dd, J=7.8, 4.9 Hz, 1H), 7.08 (br s, 1H), 4.92 (dd, J~10.2, 9.0 Hz, 1H), 4.73 (m, 2H), 3.56 (m, 2H), 3.47 (m, 2H), 3.25 (m, 1H), 1.90–1.15 (m, 10H); FDMS 421 (M+). Anal. ($C_{24}H_{27}N_3O_4$), C, H, N.

Example 22-E
(S)-4,5-Dihydro-2-[4-(3-pyridylcarbonyl)phenyl]oxazole-4-[N-[3-(cyclohexyloxy)propyl]]carboxamide:

As above from 1.579 g (3.48 mmol) of the bisamide (79%): $^1$H NMR (CDCl$_3$) δ 8.22 (br s, 1H), 8.19 (br s, 1H), 8.14 (d, J=8.0 Hz, 2H), 7.99 (d, 1H), 7.91 (buried, 1H), 7.87 (d, J=8.0 Hz, 2H), 7.16 (br t, 1H), 4.91 (dd, J=10.3, 9.4 Hz, 1H), 4.73 (m, 2H), 3.61–3.33 (m, 4H), 3.20 (m, 1H), 1.95–1.10 (m, 12H); FDMS 436 (M+1). Anal. $C_{25}H_{29}N_3O_4$ C, H, N.

Example 23-E
(S)-4,5-Dihydro-2-[4-(3-pyridylcarbonyl)phenyl]oxazole-4-[N-[4-(cyclohexyloxy)butyl]]carboxamide:

As above from 161.3 mg (0.34 mmol) of the bisamide (59%): $^1$H NMR (CDCl$_3$) δ 8.98 (d, J=1.3 Hz, 1H), 8.82 (dd, J=4.9, 1.1 Hz, 1H), 8.13 (buried, 1H), 8.10 (d, J=8.1 Hz, 2H), 7.85 (d, J=8.2 Hz, 1H), 7.47 (m, 1H), 6.77 (br t, J=~5.5 Hz, 1H), 4.88 (dd, J=10.5, 9.0 Hz, 1H), 4.73 (dd, J=10.6, 8.9 Hz, 1H), 4.65 (dd, J=8.8, 8.8 Hz, 1H), 3.44 (t, J=5.7 Hz, 2H), 3.37 (m, 1H), 3.27 (m, 1H), 3.17 (m, 1H), 1.86–1.11 (m, 14H); FDMS 450 (M+1). Anal. $C_{26}H_{31}N_3O_4 \cdot 0.26C_4H_8O_2$ C, H, N.

Example 24-E
(4S)-4,5-Dihydro-2-[4-(3-pyridylcarbonyl)phenyl]oxazole-4-[N-[3-([(cis) and (trans)]-4-methoxycyclohexyl)propyl]]carboxamides:

As above from 905.4 mg (1.94 mmol) of the mixture of cis- and trans-bisamides (61%): $^1$H NMR (CDCl$_3$, cis-isomer only) δ 8.99 (d, J=1.5 Hz, 1H), 8.84 (dd, J=5.5, 1.3 Hz, 1H), 8.16 (dd, J=1.9, 1.8 Hz, 1H), 8.12 (d, J=8.1 Hz, 2H), 7.87 (d, J=8.4 Hz, 2H), 7.49 (dd, J=7.9, 5.0 Hz, 1H), 6.88 (t, J=5.0 Hz, 1H), 4.89 (dd, J=10.6, 8.9 Hz, 1H), 4.75 (dd, J=10.7, 8.8 Hz, 1H), 4.67 (dd, J=8.7, 8.7 Hz, 1H), 3.37 (br s, 1H), 3.32 (s, 3H), 3.32 (m, 2H), 2.05–0.92 (m, 13H); FDMS 449 (M+). Anal. ($C_{26}H_{31}N_3O_4$) C, H, N.

(Alternative preparation of Example 2)-E
(4S)-4,5-Dihydro-2-[4-(3-pyridylcarbonyl)phenyl]oxazole-4-[N-(4-cyclohexylbutyl)]-L-serinamide:

As above from 4.07 g (9.0 mmol) of [4-(3-pyridylcarbonyl)benzoyl]-N-(4-cyclohexylbutyl)-L-serinamide (75%): $^1$H NMR (CDCl$_3$) δ 8.99 (s, 1H), 8.84 (d, J=2.2 Hz, 1H), 8.13 (buried m, 1H), 8.11 (d, J=8.1 Hz, 2H), 7.86 (d, J=8.2 Hz, 2H), 7.48 (dd, J=11.8, 4.9 Hz, 1H), 6.65 (t, J=5.3 Hz, 1H), 4.88 (m, 1H), 4.70 (m, 2H), 3.37–3.19 (m, 2H), 1.66–0.80 (m, 17H); FDMS 433 (M+).

F. Oxazoles of Formula IIIa were prepared from the corresponding oxazolines as described below.

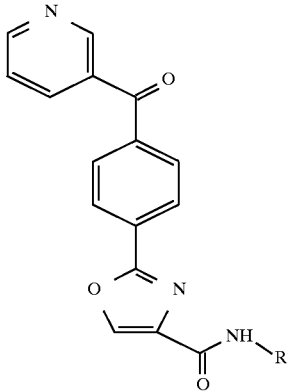

IIIa

Example 18-F
2-[4-(3-Pyridylcarbonyl)phenyl]oxazole-4-(N-phenethyl)carboxamide:

A mixture of 504.6 mg (1.27 mmol) of the oxazoline and 1.01 g of NiO$_2$ in 10 mL of benzene-1,4-dioxane (4:1) was heated at reflux (90° C. bath temperature) for 2 h. Another 1.01 g of NiO$_2$ (total 4× wt of oxazoline) was added and the mixture was heated at reflux for 3 more h. After cooling to room temperature, the mixture was transferred to a 250 mL flask with 30 mL of CH$_2$Cl$_2$ and treated with 20 mL of 15N NH$_4$OH at 0° C. for 15 min. To this was added 1–2 teaspoonful diatomaceous earth and 100 mL of CH$_2$Cl$_2$ and the mixture was stirred vigorously for 10 min. This was then filtered through a pad of diatomaceous earth and the filtrate was transferred to a separatory funnel. The aqueous layer and the solid separated were combined, suspended in 100 mL of CH$_2$Cl$_2$, and stirred vigorously for 10 min. This was then filtered and the filtrate was separated by a separatory funnel. The organic layers were combined, dried over MgSO$_4$, and concentrated. Flash chromatography with EtOAc-AcOH-CH$_2$Cl$_2$ (34:1:65) furnished 299.5 mg (60 %) of the oxazole: $^1$H NMR (CDCl$_3$) δ 9.01 (s, 1H), 8.85 (br d, J=4.2 Hz, 1H) , 8.30 (s, 1H), 8.18 (buried, 1H), 8.16 (d, J=8.2 Hz, 2H), 7.92 (d, J=8.3 Hz, 2H), 7.51 (dd, J=8.8, 5.0 Hz, 1H), 7.31 (m, 5H), 7.12 (t, J=5.7 Hz, 1H), 3.72 (ddd, J=7.0, 6.8, 6.7 Hz, 2H), 2.95 (dd, J=7.2, 7.1 Hz, 2H); FDMS 397 (M+). Anal. ($C_{24}H_{19}N_3O_3 \cdot 0.24C_2H_4O_2$) C, H, N.

Example 19-F
(+)-2-[4-(3-Pyridylcarbonyl)phenyl]-oxazole-4-[N-((trans)-2-phenylcyclopropyl)]-carboxamide:

Prepared similarly from 979.4 mg (2.38 mmol) of the oxazoline as above except adding 6.93 g of NiO$_2$ in 3 portions (7× weight of oxazoline) and 25 mL of benzene as solvent at room temperature to 65° C. (17%): mp 165°–170° C.; $[\alpha]_D$ +0.40° (c 1.0, MeOH); $^1$H NMR (CDCl$_3$) δ 9.00 (br s, 1H), 8.85 (br s, 1H), 8.32 (s, 1H), 8.19 (d, J=8.4 Hz, 2H), 8.17 (buried, 1H), 7.93 (d, J=8.3 Hz, 2H), 7.51 (m, 1H), 7.25 (m, 6H), 3.09 (m, 1H), 2.24 (m, 1H), 1.37 (m, 2H); FDMS 409 (M+). Anal. ($C_{25}H_{19}N_3O_3$) C, H, N.

Example 20-F
(−)-2-[4-(3-Pyridylcarbonyl)phenyl]-oxazole-4-[N-((trans)-2-phenylcyclopropyl)]-carboxamide:

Prepared similarly from 559.9 mg (1.36 mmol) of the oxazoline as above adding 3.18 g of NiO$_2$ in two portions (~6× weight of oxazoline) in 14 mL of benzene as solvent at room temperature for 4 h reaction time (55%): mp 174°–179° C.; $[\alpha]_D$ +0.4° (c 1.0, MeOH, the observed value is within the error limit of Polarimeter, ±0.6°); FDMS 409 (M+). Anal. ($C_{25}H_{19}N_3O_3$) C, H, N.

Example 21-F
2-[4-(3-Pyridylcarbonyl)phenyl]oxazole-4-[N-[2-(cyclohexyloxy)ethyl]]carboxamide:

Prepared from 1.004 g (2.38 mmol) of the oxazoline and 5.02 g of $NiO_2$ in 20 mL of anhydrous benzene at room temperature for 1.5 h and purified by preparative HPLC using 3% MeOH-$CH_2Cl_2$ as an eluent after the prescribed workup as above (61%): $^1$H NMR ($CDCl_3$) δ 9.02 (d, J=1.8 Hz, 1H), 8.86 (dd, J=5.0, 1.4 Hz, 1H), 8.31 (s, 1H), 8.20 (d, J=8.3 Hz, 2H), 8.19 (buried, 1H), 7.94 (d, J=8.3 Hz, 2H), 7.52 (m, 1H), 7.45 (br s, 1H), 3.65 (m, 4H), 3.32 (m, 1H), 1.95–1.24 (m, 10H); FDMS 420 (M+1). Anal. ($C_{24}H_{25}N_3O_4$) C, H, N.

Example 22-F
2-[4-(3-Pyridylcarbonyl)phenyl]oxazole-4-[N-[3-(cyclohexyloxy)propyl]]carboxamide:

Similarly as above from 1.187 g (2.73 mmol) of the oxazoline and 5.935 g of $NiO_2$ in 25 mL of anhydrous benzene at room temperature for 4 h (38%): $^1$H NMR ($CDCl_3$) δ 9.03 (s, 1H), 8.87 (br d, J=3.9 Hz, 1H), 8.30 (s, 1H), 8.21 (d, J=8.3 Hz, 2H), 7.93 (d, J=8.4 Hz, 2H), 7.79 (br t, J=~5.3 Hz, 1H), 7.54 (dd, J=7.9, 4.9 Hz, 1H), 3.63 (m, 4H), 3.32 (m, 1H), 2.03–1.24 (m, 12H); FDMS 434 (M+1). Anal. ($C_{25}H_{27}N_3O_4 \cdot 0.14 C_4H_8O_2$) C, H, N.

Example 23-F
2-[4-(3-Pyridylcarbonyl)phenyl]oxazole-4-[N-[4-(cyclohexyloxy)butyl]]carboxamide:

Similarly as above from 84.4 mg (0.19 mmol) of the oxazoline and 590 mg of $NiO_2$ in 2.0 mL of benzene at room temperature for 7 h (53%): $^1$H NMR ($CDCl_3$) δ 9.01 (s, 1H), 8.84 (br d, J=3.8 Hz, 1H), 8.29 (s, 1H), 8.18 (d, J=8.4 Hz, 2H), 8.14 (dt, J=7.9, 1.8 Hz, 1H), 7.92 (d, J=8.3 Hz, 2H), 7.49 (dd, J=7.8, 4.8 Hz, 1H), 7.19 (t, J=5.8 Hz, 1H), 3.50 (m, 4H), 3.22 (m, 1H), 1.93–1.16 (m, 14H); FDMS 447 (M+). Anal. ($C_{26}H_{29}N_3O_4$), C, H, N.

Example 24-F
2-[4-(3-Pyridylcarbonyl)phenyl]oxazole-4-[N-[3-([(cis) and (trans)]-4-methoxycyclohexyl)propyl]]carboxamides:

As above from 493.9 mg (1.1 mmol) of the oxazolines and 2.47 g of $NiO_2$ in 10 mL of benzene at room temperature for 2.5 h (68%): $^1$H NMR ($CDCl_3$, cis-isomer only) δ 9.01 (d, J=1.2 Hz, 1H), 8.85 (dd, J=4.5, 1.0 Hz, 1H), 8.29 (s, 1H), 8.19 (d, J=8.4 Hz, 2H), 8.15 (dd, J=1.8, 1.8 Hz, 1H), 7.93 (d, J=8.3 Hz, 2H), 7.50 (dd, J=7.9, 4.8 Hz, 1H), 7.07 (t, J=5.5 Hz, 1H), 3.44 (dt, J=6.9, 6.8 Hz, 2H), 3.39 (br s, 1H), 3.33 (s, 3H), 2.10–0.85 (m, 13H); FDMS 447 (M+). Anal. ($C_{26}H_{29}N_3O_4$), C, H, N.

(Alternative Dreparation of Example 2)-F
2-[4-(3-Pyridylcarbonyl)phenyl]oxazole-4-[N-(4-cyclohexylbutyl)]carboxamide:

Prepared similarly as above from 128.9 mg (0.30 mmol) of the oxazoline and 516.0 mg of $NiO_2$ (in two portions) in 3.0 mL of benzene-1,4-dioxane (4:1) at reflux for 5 h (72%) or as shown below from 419.0 mg (1.01 mmol) of the crude oxazole acid and 237.5 mg (1.53 mmol) of 4-cyclohexylbutylamine (70%): $^1$H NMR ($CDCl_3$) δ 9.00 (s, 1H), 8.84 (br s, 1H), 8.28 (s, 1H), 8.18 (d, J=8.3 Hz, 2H), 8.16 (buried, 1H), 7.91 (d, J=8.2 Hz, 2H), 7.48 (dd, J=7.7, 5.1 Hz, 1H), 7.05 (t, J=5.6 Hz, 1H), 3.44 (dt, J=6.8, 6.8 Hz, 2H), 1.69–0.83 (m, 17H); FDMS 431 (M+). Anal. ($C_{26}H_{29}N_3O_3$) C, H, N.

G. Acids of Formula I were prepared from the corresponding ketones of Formula IIIa as described below. In some instances both the E-isomer (Examples 21A and 22A) and the Z-isomer (Examples 21B and 22B) were isolated and characterized.

Example 18-G
(E)-7-[4-[4-[(Phenethylamino)carbonyl]-2-oxazolyl]phenyl]-7-(3-pyridyl)hept-6-enoic Acid:

To a cooled (0° C.) solution of 293.6 mg (0.74 mmol) of the pyridyl ketone and 670.4 mg (1.48 mmol) of (5-carboxypentyl)triphenylphosphonium bromide in 2.5 mL of THF was added dropwise 2.95 mL (2.95 mmol) of 1.0M t-BuOK in THF over 10 min period. The dark brown solution was stirred at 0° C. for 1.5 h, and then the reaction was quenched with 20 mL of saturated aqueous $NH_4Cl$. The mixture was extracted with 3×50 mL of $CH_2Cl_2$. The combined extract was dried over $MgSO_4$, concentrated and purified by preparative HPLC with MeOH-AcOH-$CH_2Cl_2$ (2:1:97) as the eluent to afford 56.1 mg (8.4%) of the less polar (Z)-heptenoic acid and 434.9 mg of the (E)-isomer containing a byproduct from the Wittig salt. In order to purify it, the (E)-isomer was therefore esterified with $CH_2N_2$ which was generated by a standard method from MNNG and aqueous NaOH in $Et_2O$. The ester was isolated cleanly by flash chromatography with EtOAc-hexanes-$CH_2Cl_2$ (2:1:1) as the eluent. The ester (102.5 mg) was then hydrolyzed with 1N NaOH in THF-MeOH (1:1). Flash chromatography with EtOAc-MeOH-AcOH-$CH_2Cl_2$ (50:1:1:48) yielded 92.5 mg (25%) of the pure (E)-heptenoic acid: mp 56°–61° C.; $^1$H NMR ($CDCl_3$) δ 8.58 (s, 1H), 8.47 (d, J=4.1 Hz, 1H), 8.26 (s, 1H), 8.02 (d, J=8.2 Hz, 2H), 7.44 (dt, J=8.0, 1.5 Hz, 1H), 7.35–7.16 (m, 9H), 6.19 (t, J=7.4 Hz, 1H), 3.70 (dt, J=6.9, 6.7 Hz, 2H), 2.94 (t, J=7.2 Hz, 2H), 2.32 (t, J=7.8 Hz, 2H), 2.20 (ddd, J=7.3, 7.2, 7.0 Hz, 2H), 1.68–1.51 (m, 4H); FDMS 496 (M+1). Anal. ($C_{30}H_{29}N_3O_4 \cdot 0.1 C_2H_4O_2$) C, H, N.

Example 19-G
(+)-(E)-7-[4-[4-[[(2-(trans)Phenylcyclopropyl)amino]carbonyl]-2-oxazolyl]phenyl]-7-(3-pyridyl)hept-6-enoic Acid:

Prepared as above from 208.0 mg (0.51 mmol) of the (+)-pyridyl ketone and 461.0 mg (1.02 mmol) of the Wittig salt without esterification step. Flash chromatography with EtOAc-MeOH-AcOH-$CH_2Cl_2$ (68:1:1:30) furnished 223.8 mg (87%) of a pale yellow fluffy sold (E/Z=97:3 by HPLC analysis): mp 78°–87° C.; $[\alpha]_D$ +116.20° (c 1.0, MeOH); $^1$H NMR ($CDCl_3$) δ 8.58 (br s, 1H), 8.47 (br d, J=2.7 Hz, 1H), 8.28 (s, 1H), 8.04 (d, J=8.3 Hz, 2H), 7.53 (dd, J=7.2, 1.1 Hz, 1H), 7.46 (br dd, J=~8.3, 1.6 Hz, 2H), 7.28 (m, 4H), 7.20 (m, 3H), 6.19 (t, J=7.5 Hz, 1H), 3.09 (m, 1H), 2.32 (dd, J=7.2, 6.8 Hz, 2H), 2.19 (m, 3H), 1.64 (m, 2H), 1.55 (m, 2H), 1.36 (m, 2H); FDMS 508 (M+1). Anal. ($C_{31}H_{29}N_3O4$) C, H, N.

Example 20-G
(−)-(E)-7-[4-[4-[[(2-(trans)Phenylcyclopropyl)amino]carbonyl]-2-oxazolyl]phenyl]-7-(3-pyridyl)hept-6-enoic Acid:

Prepared as above from 266.7 mg (0.65 mmol) of the (−)-pyridyl ketone and 591.1 mg (1.30 mmol) of the Wittig salt which yielded in 29% yield a white fluffy solid (E/Z=~10:1 by $^1$H NMR): mp 78°–82° C.; $[\alpha]_D$ −93.4° (c 1.0, MeOH); FDMS 508 (M+1). 96% pure by HPLC.

Example 21A-G
(E)-7-[4-[4-[[[2-(Cyclohexyloxy)eth1]amino]carbonyl]-2-oxazolyl]phenyl]-7-(3-pyridyl)hept-6-enoic Acid:

Prepared as above from 582.4 mg (1.39 mmol) of the pyridyl ketone and 1.27 g (2.78 mmol) of the Wittig salt. Preparative HPLC with EtOAc-MeOH-AcOH-CH$_2$Cl$_2$ (80:3:1:16) gave in 60% yield a mixture of Wittig product (E/Z=~5.5:1) from which 245.5 mg of (E)-isomer was isolated cleanly: mp 51°–59° C.; $^1$H NMR (CDCl$_3$) δ 8.59 (s, 1H), 8.49 (br d, J=2.9 Hz, 1H), 8.28 (s, 1H), 8.07 (d, J=8.2 Hz, 2H), 7.50 (distorted br d, J=7.3 Hz, 2H), 7.29 (d, J=8.2 Hz, 2H), 7.27 (buried, 1H), 6.21 (t, J=7.4 Hz, 1H), 3.65 (s, 4H), 3.32 (m, 1H), 2.34 (dd, J=7.2, 6.8 Hz, 2H), 2.22 (ddd, J=7.4, 7.2, 6.9 Hz, 2H), 1.95–1.19 (m, 14H); FDMS 518 (M+1). Anal. (C$_{30}$H$_{35}$N$_3$O$_5$) C, H; N: calcd, 8.12; found, 7.60. 97.5% pure by HPLC.

Example 21B-G
(Z)-7-[4-[4-[[[2-(Cyclohexyloxy)ethyl]amino]carbonyl]-2-oxazolyl]phenyl]-7-(3-pyridyl)hept-6-enoic Acid:

Prepared as above from 582.4 mg (1.39 mmol) of the pyridyl ketone and 1.27 g (2.78 mmol) of the Wittig salt. Preparative HPLC with EtOAc-MeOH-AcOH-CH$_2$Cl$_2$ (80:3:1:16) gave in 60% yield a mixture of Wittig product (E/Z=~5.5:1) from which 29.1 mg of (Z)-isomer was isolated cleanly: mp 65°–71° C.; FDMS 518 (M+1). Anal. (C$_{30}$H$_{35}$N$_3$O$_5$) C, H, N. 95.2% pure by HPLC.

Example 22A-G
(E)-7-[4-[4-[[[3-(Cyclohexyloxy)propyl]amino]carbonyl]-2-oxazolyl]phenyl]-7-(3-pyridyl)hept-6-enoic Acid:

Prepared as above from 418.6 mg (0.97 mmol) of the pyridyl ketone and 883.2 mg (1.93 mmol) of the Wittig salt. Preparative HPLC with MeOH-AcOH-CH$_2$Cl$_2$ (3:1:96) provided in 86% yield a mixture of Wittig product (E/Z=~6.4:1) from which 257.2 mg of (E)-isomer was isolated cleanly: mp 57°–62° C; $^1$H NMR (CDCl$_3$) δ 8.62 (s, 1H), 8.49 (br d, J=3.7 Hz, 1H), 8.27 (s, 1H), 8.07 (d, J=8.1 Hz, 2H), 7.77 (distorted t, J=~3.5 Hz, 1H), 7.48 (br d, J=8.0 Hz, 1H), 7.27 (d, J=8.2 Hz, 2H), 7.26 (buried, 1H), 6.22 (t, J=7.4 Hz, 1H), 3.62 (m, 4H), 3.30 (m, 1H), 2.34 (dd, J=7.2, 6.8 Hz, 2H), 2.22 (ddd, J=7.3, 7.2, 7.1 Hz, 2H), 2.02–1.22 (M, 16H); FDMS 532 (M+1). Anal. (C$_{31}$H$_{37}$N$_3$O$_5$) C, H, N. 94.6% pure by HPLC.

Example 22B-G
(Z)-7-[4-[4-[[[3-(Cyclohexyloxy)propyl]amino]carbonyl]-2-oxazolyl]phenyl]-7-(3-pyridyl)hept-6-enoic Acid:

Prepared as above from 418.6 mg (0.97 mmol) of the pyridyl ketone and 883.2 mg (1.93 mmol) of the Wittig salt. Preparative HPLC with MeOH-AcOH-CH$_2$Cl$_2$ (3:1:96) provided in 86% yield a mixture of Wittig product (E/Z=~6.4:1) from which 28.8 mg of (Z)-isomer was isolated cleanly: mp 57°–62° C.; FDMS 532 (M+1). Anal. (C$_{31}$H$_{37}$N$_3$O$_5$) C, H, N. 98.4% pure by HPLC.

Example 23-G
(E)-7-[4-[4-[[[4-(Cyclohexyloxy)butyl]amino]carbonyl]-2-oxazolyl]phenyl]-7-(3-pyridyl)hept-6-enoic Acid:

Prepared as above from 38.8 mg (0.087 mmol) of the pyridyl ketone and 79.3 mg (0.17 mmol) of the Wittig salt. Flash chromatography with MeOH-AcOH-Et$_2$O (2:2:96) provided 29.6 mg (63%) of the Wittig product (E-isomer: 88.3% by HPLC analysis): $^1$H NMR (CDCl$_3$) δ 8.60 (s, 1H), 8.48 (br d, J=4.1 Hz, 1H), 8.27 (s, 1H), 8.06 (d, J=8.2 Hz, 2H), 7.45 (br d, J=7.9 Hz, 1H), 7.29 (d, 2H), 7.22 (m, 2H), 6.20 (t, J=7.4 Hz, 1H), 3.51 (m, 4H), 3.23 (m, 1H), 2.33 (dd, J=7.1, 6.7 Hz, 2H), 2.20 (ddd, J=7.3, 7.1, 6.9 Hz, 2H), 1.95–1.14 (m, 18H); FDMS 546 (M+1). Anal. (C$_{32}$H$_{39}$N$_3$O$_5$) C, H, N.

Example 24-G
(E)-7-[4-[4-[[[3-((cis)-4-Methoxycyclohexyl)propyl]amino]carbonyl]-2-oxazolyl]phenyl]-7-(3-pyridyl)hept-6-enoic Acid:

Prepared as above from 227.4 mg (0.51 mmol) of the mixture of cis- and trans-pyridyl ketones (c/t=~5.1:1) and 464.8 mg (1.02 mmol) of the Wittig salt. Preparative HPLC with MeOH-AcOH-Et$_2$O (2:2:96) yielded 240.4 mg (87%) of the product (major (E)-(cis)-isomer: 88% by HPLC analysis): $^1$H NMR (CDCl$_3$) δ 8.60 (br s, 1H), 8.50 (br s, 1H), 8.28 (s, 1H), 8.08 (d, J=8.3 Hz, 2H), 7.50 (br d, J=7.5 Hz, 2H), 7.29 (d, J=8.2 Hz, 2H), 7.11 (distorted t, 1H), 6.22 (t, J=7.5 Hz, 1H), 3.45 (m, 3H), 3.31 (s, 3H), 2.33 (dd, J=7.2, 6.9 Hz, 2H), 2.22 (ddd, J=7.3, 7.2, 6.8 Hz, 2H), 1.88–1.24 (m, 17H); FDMS 546 (M+1). Anal. (C$_{32}$H$_{39}$N$_3$O$_5$) C, H, N.

(Alternative preparation of Example 2)-G (E)-7-[4-[4-[[(4-Cyclohexylbutyl)amino]carbonyl]-2-oxazolyl]phenyl]-7-(3-pyridyl)hept-6-enoic Acid:

Prepared as above from 0.952 g (2.2 mmol) of the pyridyl ketone, 2.00 g (4.4 mmol) of (5-carboxypentyl)triphenylphosphonium bromide, and 8.8 mL (8.8 mmol) of 1.0M t-BuOK in 6.0 mL of THF at 0° C. for 2 h. Preparative HPLC with MeOH-AcOH-CH$_2$Cl$_2$ (2:1:97) furnished total amount of 1.06 g (90%) of the (E)- and (Z)-product (E/Z= 8.7:1) from which 941.8 mg of (E)-heptenoic acid was separated cleanly: mp 52°–56° C.; $^1$H NMR (CDCl$_3$) δ 8.55 (br s, 1H), 8.47 (d, J=2.7 Hz, 1H), 8.27 (s, 1H), 8.04 (d, J=8.2 Hz, 2H), 7.47 (d, J=8.0 Hz, 1H), 7.26 (d, J=8.2 Hz, 2H), 7.33 (buried, 1H), 7.12 (t, J=5.9 Hz, 1H), 6.18 (t, J=7.5 Hz, 1H), 3.43 (ddd, J=6.9, 6.8, 6.6 Hz, 2H), 2.31 (dd J=7.2, 6.9 Hz, 2H), 2.19 (ddd, J=7.3, 7.2, 7.1 Hz, 2H), 1.68–0.82 (m, 21H); FDMS 530 (M+1). Anal. (C$_{32}$H$_{39}$N$_3$O$_4$.0.2 C$_2$H$_4$O$_2$) C, H, N.

Alternative Preparation of Example 1

(4S)-(E) -7-[4-[4-[[(4-Cyclohexylbutyl)amino]carbonyl]-4,5-dihydro-2-oxazolyl]phenyl]-7- (3-pyridyl)hept-6-enoic Acid Using the method described above at Example 18-G, 1.472 g (3.4 mmol) of (4S)-4,5-dihydro-2-[4-(3-pyridylcarbonyl)phenyl]oxazole-4-[N-(4-cyclohexylbutyl)] -L-serinamide was treated with 3.08 g (6.8 mmol) of (5-carboxypentyl)triphenylphosphonium bromide and 13.6 mL (13.6 mmol) of 1.0M t-BuOK in 10.0 mL of THF at 0° C. for 2.5 hr. Preparative HPLC with MeOH-AcOH-CH$_2$Cl$_2$ (3:0.5:96.5) yielded ~700 mg (38%) of the title product and ~670 mg (37%) of the β-elimination Wittig product (less polar material) (E)-7-[4-[[[1-[[(4-cyclohexylbutyl)amino]carbonyl]-eth-1-enyl]amino]carbonyl]phenyl]-7-(3-pyridyl)-hept-6-enoic acid (311030): mp 61°–63 0C.; $^1$H NMR (CDCl$_3$) δ 9.05 (s, 1H), 8.58 (s, 1H), 8.48 (d, J=3.3 Hz, 1H), 7.89 (d, J=8.2 Hz, 2H), 7.43 (br d, J=8.0 Hz, 1H), 7.26 (d, J=8.0 Hz, 2H), 7.25 (buried, 1H), 6.63 (d, J=1.1 Hz, 1H), 6.55 (br s, 1H), 6.21 (t, J=7.4 Hz, 1H), 5.35 (s, 1H), 3.37 (dt, J=6.8, 6.3 Hz, 2H), 2.32 (dd, J=7.1, 6.9 Hz, 2H), 2.18 (ddd, J=7.3, 7.2, 7.1 Hz, 2H), 1.69–0.83 (m, 21H); FDMS 532 (M+1). Anal. (C$_{32}$H$_{41}$N$_3$O$_4$) C, H, N.

Examples 25–35

A. N-[4-(3-Pyridylcarbonyl)benzoyl]-DL-serine Methyl Ester

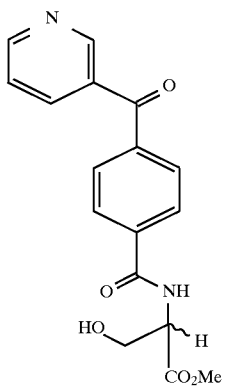

To a mixture of 2.29 g (10 mmol) of the benzoic acid of Example 17-C, 1.57 g (10 mmol) of DL-serine methyl ester hydrochloride, and 1.36 g (10 mmol) of HOBT in 60 mL of DMF was added 2.2 mL (20 mmol) of NMM and 1.93 g (10 mmol) of WSC at 0° C. The mixture was stirred overnight while allowed to warm up slowly to 20° C. on its own (16.5 h). The reaction mixture was taken up in 500 mL of EtOAc and washed with 2×250 mL of $H_2O$ and 250 mL of brine which were back extracted with 2×500 mL of EtOAc. The combined organic layers were dried over $MgSO_4$ and concentrated. Preparative HPLC of the residue eluting with 3% MeOH-$CH_2Cl_2$ gave 2.67 g (81%) of the hygroscopic serinamide: $^1$H NMR ($CDCl_3$) δ 8.93 (s, 1H), 8.80 (d, J=4.1 Hz, 1H), 8.10 (d, J=7.9 Hz, 1H), 7.94 (d, J=8.3 Hz, 2H), 7.81 (d, J=8.2 Hz, 2H), 7.47 (dd, J=7.8, 4.9 Hz, 1H), 7.35 (d, J=7.3 Hz, 1H), 4.87 (dt J=7.4, 3.7 Hz, 1H), 4.12 (dd, J=11.3, 3.5 Hz, 1H), 4.04 (dd, J=11.3, 3.2 Hz, 1H), 3.80 (S, 3H), 2.71 (br s, 1H); FDMS 329 (M+1). Anal. ($C_{17}H_{16}N_2O_5$) C, H, N.

B. Methyl 4,5-Dihydro-2-[4-(3-pyridylcarbonyl)phenyl]oxazole-4-carboxylate

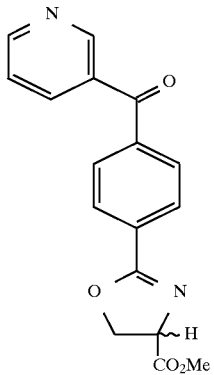

To a cooled solution (−78° C.) of 0.38 mL (2.28 mmol) of triflic anhydride in 4.5 mL of anhydrous $CH_2Cl_2$ was added dropwise 0.616 g (3.05 mmol) of diphenyl sulfoxide in 6.1 mL of $CH_2Cl_2$ over 10 min period. After stirring at −78° C. for 30 min, 3.23 g (15.2 mmol) of $K_3PO_4$ was added, followed by 0.500 g (1.52 mmol) of the serinamide in 6.4 mL of $CH_2Cl_2$. The mixture was stirred at −78° C. for another 30 min and then at 0° C. for 30 min. The reaction was quenched with 35 mL of $H_2O$ and the layers were separated. The aqueous layer was extracted with 2×50 mL of $CH_2Cl_2$. The combined organic layer was dried over $MgSO_4$ and concentrated. Flash chromatography with EtOAc-$CH_2Cl_2$ (4:1) which contained 1% MeOH gave 0.306 g (65%) of the oxazoline ester: mp 148° C.; $_1$H NMR ($CDCl_3$) δ 8.98 (s, 1H), 8.82 (d, J=4.0 Hz, 1H), 8.12 (d, J=8.3 Hz, 2H), 8.12 (buried, 1H), 7.84 (d, J=8.3 Hz, 2H), 7.47 (dd, J=7.9, 5.0 Hz, 1H), 5.00 (dd, J=10.6, 8.0 Hz, 1H), 4.75 (dd, J=8.6, 8.2 Hz, 1H), 4.64 (dd, J=10.5, 9.0 Hz, 1H), 3.83 (s, 3H); FDMS 310 (M+). Anal. ($C_{17}H_{14}N_2O_4$) C, H, N.

C. Methyl 2-[4-(3-Pyridylcarbonyl)phenyl]oxazole-4-carboxylate

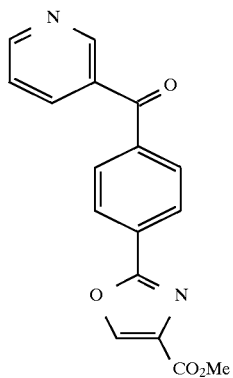

To a solution of 606.6 mg (2.0 mmol) of the oxazoline ester in 20 mL of benzene-1,4-dioxane (4:1) was added 1.2 g of $NiO_2$. The black suspension was heated at reflux (−95° C. bath temperature) for 2 h. Another 1.2 g of $NiO_2$ (total 4× wt of the oxazoline) was added and the mixture was heated at reflux for 3 h. The reaction mixture was cooled to room temperature and diluted with ca. 70 mL of $CH_2Cl_2$. This was filtered through a pad of diatomaceous earth. The solid (including diatomaceous earth) was returned to the reaction flask, suspended in 50 nLi of EtOAc-$CH_2Cl_2$ (1:1), and treated with ca. 30 mL of 14% $NH_4OH$ at 0° C. for 10–15 min. The suspension was diluted with ca. 100 mL of $CH_2Cl_2$ and filtered through a pad of diatomaceous earth. This solid treatment was repeated twice. The combined filtrate was then transferred to a separatory funnel and the layers were separated. The organic layer was washed with ca. 100 mL of brine, and the aqueous layer was back extracted with 2×150 mL of $CH_2Cl_2$. The combined organic layer was dried over $MgSO_4$, concentrated, and purified by flash chromatography with EtOAc-AcOH-$CH_2Cl_2$ (49:1:50) to afford 321.2 mg (53%) of the oxazole ester: mp 154°–157° C.; $^1$H NMR ($CDCl_3$) δ 8.99 (d, J=1.7 Hz, 1H), 8.83 (dd, J=4.6, 1.2 Hz, 1H), 8.34 (s, 1H), 8.25 (d, J=8.4 Hz, 2H), 8.13 (dt, J=7.9, 1.8 Hz, 1H), 7.91 (d, J=8.4 Hz, 2H), 7.47 (m, 1H), 3.96 (s, 3H); FDMS 308 (M+). Anal ($C_{17}H_{12}N_2O_4$) C, H, N.

D. 2-[4-(3-Pyridylcarbonyl)phenyl]oxazole-4-carboxylic Acid

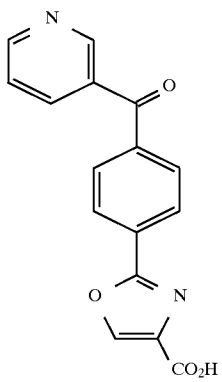

To a solution of 2.01 g (6.5 mmol) of the ester in 40 mL of THF-MeOH (1:1) was added 13.0 mL (13.0 mmol) of 1N NaOH at 0° C. The milky solution was then stirred at room temperature for 1.5 h. This was then neutralized with 13.0 mL of 1N HCl and concentrated to dryness. The white solid (containing 28.4% of NaCl by weight) was dried over $P_2O_5$ under vacuum overnight and used without further purification (an analytical sample was prepared by washing the crude product with $H_2O$ and acetone): mp 281°–282° C.; $^1$H NMP (DMSO) δ 8.92 (s, 1H), 8.88 (s, 1H), 8.82 (br d, J=2.4 Hz, 1H), 8.15 (d, J=8.3 Hz, 2H), 8.13 (buried, 1H), 7.91 (d, J=8.3 Hz, 2H), 7.59 (d, J=7.7, 4.8 Hz, 1H); FDMS 294 (M+). Anal. ($C_{16}H_{10}N_2O_4$) C, H, N.

E. Oxazole amides of Formula IIIa were prepared from the above acid and the corresponding amine of formula $H_2N$-R as described below:

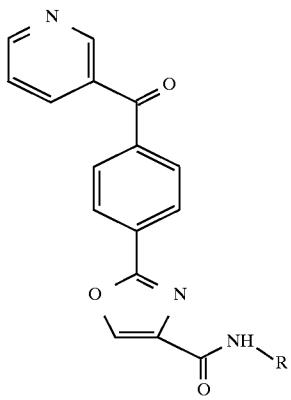

IIIa

Example 25-E
2-[4-(3-Pyridylcarbonyl)phenyl]oxazole-4-[N-[2-(cyclohexylmethoxy)ethyl]]carboxamide:

To a cooled (0° C.) mixture of 419.0 mg (1.02 mmol) of the crude 2-[4-(3-pyridylcarbonyl)phenyl]oxazole-4-carboxylic acid (71.6% purity), 206.6 mg (1.53 mmol) of HOBT, and 240.5 mg (1.53 mmol) of 2-(cyclohexylmethoxy)ethylamine in 10 mL of anhydrous DMF were added 293.2 mg (1.53 mmol) of WSC and 168 mL of NMM. The mixture was stirred for 23 h while allowed to warm up slowly to room temperature on its own. The reaction was quenched with 35 mL of $H_2O$ and the mixture was extracted with 3×50 mL of EtOAc. The combined organic layer was washed with 3×100 mL of $H_2O$ and 100 mL of brine, dried over $MgSO_4$, and concentrated. Flash chromatography with 4% MeOH-$CH_2Cl_2$ furnished 417.3 mg (94%) of yellow sticky solid: mp 121°–124° C.; $^1$H NMR (CDCl$_3$) δ 9.03 (s, 1H), 8.87 (d, J=3.9 Hz, 1H), 8.31 (s, 1H), 8.20 (d, J=8.3 Hz, 2H), 8.19 (buried, 1H), 7.94 (d, J=8.3 Hz, 2H), 7.53 (dd, J=7.9, 4.9 Hz, 1H), 7.52 (br t, 1H), 3.63 (m, 4H), 3.31 (d, J=6.4 Hz, 2H), 1.84–0.97 (m, 10H); FDMS 433 (M+). Anal. ($C_{25}H_{27}N_3O_4$), C, H, N.

Example 26-E
2-[4-(3-Pyridylcarbonyl)phenyl]oxazole-4-[N-[3-(1-cyclohexylethoxy)propyl]]carboxamide:

Prepared similarly as above from 200.0 mg (0.49 mmol) of the crude oxazole acid and 90.2 mg (0.49 mmol) of 3-(1-cyclohexylethoxy)propylamine (80%): $^1$H NMR (CDCl$_3$) δ 9.01 (br s, 1H), 8.84 (br s, 1H), 8.28 (s, 1H), 8.19 (d, J=8.4 Hz, 2H), 8.17 (buried, 1H), 7.91 (d, J=8.3 Hz, 2H), 7.60 (br t, 1H), 7.49 (dd, J=7.7, 4.9 Hz, 1H), 3.58 (m, 4H), 3.15 (dq, J=6.2, 6.2 Hz, 1H), 1.90–1.43 (m, 8H), 1.26–1.02 (m, 5H), 1.14 (d, J=6.3 Hz, 3H); FDMS 462 (M+1). Anal. ($C_{27}H_{31}N_3O_4$) C, H, N.

Example 27-E
2-[4-(3-Pyridylcarbonyl)phenyl]oxazole-4-[N-(3-morpholinopropyl)]carboxamide:

As above from 698.3 mg (1.70 mmol) of the crude oxazole acid and 0.30 mL (2.04 mmol) of 3-morpholinopropylamine (69%): mp 178°–180° C.; $^1$H NMR (CDCl$_3$) δ 9.00 (d, J=1.8 Hz, 1H), 8.84 (dd, J=4.8, 1.4 Hz, 1H), 8.32 (br s, 1H), 8.29 (s, 1H), 8.18 (d, J=8.3 Hz, 2H), 8.14 (dt, J=8.0, 1.9 Hz, 1H), 7.94 (d, J=8.3 Hz, 2H), 7.43 (dd, J=8.0, 4.5 Hz, 1H), 3.86 (t, J=4.6 Hz, 4H), 3.58 (dt, J=6.1, 5.8 Hz, 2H), 2.55 (m, 6H), 1.82 (tt, J=6.0, 6.0 Hz, 2H); FDMS 420 (M+). Anal. ($C_{23}H_{24}N_4O_4$) C, H, N.

Example 28-E
2-[4-(3-Pyridylcarbonyl)phenyl]oxazole-4-[N-[2-(tetrahydropyran-2-ylmethoxy)ethyl]]-carboxamide:

As above from 419.0 mg (1.02 mmol) of the crude oxazole acid and 243.5 mg (1.53 mmol) of 2-((±)-tetrahydropyran-2-methoxy)ethylamine (89%): mp 111°–113° C.; $^1$H NMR (CDCl$_3$) δ 9.03 (s, 1H), 8.87 (d, J=4.3 Hz, 1H), 8.31 (s, 1H), 8.21 (d, J=8.4 Hz, 2H), 8.20 (buried, 1H), 7.94 (d, J=8.3 Hz, 2H), 7.53 (dd, J=11.8, 7.0 Hz, 1H), 7.50 (buried, 1H), 4.05 (br dt, J=11.4, 1.9 Hz, 1H), 3.69 (m, 3H), 3.50 (m, 5H), 1.86 (m, 1H), 1.55 (m, 4H), 1.39 (m, 1H); FDMS 436 (M+1). Anal. ($C_{24}H_{25}N_3O_5$) C, H, N.

Example 29-E
2-[4-(3-Pyridylcarbonyl)phenyl]oxazole-4-[N-(2-phenoxyethyl)]carboxamide:

As above from 366.4 mg (0.89 mmol) of the crude oxazole acid and 122.3 mg (0.89 mmol) of 2-phenoxyethylamine (94%): $^1$H NMR (CDCl$_3$) δ 8.97 (s, 1H), 8.80 (d, J=4.1 Hz, 1H), 8.29 (s, 1H), 8.14 (d, J=8.3 Hz, 2H), 8.12 (buried, 1H), 7.88 (d, J=8.2 Hz, 2H), 7.52 (distorted t, J=~5.9 Hz, 1H), 7.44 (dd, J=7.9, 5.0 Hz, 1H), 7.25 (dd, J=8.3, 7.5 Hz, 2H), 6.93 (m, 3H), 4.13 (t, J=5.1 Hz, 2H), 3.85 (dt, J=5.4, 5.4 Hz, 2H); FDMS 413 (M+). Anal. ($C_{24}H_{19}N_3O_4$) H, N; C: calcd, 69.73; found, 70.29.

Example 30-E
2-[4-(3-Pyridylcarbonyl)phenyl]oxazole-4-[N-(4-phenoxybutyl)]carboxamide:

As above from 200 mg (0.49 mmol) of the crude oxazole acid and 80.4 mg (0.49 mmol) of 4-phenoxybutylamine (84%): $^1$H NMR (CDCl$_3$) δ 9.01 (s, 1H), 8.84 (d, J=3.9 Hz, 1H), 8.29 (s, 1H), 8.16 (d, J=8.3 Hz, 2H), 8.16 (buried, 1H), 7.91 (d, J=8.4 Hz, 2H), 7.50 (dd, J=7.9, 4.9 Hz, 1H), 7.26 (dd, J=8.2, 7.6 Hz, 2H), 7.19 (br t, 1H), 6.92 (m, 3H), 4.02 (t, J=5.7 Hz, 2H), 3.55 (dt, J=6.4, 6.3 Hz, 2H), 1.89 (m, 4H); FDMS 441 (M+). Anal. ($C_{26}H_{23}N_3O_4$) C, H, N.

Example 31-E
2-[4-(3-Pyridylcarbonyl)phenyl]oxazole-4-[N-(5-phenoxypentyl)]carboxamide:

As above from 295.8 mg (0.72 mmol) of the crude oxazole acid and 129.0 mg (0.72 mmol) of 5-phenoxypentylamine (82%): mp 107°–110° C.; $^1$H NMR (CDCl$_3$) δ 9.01 (s, 1H), 8.85 (br d, J=3.9 Hz, 1H), 8.29 (s, 1H), 8.19 (d, J=8.3 Hz, 2H), 8.16 (buried dt, 1H), 7.92 (d, J=8.4 Hz, 2H), 7.50 (dd, J=7.9, 4.9 Hz, 1H), 7.26 (m, 2H), 7.08 (t, J=5.8 Hz, 1H), 6.90 (m, 3H), 3.98 (t, J=6.3 Hz, 2H), 3.50 (dt, J=6.6, 6.6 Hz, 2H), 1.90–1.57 (m, 6H); FDMS 455 (M+). Anal. (C$_{27}$H$_{25}$N$_3$O$_4$) C, H, N.

Example 32-E
2-[4-(3-Pyridylcarbonyl)phenyl]oxazole-4-[N-[2-(benzyloxy)ethyl]]carboxamide: As above from 500 mg (1.22 mmol) of the crude oxazole acid and 275.9 mg (1.82 mmol) of 2-(benzyloxy)ethylamine (76%): mp 133°–136° C.; $^1$H NMR (CDCl$_3$) δ 9.01 (s, 1H), 8.85 (br d, J=3.8 Hz, 1H), 8.29 (s, 1H), 8.21 (d, J=8.3 Hz, 2H), 8.15 (dt, J=7.9, 1.7 Hz, 1H), 7.93 (d, J=8.3 Hz, 2H), 7.49 (dd, J=8.0, 4.9 Hz, 1H), 7.43 (br s, 1H), 7.34 (m, 5H), 4.59 (s, 2H), 3.68 (s, 4H); FDMS 427 (M+). Anal. (C$_{25}$H$_{21}$N$_3$O$_4$) C, H, N.

Example 33-E
2-[4-(3-Pyridylcarbonyl)phenyl]oxazole-4-[N-[3-(4-methoxyphenyl)propyl]]carboxamide:

As above from 500 mg (1.22 mmol) of the crude oxazole acid and 301.5 mg (1.82 mmol) of 3-(4-methoxyphenyl)propylamine (77%): $^1$H NMR (CDCl$_3$) δ 9.00 (s, 1H), 8.84 (br d, J=3.4 Hz, 1H), 8.28 (s, 1H), 8.18 (d, J=8.2 Hz, 2H), 8.16 (buried, 1H), 7.92 (d, J=8.2 Hz, 2H), 7.48 (dd, J=7.6, 4.9 Hz, 1H), 7.13 (d, J=8.4 Hz, 2H), 7.04 (br t, 1H), 6.83 (d, J=8.4 Hz, 2H), 3.76 (s, 3H), 3.48 (dt, J=6.7, 6.7 Hz, 2H), 2.67 (t, J=7.5 Hz, 2H), 1.95 (tt, J=7.3, 7.2 Hz, 2H); FDMS 441 (M+). Anal. (C$_{26}$H$_{23}$N$_3$O$_4$) C, H, N.

Example 34-E
2-[4-(3-Pyridylcarbonyl)phenyl]oxazole-4-[N-(3-ethoxypropyl)]carboxamide: As above from 400 mg (0.97 mmol) of the crude oxazole acid and 175 mL (1.46 mmol) of 3-ethoxypropylamine (49%): mp 82°–85° C.; $^1$H NMR (CDCl$_3$) δ 9.01 (s, 1H), 8.84 (d, J=4.1 Hz, 1H), 8.28 (s, 1H), 8.19 (d, J=8.3 Hz, 2H), 8.15 (buried, 1H), 7.92 (d, J=8.3 Hz, 2H), 7.66 (br s, 1H), 7.49 (dd, J=7.8, 4.9 Hz, 1H), 3.57 (m, 6H), 1.91 (tt, J=6.0, 5.8 Hz, 2H), 1.30 (t, J=7.0 Hz, 3H); FDMS 379 (M+). Anal. (C$_{21}$H$_{21}$N$_3$O$_4$) C, H, N.

Example 35-E
2-[4-(3-Pyridylcarbonyl)phenyl]oxazole-4-[N-[3-(2-methoxyethoxy)propyl]]carboxamide:

As above from 400 mg (0.97 mmol) of the crude oxazole acid and 194.4 mg (1.46 mmol) of 3-(methoxyethoxy)propylamine (76%): $^1$H NMR (CDCl$_3$) δ 9.00 (s, 1H), 8.83 (br d, 1H), 8.30 (s, 1H), 8.20 (d, 2H), 8.18 (buried, 1H), 7.93 (d, 2H), 8.27 (m, 2H), 3.60 (m, 8H), 3.38 (s, 3H), 1.92 (m, 2H); FDMS 409 (M+).

F. Acids of Formula I were prepared from the ketones of Formula IIIa using a similar procedure to that described above at Example 18-G. In one preparation both the E-isomer (Example 25A) and the Z-isomer (Example 25B) were isolated and characterized.

Example 25A-F
(E)-7-[4-[4-[[[2-(Cyclohexylmethoxy)ethyl]amino] carbonyl]-2-oxazolyl]phenyl]-7-(3-pyridyl)hept-6-enoic Acid:

Prepared as above from 404.5 mg (0.93 mmol) of the pyridyl ketone and 846.7 mg (1.87 mmol) of the Wittig salt. Preparative HPLC with MeOH-AcOH-CH$_2$Cl$_2$ (3:1:96) gave in 87% yield a mixture of Wittig product (E/Z=~6.1:1) from which 266.7 mg (53.7%) of (E)-isomer was isolated cleanly: mp 49°–56° C.; $^1$H NMR (CDCl$_3$) δ 8.63 (br s, 1H), 8.50 (br s, 1H), 8.28 (s, 1H), 8.07 (d, J=8.0 Hz, 2H), 7.49 (distorted br d, J=7.0 Hz, 2H), 7.29 (d, J=7.9 Hz, 2H), 7.29 (buried, 1H), 6.23 (t, J=7.4 Hz, 1H), 3.64 (m, 4H), 3.31 (d, J=6.4 Hz, 2H), 2.35 (dd, J=7.1, 6.5 Hz, 2H), 2.23 (ddd, J=7.3, 7.1, 6.8 Hz, 2H), 1.83–0.92 (m, 15H); FDMS 532 (M+1). Anal. (C$_{31}$H$_{37}$N$_3$O$_5$) C, H, N.

Example 25B-F
(Z)-7-[4-[4-[[[2-(Cyclohexylmethoxy)ethyl]amino] carbonyl]-2-oxazolyl]phenyl]-7-(3-pyridyl)hept-6-enoic Acid:

Prepared as above from 404.5 mg (0.93 mmol) of the pyridyl ketone and 846.7 mg (1.87 mmol) of the Wittig salt. Preparative HPLC with MeOH-AcOH-CH$_2$Cl$_2$ (3:1:96) gave in 87% yield a mixture of Wittig product (E/Z=~6.1:1) from which 48.0 mg (9.7%) of (Z)-isomer was isolated cleanly: mp 52°–59° C.; FDMS 532 (M+1). Anal. (C$_{31}$H$_{37}$N$_3$O$_5$) C, H, N. 99.7% pure by HPLC.

Example 26-F
(E)-7-[4-[4-[[[3-(1-Cyclohexylethoxy)propyl]amino] carbonyl]-2-oxazolyl]phenyl]-7-(3-pyridyl)hept-6-enoic Acid:

Prepared as above from 164.5 mg (0.36 mmol) of the pyridyl ketone and 323.4 mg (0.71 mmol) of the Wittig salt. Flash chromatography with EtOAc-MeOH-AcOH-CH$_2$Cl$_2$ (80:3:1:16) gave 98.7 mg (50%) of the product (E/Z=96:4 by HPLC analysis): mp 80°–85° C.; $^1$H NMR (CDCl$_3$) δ 8.57 (d, 1H), 8.46 (d, J=4.1 Hz, 1H), 8.24 (s, 1H), 8.04 (d, J=8.1 Hz, 2H), 7.59 (t, J=5.5 Hz, 1H), 7.41 (br d, J=8.0 Hz, 1H), 7.25 (d, J=8.1 Hz, 2H), 7.20 (m, 1H), 6.16 (t, J=7.4 Hz, 1H), 3.57 (m, 4H), 3.13 (dq, J=6.2, 6.2 Hz, 1H), 2.29 (dd, J=7.1, 6.8 Hz, 2H), 2.17 (ddd, J=7.3, 7.1, 6.9 Hz, 2H), 1.87 (m, 3H), 1.69–1.40 (m, 10H), 1.24–0.95 (m, 3H), 1.12 (d, J=6.0 Hz, 3H); FDMS 560 (M+1). Anal. (C$_{33}$H$_{41}$N$_3$O$_5$.0.8H$_2$O) C, H, N.

Example 27-F
(E)-7-[4-[4-[[(3-Morpholinopropyl)amino]carbonyl]-2-oxazolyl]phenyl]-7-(3-pyridyl)hept-6-enoic Acid:

Prepared as above from 464.9 mg (1.11 mmol) of the pyridyl ketone and 1.00 g (2.21 mmol) of the Wittig salt. Flash chromatography with 15% MeOH-CH$_2$Cl$_2$ afforded 526.0 mg (92%) of the product (E/Z=~4:1 by $^1$H NMR): $^1$H NMR (DMSO) δ 8.66 (s, 1H), 8.52(m, 1H), 8.40 (dd, J=4.5, 1.1 Hz, 1H), 8.36 (d, J=1.9 Hz, 1H), 8.01 (d, J=8.2 Hz, 2H), 7.47 (m, 2H), 7.29 (d, J=8.1 Hz, 2H), 6.20 (t, J=7.4 Hz, 1H), 3.57 (br t, J=4.4 Hz, 4H), 3.28 (br dt, J=~6.2, 5.8 Hz, 2H), 2.30 (br s, 6H), 2.02 (m, 4H), 1.63 (br t, J=6.6 Hz, 2H), 1.40 (m, 4H); FDMS 519 (M+1). 97.5% pure by HPLC.

Example 28-F
(±)-(E)-7-[4-[4-[[[2-(Tetrahydropyran-2-ylmethoxy)ethyl]amino]carbonyl]-2-oxazolyl]-phenyl]-7-(3-pyridyl)hept-6-enoic Acid:

Prepared as above from 376.4 mg (0.86 mmol) of the (±)-pyridyl ketone and 790.6 mg (1.73 mmol) of the Wittig salt. Preparative HPLC with MeOH-AcOH-CH$_2$Cl$_2$ (4:1:95) gave in ~92% yield a mixture of Wittig product (E/Z=~96:4) from which 320.9 mg (70%) of (±)-(E)-heptenoic acid was isolated cleanly: mp 68°–73° C.; $^1$H NMR (CDCl$_3$) δ 8.61 (br s, 1H), 8.49 (br s, 1H), 8.28 (s, 1H), 8.06 (d, J=8.1 Hz, 2H), 7.52 (br s, 1H), 7.46 (br d, J=8.0 Hz, 1H), 7.28 (d, 2H), 7.27 (buried, 1H), 6.21 (t, J=7.4 Hz, 1H), 4.04 (dt, J=13.3, 1.9 Hz, 1H), 3.69 (br s, 4H), 3.50 (m, 5H), 2.33 (dd, J=7.1, 6.7 Hz, 2H), 2.21 (ddd, J=7.2, 7.0, 6.7 Hz, 2H), 1.89–1.26 (m, 1OH); FDMS 534 (M+1). Anal. ($C_{30}H_{35}N_3O_6$.0.25$C_2H_4O_2$) C, H, N.

Example 29-F
(E)-7-[4-[4-[[(2-Phenoxyethyl)amino]carbonyl]-2-oxazolyl]phenyl]-7-(3-pyridyl)hept-6-enoic Acid:

Prepared as above from 337.8 mg (0.86 mmol) of the pyridyl ketone and 742 mg (1.63 mmol) of the Wittig salt. Flash chromatography with MeOH-AcOH-CH$_2$Cl$_2$ (3:2:95) gave in ~92% yield a mixture of Wittig product (E/Z= ~7.7:1) from which 326.5 mg (78%) of (E)-heptenoic acid was isolated cleanly: mp 61°–64° C.; $^1$H NMR (CDCl$_3$) δ 8.57 (d, J=1.7 Hz, 1H), 8.47 (d, J=4.1 Hz, 1H), 8.28 (s, 1H), 8.05 (d, J=8.2 Hz, 2H), 7.52 (t, J=5.7 Hz, 1H), 7.45 (d, J=8.0 Hz, 1H), 7.25 (m, 5H), 6.94 (d, J=8.2 Hz, 2H), 6.94 (buried, 1H), 6.18 (t, J=7.4 Hz, 1H), 4.15 (t, J=5.0 Hz, 2H), 3.87 (dt, J=5.4, 5.3 Hz, 2H), 2.31 (dd, J=7.1, 6.7 Hz, 2H), 2.19 (ddd, J=7.3, 7.1, 6.9 Hz, 2H), 1.67–1.51 (m, 4H); FDMS 512 (M+1). Anal. ($C_{30}H_{29}N_3O_5$) C, H, N.

Example 30-F
(E)-7-[4-[4-[[(4-Phenoxybutyl)amino]carbonyl]-2-oxazolyl]phenyl]-7-(3-pyridyl)hept-6-enoic Acid:

Prepared as above from 159.3 mg (0.36 mmol) of the pyridyl ketone and 327.5 mg (0.72 mmol) of the Wittig salt. Flash chromatography with EtOAc-MeOH-AcOH-CH$_2$Cl$_2$ (80:3:1:16) furnished 164.6 mg (85%) of a white fluffy solid (E/Z=97:3 by HPLC analysis): $^1$H NMR (CDCl$_3$) δ 8.57 (d, J=1.0 Hz, 1H), 8.46 (d, J=4.1 Hz, 1H), 8.25 (s, 1H), 8.02 (d, J=8.2 Hz, 2H), 7.42 (br d, J=7.9 Hz, 2H), 7.23 (m, 5H), 6.92 (buried, 1H), 6.89 (d, J=8.6 Hz, 2H), 6.16 (t, J=7.4 Hz, 1H), 4.00 (dd, J=5.8, 5.5 Hz, 2H), 3.54 (ddd, J=6.5, 6.3, 6.1 Hz, 2H), 2.29 (dd, J=7.1, 6.7 Hz, 2H), 2.17 (ddd, J=7.2, 7.1, 7.0 Hz, 2H), 1.87 (m, 4H), 1.65–1.48 (m, 4H); FDMS 540 (M+1). 98.7% pure by HPLC.

Example 31-F
(E)-7-[4-[4-[[(5-Phenoxypentyl)amino]carbonyl]-2-oxazolyl]phenyl]-7-(3-pyridyl)hept-6-enoic Acid:

Prepared as above from 254.1 mg (0.56 mmol) of the pyridyl ketone and 506.2 mg (1.12 mmol) of the Wittig salt. Flash chromatography with EtOAc-MeOH-AcOH-CH$_2$Cl$_2$ (82:2:1:15) yielded 273.3 mg (89%) of a white fluffy sold (E/Z=95:5 by HPLC analysis): mp 42°–48° C.; $^1$H NMR (CDCl$_3$) δ 8.59 (s, 1H), 8.48 (d, J=4.4 Hz, 1H), 8.26 (s, 1H), 8.05 (d, J=8.1 Hz, 2H), 7.52 (br dd, J=7.9, 2.0 Hz, 1H), 7.46 (br dd, J=7.6, 2.6 Hz, 1H), 7.25 (m, 4H), 7.10 (t, J=6.0 Hz, 1H), 6.93 (buried, 1H), 6.88 (d, J=7.9 Hz, 2H), 6.22 (t, J=7.4 Hz, 1H), 3.96 (dd, J=6.4, 6.2 Hz, 2H), 3.49 (ddd, J=6.7, 6.6, 6.5 Hz, 2H), 2.32 (dd, J=7.2, 6.8 Hz, 2H), 2.20 (ddd, J=7.3, 7.1, 7.0 Hz, 2H), 1.89–1.51 (m, 10H:); FDMS 554(M+1). Anal. ($C_{33}H_{35}N_3O_5$) C, H, N.

Example 32-F
(E)-7-[4-[4-[[[2-(Benzyloxy)ethyl]amino]carbonyl]-2-oxazolyl]phenyl]-7-(3-pyridyl)hept-6-enoic Acid:

Prepared as above from 375.3 mg (0.88 mmol) of the pyridyl ketone and 796.8 mg (1.76 mmol) of the Wittig salt. Preparative HPLC with MeOH-AcOH-CH$_2$Cl$_2$ (4:1:95) yielded 266.2 mg (58%) of the pure (E)-heptenoic acid as a white fluffy sold: mp 48°–55° C.; $^1$H NMR (CDCl$_3$) δ 8.60 (br s, 1H), 8.48 (br s, 1H), 8.26 (s, 1H), 8.06 (d, J=8.2 Hz, 2H), 7.48 (br s, 1H), 7.46 (br s, 1H), 7.38–7.25 (m, 6H), 7.27 (d, J=8.2 Hz, 2H), 6.20 (t, J=7.4 Hz, 1H), 4.57 (s, 2H), 3.67 (s, 4H), 2.32 (dd, J=7.1, 6.8 Hz, 2H), 2.20 (ddd, J=7.3, 7.2, 6.8 Hz, 2H), 1.68–1.52 (m, 4H); FDMS 526 (M+1). Anal. ($C_{31}H_{31}N_3O_5$) C, H, N.

Example 33-F
(E)-7-[4-[4-[[[3-(4-Methoxyphenyl)propyl]amino]carbonyl]-2-oxazolyl]phenyl]-7-(3-pyridyl)hept-6-enoic Acid:

Prepared as above from 410.6 mg (0.93 mmol) of the pyridyl ketone and 844.0 mg (1.86 mmol) of the Wittig salt. Flash chromatography with EtOAc-MeOH-AcOH-CH$_2$Cl$_2$ (82:2:1:15) furnished 369.6 mg (74%) of a white fluffy sold (E/Z=94:6 by HPLC analysis): mp 49°–58° C.; $^1$H NMR (CDCl$_3$) δ 8.59 (s, 1H), 8.48 (br d, J=4.1 Hz, 1H), 8.25 (s, 1H), 8.05 (d, J=8.3 Hz, 2H), 7.52 (br dd, J=8.1, 1.5 Hz, 1H), 7.27 (d, J=8.2 Hz, 2H), 7.27 (buried, 1H), 7.12 (d, J=8.6-Hz, 2H), 7.09 (buried, 1H), 6.82 (d, J=8.6 Hz, 2H), 6.22 (t, J=7.4 Hz, 1H), 3.76 (s, 3H), 3.48 (ddd, J=6.8, 6.7, 6.6 Hz, 2H), 2.67 (dd, J=7.6, 7.5 Hz, 2H), 2.32 (dd, J=7.2, 6.8 Hz, 2H), 2.20 (ddd, J=7.3, 7.2, 7.0 Hz, 2H), 1.93 (m, 2H), 1.68–1.51 (m, 4H); FDMS 540 (M+1). Anal. ($C_{32}H_{33}N_3O_5$), C, H, N.

Example 34-F
(E)-7-[4-[4-[[(3-Ethoxypropyl)amino]carbonyl]-2-oxazolyl]phenyl]-7-(3-pyridyl)hept-6-enoic Acid:

Prepared as above from 165.4 mg (0.44 mmol) of the pyridyl ketone and 395.6 mg (0.87 mmol) of the Wittig salt. Preparative HPLC with MeOH-AcOH-CH$_2$Cl$_2$ (2:1:97) furnished 94.8 mg (46%) of the pure (E)-heptenoic acid: mp 67°–72° C.; $^1$H NMR (CDCl$_3$) δ 8.60 (s, 1H), 8.48 (br s, 1H), 8.25 (s, 1H), 8.05 (d, J=8.2 Hz, 2H), 7.62 (distorted t, J=~5.3 Hz, 1H), 7.43 (br d, J=7.8 Hz, 1H), 7.28 (buried, 1H), 7.26 (d, 2H), 6.22 (t, J=7.4 Hz, 1H), 3.50 (m, 6H), 2.30 (ddd, J=7.1, 7.1, 6.9 Hz, 2H), 2.20 (ddd, J=7.6, 7.2, 6.9 Hz, 2H), 1.90 (tt, J=6.1, 6.1 Hz, 2H), 1.64–1.54 (m, 4H), 1.28 (t, J=7.0 Hz, 3H); FDMS 478 (M+1). Anal. ($C_{27}H_{31}N_3O_5$.0.6CH$_4$O.0.8H$_2$O) C, H, N.

Example 35-F
(E)-7-[4-[4-[[[3-(2-Methoxyethoxy)propyl]amino]carbonyl]-2-oxazolyl]phenyl]-7-(3-pyridyl)hept-6-enoic Acid:

Prepared as above from 286.2 mg (0.70 mmol) of the pyridyl ketone and 634.3 mg (1.40 mmol) of the Wittig salt. Flash chromatography with MeOH-AcOH-CH$_2$Cl$_2$ (6:1:93) furnished 293.8 mg (83%) of a semi solid (E/Z=8.8:1 by HPLC analysis): $^1$H NMR (CDCl$_3$) δ 8.59 (s, 1H), 8.47 (br d, J=3.4 Hz, 1H), 8.25 (s, 1H), 8.06 (d, J=8.1 Hz, 2H), 7.46 (m, 2H), 7.27 (d, 2H), 7.25 (buried, 1H), 6.19 (t, J=7.5 Hz, 1H), 3.59 (m, 8H), 3.38 (s, 3H), 2.31 (dd, J=7.1, 6.8 Hz, 2H), 2.20 (ddd, J=7.4, 7.2, 6.7 Hz, 2H), 1.93 (tt, J=6.2, 6.1 Hz, 2H), 1.68–1.52 (m, 4H); FDMS 508 (M+1). Anal ($C_{28}H_{33}N_3O_6$) C, H, N.

Example 36
(E)-5-[4-[4-[[(4-Cyclohexylbutyl)amino]carbonyl]-2-oxazolyl]phenyl]-5-(3-pyridyl)pent-4-enoic Acid:

Prepared as above from 150.0 mg (0.35 mmol) of the pyridyl ketone, 298.4 mg (0.69 mmol) of (3-carboxypropyl)triphenylphosphonium bromide, and 1.39 mL (1.39 mmol) of 1.0M t-BuOK in 1.5 mL of THF at 0° C. for 2 h. Flash chromatography with MeOH-ACOH-CH$_2$Cl$_2$ (4:1:95) furnished 93.0 mg (53%) of the Wittig product (E/Z=86:14 by HPLC analysis): $^1$H NMR (CDCl$_3$) δ 8.68 (br s, 1H), 8.51 (br dd, J=4.1, 1.0 Hz, 1H), 8.29 (s, 1H), 8.09 (d, J=8.2 Hz, 2H), 7.51 (br d, J=8.0 Hz, 1H), 7.32 (buried, 1H), 7.30 (d, J=8.3 Hz, 2H), 7.11 (distorted t, J=~5.8 Hz, 1H), 6.34 (distorted br t, 1H), 3.47 (dt, J=6.8, 6.5 Hz, 2H), 2.53 (br s, 4H), 1.78–0.83 (m, 17H); FDMS 502 (M+1). Anal. ($C_{30}H_{35}N_3O_4$.0.54$C_2H_4O_2$) C, H, N.

Example 37
(E)-8-[4-[4-[[(4-Cyclohexylbutyl)amino]carbonyl]-2-oxazolyl]phenyl]-8-(3-pyridyl)oct-7-enoic Acid:

Prepared as above from 156.3 mg (0.36 mmol) of the pyridyl ketone, 341.4 mg (0.72 mmol) of (6-carboxyhexyl)-triphenylphosphonium bromide, and 1.45 mL (1.45 mmol) of 1.0M t-BuOK in 1.5 mL of THF at 0° C. for 2 h. Flash chromatography with MeOH-AcOH-CH$_2$Cl$_2$ (4:1:95) yielded 150.5 mg (76%) of the product (E/Z=91:9 by HPLC analysis): $^1$H NMR (CDCl$_3$) δ 8.49 (br s, 1H), 8.48 (br s, 1H), 8.26 (s, 1H), 8.06 (d, J=8.2 Hz, 2H), 7.53 (br d, J=7.6 Hz, 1H), 7.27 (d, J=8.3 Hz, 2H), 7.27 (buried, 1H), 7.08 (dd, J=6.3, 5.7 Hz, 1H), 6.21 (t, J=7.5 Hz, 1H), 3.44 (dt, J=6.7, 6.7 Hz, 2H), 2.33 (dd, J=7.2, 7.2 Hz, 2H), 2.18 (m, 2H), 6.70–0.81 (m, 23H); FDMS 544 (M+1). Anal. (C$_{33}$H$_{41}$N$_3$O$_4$), C, H, N.

Example 38

(E)-6-[4-[4-[[(4-Cyclohexylbutyl)amino]carbonyl]-2-oxazolyl]phenyl]-6-(3-pyridyl)hex-5-enoic Acid:

Prepared as above from 150.0 mg (0.35 mmol) of the pyridyl ketone, 308.2 mg (0.70 mmol) of (4-carboxybutyl) triphenylphosphonium bromide, and 1.4 mL (1.4 mmol) of 1.0M t-BuOK in 1.5 mL of THF at 0° C. for 1.5 hr. Flash chromatography followed by preparative HPLC with MeOH-AcOH-CH$_2$Cl$_2$ (3.5:1.5:95) furnished 107.9 mg 60.2%) of (E)-hexenoic acid and 35.4 mg (19.8%) of (Z)-hexenoic acid (E/Z=3:1). The title (E)-isomer was characterized as follows: mp 86–90° C.; $^1$H NMR (CDCl$_3$) δ 8.55 (br s, 1H), 8.45 (d, J=4.7 Hz, 1H), 8.25 (s, 1H), 8.04 (d, J=8.1 Hz, 2H), 7.47 (d, J=8.0 Hz, 1H), 7.29 (d, J=8.2 Hz, 2H), 7.21 (m, 1H), 7.12 (distorted t, J=~5.1 Hz, 1H), 6.19 (t, J=7.5 Hz, 1H), 3.44 (dt, J=7.0, 6.7, Hz, 2H), 2.34 (t J=7.1 Hz, 2H), 2.25 (dt, J=7.4, 7.3 Hz, 2H), 1.68–0.82 (m, 19H); FDMS 516 (M+1). Anal. (C$_{31}$H$_{37}$N$_3$O$_4$) C, H, N.

Example 39

(Z)-6-[4-[4-[[(4-Cyclohexylbutyl)amino]carbonyl]-2-oxazolyl]phenyl]-6-(3-pyridyl)hex-5-enoic Acid:

The title (Z)-isomer from the above example was characterized as follows: mp 86°–88° C.; $^1$H NMR (CDCl$_3$) δ 6.29 (distorted t, J=~7.5 Hz, 1H) for olefinic proton; FDMS 516 (M+1).

Alternative Preparation of Example 38
(E)-6-[4-[4-[[(4-Cyclohexylbutyl)amino]carbonyl]-2-oxazolyl]phenyl]-6-(3-pyridyl)hex-5-enoic Acid A. Ethyl 2-(4-Hydroxyphenyl)oxazole-4-carboxylate A mixture of 25.0 g (182.3 mmol) of 4-hydroxybenzamide and 23.0 mL (182.3 mmol) of ethyl bromopyruvate was stirred and heated at 115° C. for 30 minutes. The mixture cooled to room temperature and sat under N$_2$ atmosphere overnight. Ethyl acetate (100 mL) was added and the mixture stirred for 1 hour. The solid oxazole (36.99 g, 158.6 mmol) was collected by suction filtration in 87% yield: $^1$H NMR (CDCl$_3$) δ 10.21 (broad s, 1H), 8.82 (s, 1H), 7.83 (d, J=8.7 Hz, 2H), 6.90 (d, J=8.7 Hz, 2H), 4.29 (q, 2H), 1.29 (t, 3H); IR (cm$^{-1}$) 3400, 3169, 1731, 1612, 1731, 1507, 1444; FDMS 233. Anal. (C$_{12}$H$_{11}$NO$_4$) C, H, N.

B. Ethyl 2-(4-Trifluoromethylsulfonyloxyphenyl)oxazole-4-carboxylate

A 25 mL 3-necked round bottomed flask was charged under N$_2$ atmosphere with the above phenol (751 mg, 3.2 mmol), 10 mL dry pyridine, and a stir bar, and cooled to 0° C. Triflic anhydride (1.0 g, 3.5 mmol) was added dropwise via cannula over 5 minutes. The reaction mixture warmed to room temperature and continued stirring for 16 hours. Ethyl acetate (10 mL) was added, and the solution was washed 4 times with saturated CuSO$_4$. Methylene chloride (5 mL) was added and the solution was washed twice with 5% sodium bicarbonate solution and brine. The combined organics were dried over MgSO$_4$. Filtration and solvent removal gave a yellow solid which was recrystallized from methanol to give 1.102 g (94%) of the triflate as a white solid: $^1$H NMR (CDCl$_3$) δ 8.28 (s, 1H), 8.19 (d, 2H), 7.37 (d, 2H), 4.40 (q, 2H), 1.38 (t, 3H); IR (cm$^{-1}$) 1732, 1431; FDMS 265. Anal. (C$_{13}$H$_{10}$F$_3$NO$_6$S) C, H, N.

C. N-(4-Cyclohexylbutyl)-2-(4-trifluoromethylsulfonyloxyphenyl)oxazole-4-carboxamide A 25 mL 3-necked round bottom flask was charged with 4-cyclohexylbutyl ammonium chloride (405.6 mg, 2.1 mmol) and 6 mL anhydrous toluene, and cooled to 0° C. under N$_2$ atmosphere. To this stirred suspension, trimethyl aluminum (1.1 mL of a 2M solution in toluene, 2.2 mmol) was added dropwise via syringe, the ice bath was removed, and the reaction continued stirring until gas evolution ceased.

A second 25 mL 3-necked round bottom flask was charged with the above ester (222 mg, 0.61 mmol) and 6 mL anhydrous toluene, and the mixture from the first flask was added via syringe. This stirred mixture was heated at 50° C. under nitrogen for 1 hour. After cooling to room temperature, the reaction was quenched with 1N HCl, diluted with 10 mL H$_2$O, and extracted twice with 25 mL portions of ethyl acetate. The combined extracts were dried over MgSO$_4$. Filtration and solvent removal gave an off-white solid which was recrystallized from 1-chlorobutane to give 273 mg (95%) of the title compound as a white solid: $^1$H NMR (CDCl$_3$) δ 8.28 (s, 1H), 8.16 (d, 2H), 7.43 (d, 2H), 7.01 (broad t, 1H), 3.46 (t, 1H), 3.44 (t, 1H), 1.66 (m, 7H), 1.41 (m, 2H), 1.22 (m, 6H), 0.89 (m, 2H); IR (cm$^{-1}$) 3420, 2026, 2854, 1667, 1599; FDMS 474. Anal. (C$_{21}$H$_{25}$F$_3$N$_2$O$_5$S) C, H, F. N, S.

D. tert-Butyl 6-[4-[4-[[(4-Cyclohexylbutyl)amino]carbonyl]-2-oxazolyl]phenyl]hex-5-ynoate A 2-necked 50 mL round bottom flask under nitrogen atmosphere was charged with the above triflate (963.2 mg, 2.03 mmol), tert-butyl hex-5-ynoate (1.06 g, 6.29 mmol), 10 mL of anhydrous dimethylformamide, and 2 mL of freshly distilled triethylamine. After stirring until the triflate had dissolved, bis(triphenylphosphine)palladium(II) chloride (71.2 mg, 0.102 mmol) was added. A reflux condenser was attached, and the system was evacuated and flushed with nitrogen two times. The reaction mixture was heated at 80° C. under nitrogen atmosphere for 18 hours. After cooling to room temperature, 10 mL water was added and the mixture was extracted three times with ethyl acetate. The combined extracts were washed three times with water and dried over MgSO$_4$. Filtration and solvent removal gave a reddish brown oil which was purified by radial chromatography (1% methanol in methylene chloride) to give 1.0121 g of the alkyne as an orange solid. This was further purified by recrystallization from hexane/ethyl acetate to give pale yellow crystals: $^1$H NMR (CDCl$_3$) δ 8.21 (s, 1H), 7.96 (d, 2H), 7.50 (d, 2H), 7.03 (broad t, 1H), 3.42 (t, 1H), 3.45 (t, 1H), 2.51 (t, 2H), 2.42 (t, 2H), 1.91 (m, 2H), 1.69 (m, 7H), 1.48 (s, 9H), 1.39 (m, 2H), 1.21 (m, 6H), 0.89 (m, 2H); IR (cm$^{-1}$) 3420, 2927, 2854, 1722, 1664; FDMS 492. Anal. (C$_{30}$H$_{40}$N$_2$O$_4$) C, H, N.

E. tert-Butyl (E)-6-[4-[4-[[(4-Cyclohexylbutyl)amino]carbonyl]-2-oxazolyl]phenyl]-6-iodohex-5-enoate A 2-necked 50 mL round bottom flask was charged under nitrogen atmosphere with a stir bar, the above alkyne (148.6 mg, 0.302 mmol), and tetrakis(triphenylphosphine)palladium(0) (17.4 mg, 0.0015 mmol). Anhydrous toluene (5 mL) was added via syringe, and the mixture was stirred until the two solids dissolved. A 2 mL solution of tributyltin hydride (0.392 mmol) in anhydrous toluene was added, and the reaction stirred at room temperature for 30 minutes. The solution was then transferred to a dry 50 mL round bottom flask and the toluene was removed in vacuo. The residue was dissolved in 10 mL anhydrous THF and the flask was cooled to 0° C. in an ice bath. A 10 mL solution of iodine (84.2 mg, 0.3318 mmol) in anhydrous THF was added dropwise via pressure equalizing addition funnel over 30 minutes. The ice bath was removed and the reaction stirred at room temperature for 2 hours. Saturated sodium bisulfite solution (50 mL) was added, and the organics were extracted three times with ethyl acetate. The combined extracts were dried over $MgSO_4$. Filtration and solvent removal gave a yellow oil which was purified by radial chromatography (2 mm plate, 10% ethyl acetate in hexanes) to give 193.6 mg of a pale yellow oil: $^1$H NMR (CDCl$_3$) δ 8.24 (s, 1H), 8.00 (d, 2H), 7.41 (d, 2H), 7.05 (broad t, 1H), 6.52 (t, 1H), 3.45 (q, 2H), 2.15 (q, 2H), 2.04 (q, 2H), 1.70 (m, 7H), 1.40 (m, 9H), 1.23 (m, 6H), 0.93 (m, 4H); IR (cm$^{-1}$) 2926, 2853, 1721, 1664, 1599. High Resolution MS Accurate mass calculated for $C_{30}H_{42}IN_2O_4$: 621.2189. Found: 621.2183.

F. tert-Butyl (E)-6-[4-[4-[[(4-Cyclohexylbutylamino]carbonyl]-2-oxazolyl]phenyl-6-(3-pyridyl)hex-5-enoate An oven-dried, 10 mL sealable reaction tube was charged with the above vinyl iodide (190.5 mg, 0.307 mmol), 3-(trimethylstannyl)pyridine (81.7 mg, 0.338 mmol), tetrakis(triphenylphosphine)palladium(0) (10.6 mg, 9.2×10$^{-3}$ mmol), a small stir bar, and 1.5 mL anhydrous dimethyl-formamide. The tube was evacuated and flushed with nitrogen three times. The tube was sealed, and heated at 90° C. for 2 hours. After the reaction cooled to room temperature, ethyl acetate (3 mL) was added and the solution was washed three times with water. The organic layer was dried over $MgSO_4$. Filtration and solvent removal gave a yellow/green oil which was purified by radial chromatography (2 mm plate, gradient system of 1% to 5% methanol in methylene chloride) to give the title compound as a bright yellow oil in 54% yield: $^1$H NMR (CDCl$_3$) δ 8.52 (s, 1H), 8.485 (d, 1H), 8.26 (s, 1H), 8.07 (d, 2H), 7.48 (d, 1H), 7.29 (d, 2H), 7.22 (dd, 1H), 7.06 (broad t, 1H), 6.16 (t, 1H), 3.45 (m, 2H), 2.21 (m, 5H), 1.78 (m, 9H), 1.40 (s, 9H), 1.23 (m, 7H), 0.87 (m, 2H); IR (cm$^{-1}$) 3880, 2926, 2853, 1720, 1664, 1598; MS FAB+ 572.5. Anal. ($C_{35}H_{45}N_3O_4$) C, H, N.

G. (E)-6-[4-[4-[[(4-Cyclohexylbutylamino]carbonyl]-2-oxazolyl]phenyl-6-(3-pyridyl)hex-5-enoic Acid The tert-butyl group was removed by stirring the above ester in a solution of 20% trifluoroacetic acid in methylene chloride overnight. The methylene chloride was removed in vacuo to afford the acid: FDMS 516 (M+1).

What is claimed is:

1. A compound of Formula I

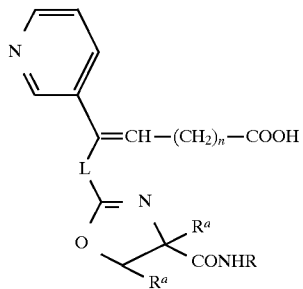

in either the E-form, the Z-form or a mixture thereof, wherein
n is 2, 3, 4 or 5;
L is ortho-, meta- or para-phenylene;
each $R^a$ is hydrogen or the two together form a double bond; and R is (3–12C)alkyl, (3–12C)alkenyl, (3–12C)alkynyl, 2-phenylcyclopropyl or $R^b$-(1∝6C)alkyl in which $R^b$ is (3–8C)cycloalkyl, phenyl, tetrahydropyranyl, morpholino, piperidino or pyrrolidino wherein a phenyl group of the radical R may bear a 4-substituent selected from halo, (1–2C)alkyl and (1–2C)alkoxy; a cyclohexyl group of the radical R may bear a 4-substituent selected from (1–2C)alkyl and (1–2C)alkoxy; and in which one or two methylene groups of a (3–12C)alkyl, (3–12C)alkenyl, (3–12C)alkynyl, or the alkyl portion of $R^b$-(1–6C)alkyl may be replaced by an oxy group; and further provided that at least two carbon atoms separate any oxygens or nitrogens in the residue —NHR;

or a pharmaceutically acceptable salt thereof.

2. The compound of Formula I, or a pharmaceutically acceptable salt thereof, as claimed in claim 1 wherein the double bond is of the E-form.

3. The compound of Formula I, or a pharmaceutically acceptable salt thereof, as claimed in claim 1 in which L is meta-phenylene or para-phenylene.

4. The compound of Formula I, or a pharmaceutically acceptable salt thereof, as claimed in claim 2 in which L is meta-phenylene or para-phenylene.

5. The compound of Formula I, or a pharmaceutically acceptable salt thereof, as claimed in claim 2 in which L is para-phenylene.

6. The compound of Formula I, or a pharmaceutically acceptable salt thereof, as claimed in claim 1 in which n is 3 or 4.

7. The compound of Formula I, or a pharmaceutically acceptable salt thereof, as claimed in claim 2 in which n is 3 or 4.

8. The compound of Formula I, or a pharmaceutically acceptable salt thereof, as claimed in claim 3 in which n is 3 or 4.

9. The compound of Formula I, or a pharmaceutically acceptable salt thereof, as claimed in claim 4 in which n is 3 or 4.

10. The compound of Formula I, or a pharmaceutically acceptable salt thereof, as claimed in claim 5 in which n is 3 or 4.

11. The compound or a pharmaceutically acceptable salt thereof, as claimed in claim 1 which is a compound of Formula Ia.

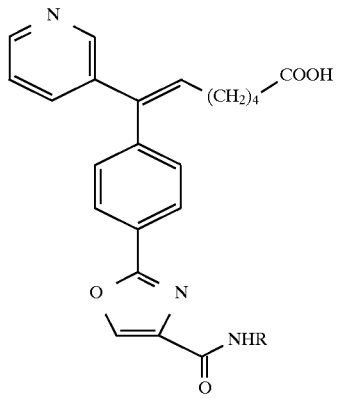

12. The compound or a pharmaceutically acceptable salt thereof, as claimed in claim 1 in which R is pentyl, 3-ethoxypropyl, 3-(2-methoxyethoxy)propyl, trans-2-phenylcyclopropyl, cyclopropylmethyl, 4-cyclohexylbutyl, 3-(4-methoxy-cyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy) propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)-ethyl or 3-morpholinopropyl.

13. The compound or a pharmaceutically acceptable salt thereof, as claimed in claim 2 in which R is pentyl, 3-ethoxypropyl, 3-(2-methoxyethoxy)propyl, trans-2-phenylcyclopropyl, cyclopropylmethyl, 4-cyclohexylbutyl, 3-(4-methoxy-cyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy) propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)-ethyl or 3-morpholinopropyl.

14. The compound or a pharmaceutically acceptable salt thereof, as claimed in claim 3 in which R is pentyl, 3-ethoxypropyl, 3-(2-methoxyethoxy)propyl, trans-2-phenylcyclopropyl, cyclopropylmethyl, 4-cyclohexylbutyl, 3-(4-methoxy-cyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy) propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)-ethyl or 3-morpholinopropyl.

15. The compound or a pharmaceutically acceptable salt thereof, as claimed in claim 6 in which R is pentyl, 3-ethoxypropyl, 3-(2-methoxyethoxy)propyl, trans-2-phenylcyclopropyl, cyclopropylmethyl, 4-cyclohexylbutyl, 3-(4-methoxy-cyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy) propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)-ethyl or 3-morpholinopropyl.

16. The compound or a pharmaceutically acceptable salt thereof, as claimed in claim 11 in which R is pentyl, 3-ethoxypropyl, 3-(2-methoxyethoxy)propyl, trans-2-phenylcyclopropyl, cyclopropylmethyl, 4-cyclohexylbutyl, 3-(4-methoxy-cyclohexyl)propyl, 2-(cyclohexyloxy)ethyl, 3-(cyclohexyloxy)propyl, 4-(cyclohexyloxy)butyl, 2-(cyclohexylmethoxy)ethyl, 3-(1-cyclohexylethoxy) propyl, benzyl, phenethyl, 2-phenoxyethyl, 3-phenoxypropyl, 4-phenoxybutyl, 5-phenoxypentyl, 2-(benzyloxy)ethyl, 3-(4-methoxyphenyl)propyl, 2-(tetrahydropyran-2-ylmethoxy)-ethyl or 3-morpholinopropyl.

17. The compound, or a pharmaceutically acceptable salt thereof, as claimed in claim 1 in which R is 4-cyclohexylbutyl.

18. The compound, or a pharmaceutically acceptable salt thereof, as claimed in claim 2 in which R is 4-cyclohexylbutyl.

19. The compound, or a pharmaceutically acceptable salt thereof, as claimed in claim 3 in which R is 4-cyclohexylbutyl.

20. The compound, or a pharmaceutically acceptable salt thereof, as claimed in claim 6 in which R is 4-cyclohexylbutyl.

21. The compound, or a pharmaceutically acceptable salt thereof, as claimed in claim 11 in which R is 4-cyclohexylbutyl.

22. The compound as claimed in claim 1 which is (E)-7-[4-[4-[[(4-cyclohexylbutyl)amino]carbonyl]-2-oxazolyl]-phenyl]-7-(3-pyridyl)hept-6-enoic acid, (E)-7-[3-[4-[[(4-cyclohexylbutyl)amino]carbonyl]-2-oxazolyl] phenyl]-7-(3-pyridyl)hept-6-enoic acid or (E)-7-[4-[4-[[(4-phenoxybutyl)-amino]carbonyl]-2-oxazolyl]phenyl]-7-(3-pyridyl)hept-6-enoic acid or a pharmaceutically acceptable salt thereof.

23. A pharmaceutically acceptable salt of the compound of Formula I as claimed in claim 1, which salt is made with a base which affords a pharmaceutically acceptable cation, selected from alkalai metal salts, alkaline earth metal salts, aluminum salts, ammonium salts, and salts made from physiologically acceptable organic bases.

24. The salt as claimed in claim 23 which is a potassium or sodium salt.

25. A pharmaceutical formulation comprising the compound of Formula I as claimed in claim 1 (or a prodrug thereof) or a pharmaceutically acceptable salt thereof, together with a suitable diluent or carrier.

26. A method for the treatment or prevention of a condition associated with excessive thromboxane $A_2$ activity which comprises administering to a mammal in need thereof an effective amount of the compound of Formula I, or a pharmaceutically acceptable salt thereof, as claimed in claim 1.

27. A process for preparing the compound of Formula I, or a pharmaceutically acceptable salt thereof, as claimed in claim 1 which comprises:

(A) decomposing an ester of Formula II,

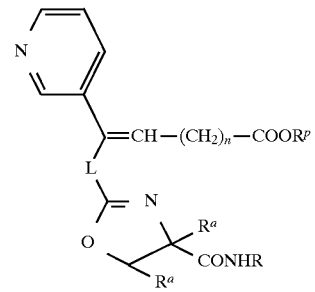

in which RP forms a carboxy-protecting ester group;

(B) condensing a ketone of Formula III

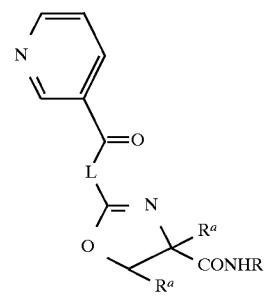

with a phosphorane of Formula IV

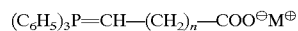

in which M is an alkali or alkaline earth metal, followed by acidification; or (C) for a compound of Formula I in which the two $R^a$ groups together form a double bond (an oxazole), dehydrogenating a corresponding compound of Formula I in which each $R^a$ is hydrogen (an oxazoline);

whereafter, for any of the above procedures, when a pharmaceutically acceptable salt of a compound of Formula I is required, it is obtained by reacting the acid of Formula I with a physiologically acceptable base or by reacting a basic compound of Formula I with a physiologically acceptable acid or by any other conventional procedure;

and wherein, unless otherwise specified, the values and groups n, L, $R^a$ and R and their components have any of the values defined in claim 1.

28. An ester of Formula II,

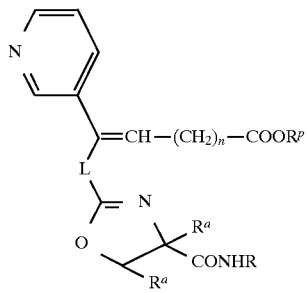

II in which $R^p$ forms a carboxy-protecting group consisting of methyl, ethyl, tert-butyl, benzyl, methoxymethyl and trimethylsilyl, and wherein the values and groups n, L, $R^a$ and R have any of the values defined in claim 1.

29. The compound as claimed in claim 28 which is a compound of Formula IIa

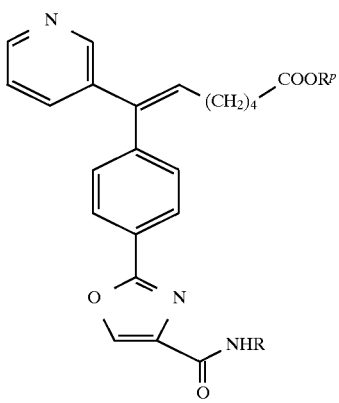

IIa

30. The compound as claimed in claim 28 in which the alcohol of formula $R^pOH$ is a pharmaceutically acceptable alcohol and the ester of Formula II or Formula IIa is metabolically hydrolyzable.

31. The compound as claimed in claim 29 in which the alcohol of formula $R^pOH$ is a pharmaceutically acceptable alcohol and the ester of Formula II or Formula IIa is metabolically hydrolyzable.

* * * * *

UNITED STATES PATENT AND TRADEMARK OFFICE
CERTIFICATE OF CORRECTION

PATENT NO. : 5,849,766
DATED : December 15, 1998
INVENTOR(S) : Joseph Anthony Jakubowski, et al It is certified that error appears in the above-indentified patent and that said Letters Patent is hereby corrected as shown below:

In column 52, lines 27 through 67, and in Column 53, lines 1 through 9, the entirety of Claim 27 should be deleted because the claim was withdrawn from prosecution following a restriction requirement and was not examined nor allowed.

Signed and Sealed this

Twelfth Day of October, 1999

*Attest:*

Q. TODD DICKINSON

*Attesting Officer*     Acting Commissioner of Patents and Trademarks